(12) United States Patent
Nique et al.

(10) Patent No.: US 7,968,581 B2
(45) Date of Patent: Jun. 28, 2011

(54) IMIDAZOLIDINE COMPOUNDS AS ANDROGEN RECEPTOR MODULATORS

(75) Inventors: François Nique, Le Perreux sur Marne (FR); Catherine Jagerschmidt, Romainville (FR); Florence Sylvie Namour, Romainville (FR); Roland Blanqué, Romainville (FR); Jean-Michel Lefrançois, Romainville (FR); Christophe Peixoto, Romainville (FR); Pierre Deprez, Romainville (FR); Nicolas Triballeau, Romainville (FR); Piet Tom Bert Paul Wigerinck, Mechelen (BE)

(73) Assignee: Galapagos NV, Mechelen (BE)

( * ) Notice: Subject to any disclaimer, the term of this patent is extended or adjusted under 35 U.S.C. 154(b) by 0 days.

(21) Appl. No.: 12/557,368

(22) Filed: Sep. 10, 2009

(65) Prior Publication Data
US 2010/0113547 A1 May 6, 2010

Related U.S. Application Data

(60) Provisional application No. 61/191,918, filed on Sep. 11, 2008.

(51) Int. Cl.
*A61K 31/4166* (2006.01)
*C07D 233/40* (2006.01)
*A61P 35/00* (2006.01)

(52) U.S. Cl. ..................................... 514/391; 548/319.1

(58) Field of Classification Search ............... 548/317.1; 514/389
See application file for complete search history.

(56) References Cited

U.S. PATENT DOCUMENTS

| | | | |
|---|---|---|---|
| 4,753,957 A | 6/1988 | Chan | |
| 4,873,256 A | 10/1989 | Coussediere et al. | |
| 4,992,443 A | 2/1991 | Chelen | |
| 5,750,553 A | 5/1998 | Claussner et al. | |
| 6,355,664 B1 | 3/2002 | Kelly et al. | |
| 2003/0195238 A1 | 10/2003 | Gil et al. | |
| 2004/0202825 A1 | 10/2004 | Malhotra | |

FOREIGN PATENT DOCUMENTS

| | | |
|---|---|---|
| DE | 2855770 A1 | 12/1978 |
| EP | 0091596 A2 | 3/1983 |
| EP | 0572191 A1 | 5/1993 |
| EP | 0760239 A2 | 8/1996 |
| EP | 0945441 A2 | 9/1999 |
| EP | 0966447 A1 | 12/1999 |
| JP | 01090114 | 6/1989 |
| JP | 02019363 | 1/1990 |
| JP | 06135937 A | 5/1994 |
| WO | 95/29909 | 11/1995 |
| WO | 97/19064 | 5/1997 |
| WO | 98/39303 | 11/1998 |
| WO | 98/57633 | 12/1998 |
| WO | 01/10799 | 2/2001 |
| WO | 01/85685 | 11/2001 |
| WO | 02/14865 | 2/2002 |
| WO | 2007/047146 | 4/2007 |
| WO | 2007/137874 | 12/2007 |

OTHER PUBLICATIONS

Angel_1987_Mol Cell Biol_2256, 12-O-tetradecanoyl-phorbol-13-acetate induction of the human collagenase gene is mediated by an inducible enhancer element located in the 5'-fla.
Claessens_1996_J Biol Chem_271_19013, The androgen-specific probasin response element 2 interacts differentially with androgen and glucocorticoid receptors.
Davison_2003_J Steroid Biochem Mol Biol_85_363, Androgens in women.
Hourdé_2008_Acta Physiol_195_471, Androgen replacement therapy improves function in male rat muscles independently of hypertrophy and activation of the Akt/mTOR pathway.
Kaufman 2005_Endocr Rev_26_833, The decline of androgen levels in elderly men and its clinical and therapeutic implications.
Kun_2003_Am J Physiol Endocrinol Metab_285_E363, Glucocorticoid-induced skeletal muscle atrophy is associated with upregulation of myostatin gene expression.
Liu_2004_J Clin Endocrinol Metab_89_4789, The rationale, efficacy and safety of androgen therapy in older men: future research and current practice recommendations.
Tilley_1989_PNAS_86_327, Characterization and expression of a cDNA encoding the human androgen receptor.
Molander_1995_J Org Chem_60_872, Stereochemical Investigations of Samarium(II) Iodide-Promoted 5-Exo and 6-Ex0 Ketyl-Olefin Radical Cyclization Reactions.

*Primary Examiner* — Kamal Saeed
(74) *Attorney, Agent, or Firm* — Klauber & Jackson LLC

(57) ABSTRACT

Novel compounds are disclosed that have a Formula represented by the following:

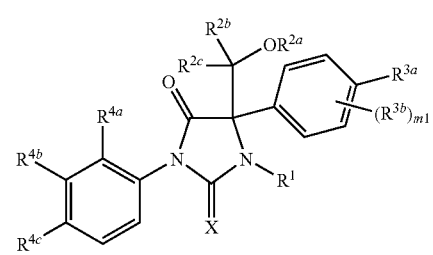

wherein X, $R^1$, $R^{2a}$, $R^{2b}$, $R^{2c}$, $R^{3a}$ $R^{3b}$, $R^{4a}$, $R^{4b}$, $R^{4c}$, and m1 are as described herein. The compounds may be prepared as pharmaceutical compositions, and may be used for the prevention and treatment of a variety of conditions in mammals including humans, including by way of non-limiting example, cachexia, osteoporosis, sarcopenia, a decline in libido and/or sexual dysfunction.

57 Claims, No Drawings

IMIDAZOLIDINE COMPOUNDS AS ANDROGEN RECEPTOR MODULATORS

RELATED APPLICATIONS

The present application claims the benefit under 35 U.S.C. §119 of U.S. Provisional Application No. 61/191,918, filed Sep. 11, 2008, and G.B. Application No. 0900333.6, filed Jan. 9, 2009, the contents of each of which are hereby incorporated by reference in their entireties.

BACKGROUND OF THE INVENTION

The present invention relates to imidazolidine compounds that can affect the activity of the androgen receptor (AR). In one aspect a compound of the invention is an antagonist or partial antagonist and is of use in the prevention and/or treatment of androgen dependent tumors and/or all the conditions in which AR stimulation could be detrimental such as acne, alopecia and/or hirsutism; or in an alternative aspect a compound of the invention is a selective androgen receptor modulator (agonist or mixed agonists/antagonist) that can be used in the treatment of conditions of cachexia and muscle wasting disorders (including but not limited to cancer-induced cachexia, HIV-induced, glucocorticoid-induced, immobilization-induced, diet-induced muscle loss, thermal burns, chronic renal failure, congestive heart failure, chronic obstructive pulmonary disease) age-related functional decline (including but not limited to sarcopenia) and/or male or female osteoporosis. The present invention also provides processes for the production of compounds of the invention, pharmaceutical compositions containing a compound of the invention and the use of a compound of the invention in the prevention or treatment of the disorders disclosed herein.

In men, androgens, of which testosterone and its metabolite 5α-DHT are the main endogenous representatives, are associated with the development and maintenance of the primary male characteristics (epididymis, vas deferens, prostate, external genitalia) and secondary male characteristics (development of hair, musculature of the larynx, distribution of fatty tissue, behaviour and libido). In addition, they contribute to muscle and bone development, and also act on the hematopoiesis, the central nervous system and sexual function.

In women, androgens have been involved inter alia in the development and maintenance of bone tissue and libido.

Progressive reduction in levels of circulating androgens in aging men (PADAM—partial androgen decline in aging men) contributes to a specific number of clinical manifestations, including osteoporosis, loss of muscle mass and strength, reduction in libido and sexual dysfunction, anemia and a change in cognition, mood swings, depression (see Review in: Kaufman J M and Vermeulen A., 2005, The decline of androgen levels in elderly men and its clinical and therapeutic implications Endocr Rev. 26:833-76). However, the clinical safety of androgen therapy for cardiovascular and prostate diseases is uncertain. Therefore, androgen supplementation is not recommended for healthy, elderly men (Liu P Y et al. 2004, Clinical review, 171: The rationale, efficacy and safety of androgen therapy in older men: future research and current practice recommendations. J. Clin. Endocrinol. Metab. 89:4789-96).

A syndrome associated with the reduction in levels of circulating androgens (ADIF—androgen decline in female) has also been described in women. It can have various causes, including aging, chemotherapy and infection by the AIDS virus. Associated symptoms include: osteoporosis/osteopenia, sarcopenia and muscle weakness, reduction in libido, sexual dysfunction, change of cognition, mood swings, and depression. Endometriosis and an increased risk of breast, uterine and ovarian cancers have also been described (Davison S L and Davis S R 2003 Androgens in women. J. Steroid Biochem. Mol. Biol. 85:363-366). The administration of high doses of androgens to women can lead to the appearance of signs of masculinisation, mood swings and acne. These risks must be taken into consideration when administering androgens to women.

The limitations to the use of steroidal androgen receptors agonists or antagonists, becomes clear as these are plagued with undesirable effects due to their metabolisation into other sex-hormones and steroids, which in-turn induce undesirable effects.

Therefore, non-steroidal alternatives are being investigated and are particularly desired because they allow the beneficial effects of testosterone on specific organs (bone and muscle tissue) and on the libido to be maintained, and are less likely to lead to secondary effects in specific tissues, such as the prostate in men and the uterus in women, as they would not interfere with the hormonal system. They represent a safer alternative to conventional therapies in any pathologies linked with an androgen deficit, including osteoporosis or sarcopenia, and decline in libido associated with syndromes of the PADAM and ADIF type. They may also be used in the treatment of cachexia induced by specific diseases, such as cancer or AIDS, or in the treatment of muscle loss induced by long-term treatment with glucocorticoids. Moreover, they may be used in the treatment of androgen dependent tumors, such as prostate cancer, or hyperplasia, which growth at an early stage can usually be regulated by administering steroidal anti-androgens.

Selective modulators of the androgen receptor (SARMs—selective androgen receptor modulators) of non-steroidal structure are molecules which act as ligands of the androgen receptor (AR) with a degree of tissue specificity.

The importance of the AR as a target is great in many areas of drug discovery and therapy. The compounds of the invention disclosed herein are suggested to have two main modes of action:

As antagonists (complete or partial), inhibitors of the AR may be employed in oncology, and may be particularly useful in the treatment of androgen dependent prostate cancer. They may also be used for male contraception and benign hyperplasia of the prostate, ovarian and breast cancer (for a comparative review, see Mohler et al., Expert Opin. Ther. Patents (2005) 15(11), 1565-1585).

As agonists (complete or partial, including mixed agonists/antagonists), they may be particularly useful for metabolic and endocrine diseases disorders, especially age-related diseases and conditions of cachexia. Additionally due to their presence in bone-cells, SARMs advantageously may be used in the development and maintenance of the skeleton.

Unfortunately currently available androgens are still flawed with side effects, (such as gynecomastia or breast tenderness), due to low tissue selectivity and potent SARMs with fewer side effects are highly desirable.

EP-A-0966447 discloses a number of imidazolidine compounds useful in the treatment of inflammatory and immune cell-mediated conditions, and which act by inhibiting the interaction of cellular adhesion molecules. Although the compounds disclosed therein are similar to those of the present invention, in some respects, there is no disclosure of any compounds falling within the scope of the present invention.

EP-A-0572191 discloses certain imidazolidines substituted with an iodopropargyl group, useful as antimicrobial agents.

WO 2007/137874 discloses imidazolidine compounds similar to those of the present invention but wherein, in Formula (I), at least one of $R^{3a}$ or $R^{3b}$ is OH, SH or a derivative thereof. These compounds require an OH or SH group to be available in the active compounds in order to be able to bind His-874 of the androgen receptor. These compounds show high in vitro activity but disappointingly low in vivo activity, such that these compounds are not deemed commercially viable.

Surprisingly, it has now been found that in vivo activity can be substantially increased by eliminating the weakly acidic phenolic OH or SH group, or derivatives that can yield this OH or SH, from the $R^3$ position.

SUMMARY OF THE INVENTION

The compounds of the invention may show good absorption, good half-life, good solubility, good bioavailability, and good metabolic stability. In a particular aspect, a compound of the invention exhibits unexpected significant improvements in pharmacological properties, in particular improved bioavailability.

Thus, the present invention provides imidazolidine derivatives, and methods for identifying and designing a compound of the invention, which compound affects the activity of androgen receptors.

In particular the present invention provides a compound of the invention according to Formula Ia below:

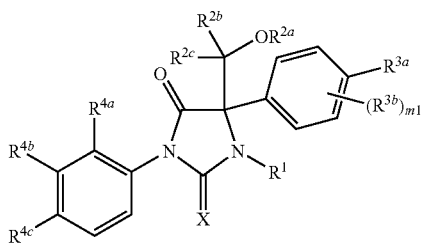

Ia wherein
X is O or S;
$R^1$ is H; or
$R^1$ is selected from $C_1$-$C_6$ alkyl, $C_3$-$C_7$ cycloalkyl, $C_3$-$C_6$ alkenyl, $C_3$-$C_6$ alkynyl, and $C_1$-$C_6$ acyl; each of which may optionally be substituted with cyano, one or more halo, hydroxyl, or unsubstituted $C_1$-$C_6$ alkoxy;
$R^{2a}$ is selected from H, $S(O_2)OH$, $P(O)(OH)_2$, and $C(O)(CH_2)_{n1}C(O)OH$; or
$R^{2a}$ is selected from $C_1$-$C_6$ alkyl, $C_1$-$C_6$ acyl, and $C_3$-$C_6$ alkenyl; each of which may optionally be substituted with aryl, amino, or carboxy; n1 is 0, 1, 2, 3, or 4;
each $R^{2b}$ and $R^{2c}$ is independently selected from H, and $C_1$-$C_6$ alkyl; or
$R^{2b}$ and $R^{2c}$ may join together to form a $C_3$-$C_7$ cycloalkyl;
$R^{3a}$ is H, halo, cyano, or nitro; or
$R^{3a}$ is $C_1$-$C_6$ alkyl optionally substituted with halo, cyano, nitro, hydroxyl, or $C_1$-$C_4$ alkoxy; or
$R^{3a}$ is amido optionally substituted with $C_1$-$C_6$ alkyl;
each $R^{3b}$ is independently halo, cyano, or nitro; or
each $R^{3b}$ is independently $C_1$-$C_6$ alkyl optionally substituted with cyano, or halo; or
each $R^{3b}$ is amido, optionally substituted with $C_1$-$C_6$ alkyl;
each $R^{4a}$, and $R^{4b}$ is independently H, halo, cyano, carboxy or nitro; or
each $R^{4a}$, and $R^{4b}$ is selected from $C_1$-$C_6$ alkyl, and $C_1$-$C_6$ alkoxy; each of which may optionally be substituted by one or more halo, or $C_1$-$C_6$ alkoxy;
or $R^{4a}$ and $R^{4b}$ are joined together to form a 5 or 6-membered cycloalkyl, 5 or 6-membered heterocycloalkyl, 5 or 6-membered aryl, or 5 or 6-membered heteroaryl;
$R^{4c}$ is halo, cyano, or nitro; and
m1 is 0, 1, or 2.

In a further embodiment, the present invention provides a compound of the invention according to Formula Ib below:

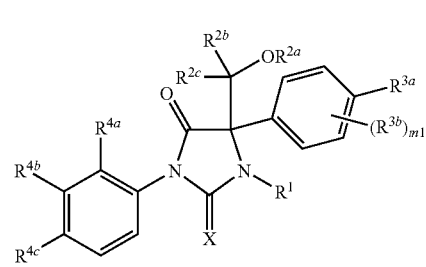

Ib wherein
X is O or S;
$R^1$ is H; or
$R^1$ is selected from $C_1$-$C_6$ alkyl, $C_3$-$C_7$ cycloalkyl, $C_3$-$C_6$ alkenyl, $C_3$-$C_6$ alkynyl, and $C_1$-$C_6$ acyl; each of which may optionally be substituted with cyano, one or more halo, hydroxyl, or unsubstituted $C_1$-$C_6$ alkoxy;
$R^{2a}$ is selected from H, $P(O)(OH)_2$, and $C(O)(CH_2)_{n1}C(O)$ OH; or
$R^{2a}$ is selected from $C_1$-$C_6$ acyl, and $C_3$-$C_6$ alkenyl; each of which may optionally be substituted with amino, or carboxy; n1 is 0, 1, 2, 3, or 4;
each $R^{2b}$ and $R^{2c}$ is independently selected from H, and $C_1$-$C_6$ alkyl; or
$R^{2b}$ and $R^{2c}$ may join together to form a $C_3$-$C_7$ cycloalkyl;
$R^{3a}$ is H, halo, cyano, or nitro; or
$R^{3a}$ is $C_1$-$C_6$ alkyl optionally substituted with halo, cyano, nitro, hydroxyl, or $C_1$-$C_4$ alkoxy; or
$R^{3a}$ is amido optionally substituted with $C_1$-$C_6$ alkyl;
each $R^{3b}$ is independently halo, cyano, or nitro; or
each $R^{3b}$ is independently $C_1$-$C_6$ alkyl optionally substituted with cyano, or halo; or
each $R^{3b}$ is amido, optionally substituted with $C_1$-$C_6$ alkyl;
each $R^{4a}$, and $R^{4b}$ is independently H, halo, cyano, carboxy or nitro; or
each $R^{4a}$, and $R^{4b}$ is selected from $C_1$-$C_6$ alkyl, and $C_1$-$C_6$ alkoxy; each of which may optionally be substituted by one or more halo, or $C_1$-$C_6$ alkoxy;
or $R^{4a}$ and $R^{4b}$ are joined together to form a 5 or 6-membered cycloalkyl, 5 or 6-membered heterocycloalkyl, 5 or 6-membered aryl, or 5 or 6-membered heteroaryl;
$R^{4c}$ is halo, cyano, or nitro; and
m1 is 0, 1, or 2.

In a further embodiment, a compound of the invention is according to Formula (VI):

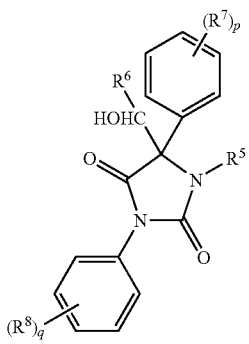

VI wherein:
R⁵ is H, $C_{1-6}$ alkyl, $C_{2-6}$ alkenyl, $C_{2-6}$ alkynyl, or $C_{1-4}$ alkyl substituted with a cyano group or one or more halo groups;
R⁶ is H or $C_{1-4}$ alkyl;
R⁷ is halo, cyano, $C_{1-4}$ alkyl, or $C_{1-4}$ perfluoroalkyl;
R⁸ is halo, cyano, nitro, $C_{1-4}$ alkyl, or $C_{1-4}$ perfluoroalkyl;
p is 0, 1, or 2;
q is 1, 2, or 3;
when p is 2 then each R⁷ is the same or different;
when q is 2 or 3 then each R⁸ is the same or different, and pharmaceutically acceptable esters thereof.

In another further embodiment, a compound of the invention is according to Formula VII

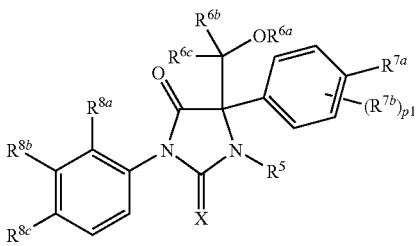

(VII)

wherein
X is O;
R⁵ is H, $C_1$-$C_6$ alkyl, $C_3$-$C_6$ alkenyl, or $C_3$-$C_6$ alkynyl, each of which may be unsubstituted or substituted with cyano, one or more halo;
$R^{6a}$ is H, or a phosphoric ester or derivative thereof, or a carboxylic ester, and preferably $P(O)(OH)_2$, $C(=O)—(CH_2)_2—CO_2H$, or $—C(=O)CH(NH_3Cl)iPr$;
$R^{6b}$ is H;
$R^{6c}$ is independently selected from H, and $C_1$-$C_6$ alkyl;
$R^{7a}$ is H, halo, cyano, $C_1$-$C_4$ alkyl, which may be unsubstituted or substituted with one or more halo;
$R^{7b}$ is halo, cyano, or $C_1$-$C_4$ alkyl, which may be unsubstituted or substituted with halo; each
$R^{8a}$, and $R^{8b}$ is independently H, halo, cyano, $C_1$-$C_4$ alkyl, each of which may be unsubstituted or substituted by one or more halo;
$R^{8c}$ is halo, cyano or nitro; and
$p_1$ is 0, 1, or 2.

In a further aspect, the present invention provides pharmaceutical compositions comprising a compound of the invention, and a pharmaceutical carrier, excipient or diluent. In this aspect of the invention, the pharmaceutical composition can comprise one or more of the compounds of the invention described herein. Moreover, a compound of the invention useful in the pharmaceutical compositions and treatment methods disclosed herein, is pharmaceutically acceptable as prepared and used.

In a further aspect of the invention, this invention provides a method of treating a mammal susceptible to or afflicted with a condition from among those listed herein, and particularly age-related diseases including, but not limited to sarcopenia, conditions of cachexia and muscle loss induced by diseases including, but not limited to, cancer and AIDS, bone and joint diseases, such as osteoporosis, reduction in libido and sexual dysfunction or anemia, which method comprises administering an effective amount of an agonist or mixed agonist/antagonist compound of the invention or a pharmaceutical composition comprising an agonist or mixed agonist/antagonist compound of the invention as herein described.

In a further aspect, the present invention provides a method of treating a mammal susceptible to or afflicted with androgen-dependent tumors, such as prostate cancer or hyperplasia, which method comprises administering an effective amount of an antagonist compound of the invention or a pharmaceutical composition comprising an antagonist compound of the invention as herein described.

In a further aspect, the present invention provides a compound of the invention for use in the treatment or prevention of a condition selected from those listed herein, and particularly age-related diseases, including, but not limited to sarcopenia, conditions of cachexia and muscle loss induced by diseases including, but not limited to, cancer and AIDS, chronic obstructive pulmonary disease, chronic renal failure, thermal burns, bone and joint diseases, such as osteoporosis, reduction in libido and sexual dysfunction or anemia, which method comprises administering an effective amount of an agonist or mixed agonist/antagonist compound of the invention or a pharmaceutical composition comprising an agonist or mixed agonist/antagonist compound of the invention as herein described.

In a further aspect, the present invention provides a compound of the invention for use in the treatment or prevention of a condition selected from those listed herein, such as prostate cancer or hyperplasia which method comprises administering an effective amount of an antagonist compound of the invention or a pharmaceutical composition comprising an antagonist compound of the invention as herein described.

In additional aspects, this invention provides methods for synthesizing a compound of the invention, with representative synthetic protocols and pathways disclosed later on herein.

In a further aspect, the present invention provides methods for determining the agonistic or antagonistic activity of a compound of the invention described herein.

Accordingly, it is a principal object of this invention to provide a novel series of compounds, which can modulate the activity of the androgen receptor (AR) and thus prevent or treat any maladies that may be causally related to aberrant activity thereof.

It is a further object of the present invention to provide a compound of the invention as aforesaid that can function as an agonist or mixed agonist/antagonist of the AR, and is thereby effective to treat or alleviate maladies such as age-related diseases including, but not limited to sarcopenia, conditions of cachexia and muscle loss induced by diseases including, but not limited to, cancer and AIDS, bone and joint diseases, such as osteoporosis, reduction in libido and sexual dysfunction or anemia.

It is further an object of this invention to provide a series of compounds that can act as antagonists of AR, and that thereby are effective to treat or alleviate maladies or symptoms of same, such as androgen dependent prostate cancer, male contraception and benign hyperplasia of the prostate, ovarian and breast cancer. In one aspect a compound of the invention is an antagonist or partial antagonist and is of use in the prevention and/or treatment of androgen dependent tumors and all the conditions in which AR stimulation could be detrimental such as acne, alopecia and hirsutism; or in an alternative aspect the compound of the invention is a selective androgen receptor modulator (agonist or mixed agonist/antagonist) that can be used in the treatment of conditions of cachexia and muscle wasting disorders (including but not limited to cancer-induced cachexia, HIV-induced, glucocorticoid-induced, immobilisation-induced, diet-induced muscle loss, thermal burns, chronic renal failure, chronic obstructive pulmonary disease) age-related functional decline (including but not limited to sarcopenia) and male and female osteoporosis.

The present invention also provides processes for the production of a compound of the invention, pharmaceutical compositions containing a compound of the invention and the use of a compound of the invention in the prevention or treatment of any one of the disorders disclosed herein.

A still further object of this invention is to provide pharmaceutical compositions comprising or including a compound of the invention, for the therapeutic uses recited herein.

It is a still further object of the invention to provide methods of treatment employing a compound of the invention and/or a pharmaceutical composition of the invention.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds of the invention, pharmaceutical compositions containing such compounds of the invention and methods of using such compounds of the invention and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example "an analogue" means one analogue or more than one analogue.

'Acyl' refers to a radical —C(O)$R^{20}$, where $R^{20}$ is hydrogen, $C_1$-$C_6$ alkyl, $C_3$-$C_7$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_6$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4.

'Acylamino' refers to a radical —$NR^{22}C(O)R^{23}$, where $R^{22}$ is hydrogen, $C_1$-$C_6$ alkyl, $C_3$-$C_7$ cycloalkyl, 4-10 membered heterocycloalkyl, $C_6$-$C_{10}$ aryl, arylalkyl, 5-10 membered heteroaryl or heteroarylalkyl and $R^{23}$ is hydrogen, $C_1$-$C_6$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino Exemplary 'acylamino' groups are $NR^{21'}C(O)$—$C_1$-$C_6$ alkyl, —$NR^{21'}C(O)$—$(CH_2)_t(C_6$-$C_{10}$ aryl), —$NR^{21'}C(O)$—$(CH_2)_t$(5-10 membered heteroaryl), $NR^{21'}C(O)$—$(CH_2)_t(C_3$-$C_7$ cycloalkyl), and —$NR^{21'}C(O)$—$(CH_2)_t$(4-10 membered heterocycloalkyl), wherein t is an integer from 0 to 4, each $R^{21'}$ independently represents H or $C_1$-$C_6$ alkyl.

'Alkoxy' refers to the group —$OR^{26}$ where $R^{26}$ is $C_1$-$C_6$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkoxycarbonyl' refers to a radical —C(O)—$OR^{27}$ where $R^{27}$ represents an $C_1$-$C_6$ alkyl, $C_3$-$C_7$ cycloalkyl, $C_3$-$C_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—$C_1$-$C_6$ alkyl, —C(O)O—$(CH_2)_t(C_6$-$C_{10}$ aryl), —C(O)O—$(CH_2)_t$(5-10 membered heteroaryl), —C(O)O—$(CH_2)_t(C_3$-$C_7$ cycloalkyl), and —C(O)O—$(CH_2)_t$(4-10 membered heterocycloalkyl), wherein t is an integer from 1 to 4.

'O-Aryl-carbonyl' refers to a radical —C(O)—$OR^{29}$ where $R^{29}$ represents an $C_6$-$C_{10}$ aryl, as defined herein. Exemplary "O-Aryl-carbonyl" groups is —C(O)O—$(C_6$-$C_{10}$ aryl).

'Hetero-O-Aryl-carbonyl' refers to a radical —C(O)—$OR^{31}$ where $R^{31}$ represents a 5-10 membered heteroaryl, as defined herein.

'Alkyl' means straight or branched aliphatic hydrocarbon 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Amino' refers to the radical —$NH_2$.

'Alkylamino' refers to the group —$NHR^{34}$, wherein $R^{34}$ is $C_1$-$C_6$ alkyl.

'Alkylarylamino' refers to the group —$NR^{36}R^{37}$, wherein $R^{36}$ is $C_6$-$C_{10}$ aryl and $R^{37}$ is $C_1$-$C_6$ alkyl.

'Arylamino' means a radical —$NHR^{40}$ where $R^{40}$ is selected from $C_6$-$C_{10}$ aryl and 5-10 membered heteroaryl as defined herein.

'Dialkylamino' refers to the group —$NR^{40}R^{43}$ wherein each of $R^{42}$ and $R^{43}$ are independently selected from $C_1$-$C_6$ alkyl.

'Diarylamino' refers to the group —$NR^{46}R^{47}$ wherein each of $R^{46}$ and $R^{47}$ are independently selected from $C_6$-$C_{10}$ aryl.

'Aminosulfonyl' or 'sulfonamide' refers to the radical —$S(O_2)NH_2$.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Amido' refers to the radical —C(O)NH$_2$.

'Carboxy' refers to the radical —C(O)OH.

'Cycloalkyl' refers to cyclic non-aromatic hydrocarbyl groups having from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative aryl having hetero atoms containing substitution include the following:

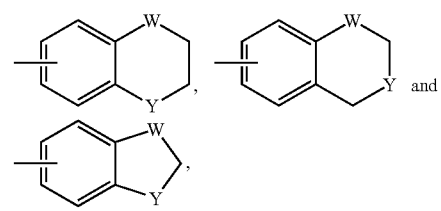

wherein each W is selected from C(R$^{54}$)$_2$, NR$^{54}$, O and S; and each Y is selected from carbonyl, NR$^{54}$, O and S; and R$^{54}$ is independently hydrogen, C$_1$-C$_6$ alkyl, C$_3$-C$_{70}$ cycloalkyl, 4-10 membered heterocycloalkyl, C$_6$-C$_{10}$ aryl, and 5-10 membered heteroaryl.

Examples of representative heteroaryls include the following:

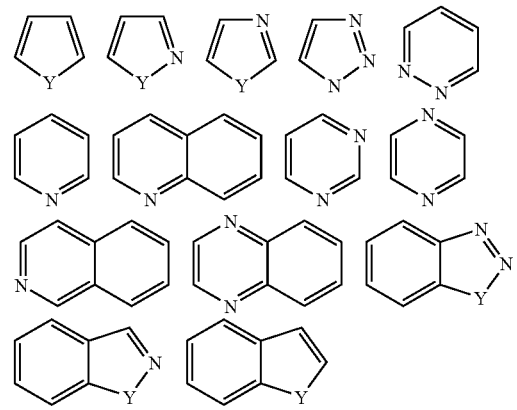

wherein each Y is selected from carbonyl, N, NR$^{55}$, O and S; and R$^{55}$ is independently hydrogen, C$_1$-C$_6$ alkyl, C$_3$-C$_7$ cycloalkyl, 4-10 membered heterocycloalkyl, C$_6$-C$_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

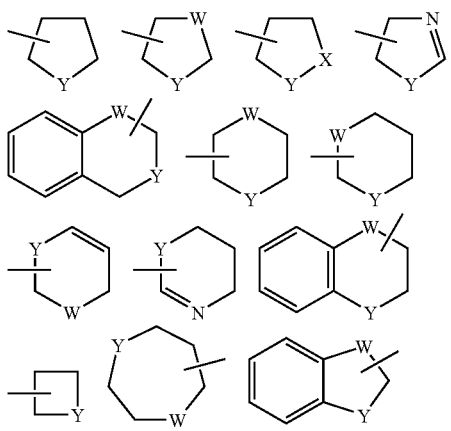

wherein each W is selected from $CR^{56}$, $C(R^{56})_2$, $NR^{56}$, O and S; and each Y is selected from $NR^{56}$, O and S; and $R^{56}$ is independently hydrogen, $C_1$-$C_6$ alkyl, $C_3$-$C_7$ cycloalkyl, 4-10 membered heterocycloalkyl, $C_6$-$C_{10}$ aryl, 5-10 membered heteroaryl, These heterocycloalkyl rings may be optionally substituted with one or more groups selected from the group consisting of acyl, acylamino, acyloxy (—O-acyl or —OC(O)$R^{20}$), alkoxy, alkoxycarbonyl, alkoxycarbonylamino (—NR"-alkoxycarbonyl or —NH—C(O)—$OR^{27}$), amino, substituted amino, aminocarbonyl (amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, —O-Aryl, azido, carboxyl, cyano, cycloalkyl, halogen, hydroxy, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:

halogen, —$R^{57}$, —O⁻, =O, —$OR^{57}$, —$SR^{57}$, —S⁻, =S, —$NR^{57}R^{58}$, =$NR^{57}$, —CCl$_3$, —CF$_3$, —CN, —OCN, —SCN, —NO, —NO$_2$, =N$_2$, —N$_3$, —S(O)$_2$O⁻, —S(O)$_2$OH, —S(O)$_2R^{57}$, —OS(O)$_2$O⁻, —OS(O)$_2R^{57}$, —P(O)(O⁻)$_2$, —P(O)($OR^{57}$)(O⁻), —OP(O)($OR^{57}$)($OR^{58}$), —C(O)$R^{57}$, —C(S)$R^{57}$, —C(O)$OR^{57}$, —C(O)$NR^{57}R^{58}$, —C(O)O⁻, —C(S)$OR^{57}$, —$NR^{59}$C(O)$NR^{57}R^{58}$, —$NR^{59}$C(S)$NR^{57}R^{58}$, —$NR^{60}$C($NR^{59}$)$NR^{57}R^{58}$ and —C($NR^{59}$)$NR^{57}R^{58}$;

wherein each $R^{57}$, $R^{58}$, $R^{59}$ and $R^{60}$ are independently:

hydrogen, $C_1$-$C_6$ alkyl, $C_6$-$C_{10}$ aryl, arylalkyl, $C_3$-$C_7$ cycloalkyl, 4-10 membered heterocycloalkyl, 5-10 membered heteroaryl, heteroarylalkyl; or $C_1$-$C_6$ alkyl substituted with halo or hydroxy; or $C_6$-$C_{10}$ aryl, 5-10 membered heteroaryl, $C_6$-$C_7$ cycloalkyl or 4-10 membered heterocycloalkyl substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

In a particular embodiment, substituted groups are substituted with one or more substituents, particularly with 1 to 3 substituents, in particular with one substituent group.

'Perfluoro' when used as a prefix, refers to a group were all the hydrogen atom(s) of said group have been replaced with fluorine atoms. Particularly, the term perfluoroalkyl, refers to an alkyl (as defined herein) in which all the hydrogen atoms have been replaced by fluorine atoms. A particular perfluoroalkyl group is CF$_3$.

In a further particular embodiment the substituent group or groups are selected from: halo, cyano, nitro, trifluoromethyl, trifluoromethoxy, azido, —NR'''SO$_2$R'', —SO$_2$NR''R''', —C(O)R'', —C(O)OR'', —OC(O)R'', —NR'''C(O)R'', —C(O)NR''R''', —NR''R''', —(CR''R''')$_m$OR''', wherein, each R'' is independently selected from H, $C_1$-$C_6$ alkyl, —(CH$_2$)$_t$($C_6$-$C_{10}$ aryl), —(CH$_2$)$_t$(5-10 membered heteroaryl), —(CH$_2$)$_t$($C_3$-$C_7$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each R'' independently represents H or $C_1$-$C_6$ alkyl.

'Sulfo' or 'sulfonic acid' refers to a radical such as —SO$_3$H.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable esters' are those which are sufficiently non-toxic to be regulatorily approvable. Preferred esters are phosphoric esters and derivatives thereof, and carboxylic esters. In general, pharmaceutically acceptable esters may be formed with pharmaceutically acceptable acids, such as phosphoric acid and ester-forming derivatives thereof, such as alkyl and dialkyl esters of phosphoric acid, and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, 4-methylbicyclo[2.2.2]-oct-2-ene-1-carboxylic acid, glucoheptonic acid, 3-phenylpropionic acid, trimethylacetic acid, tertiary butylacetic acid, gluconic acid, glutamic acid, hydroxynaphthoic acid, salicylic acid, stearic acid, muconic acid, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives, N-alkylmorpholine esters, glycine, valine or other aminoacid esters and the like, carboxylic acid esters, sulfate or phosphate esters.

'Solvate' refers to forms of a compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound of the invention that, when administered to a subject for treating a disease, is sufficient to effect such treatment for the disease. The "therapeutically effective amount" can vary depending on the compound of the invention, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma.

As used herein the term 'agonist' is used to describe a type of compound that binds to a receptor and triggers a signal transduction reaction. The ability to alter the activity of a receptor, also known as the agonist's efficacy, refers to the ability of a compound to induce a biological response in its molecular target.

As used herein, the term 'antagonist' is used to describe a compound that does not provoke a biological response itself upon binding to a receptor, but blocks or dampens agonist-mediated responses.

As used herein the term 'compound(s) of the invention', and equivalent expressions, are meant to embrace compounds of the Formula (e) as hereinbefore described, which expression includes, the pharmaceutically acceptable salts, and the solvates of the compounds or the solvates of the pharmaceutically acceptable salts, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_6$ alkyl, the citation of a range should be considered a representation of each member of said range.

Other derivatives of the compounds of the invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of the invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compound may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N and would be useful in Positron Emission Topography (PET) studies for examining substrate receptor occupancy.

All isotopic variants of a compound of the invention provided herein, radioactive or not, are intended to be encompassed within the scope of compounds of the invention as herein defined.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

All stereoisomers of the compounds are encompassed within the term compound of the invention as used herein. A compound of the invention is generally available as stereoisomers at the stereocentre on the imidazole ring. The present invention envisages the use of either enantiomer, or racemic mixtures in any proportions, where there is an optical centre.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro- forms of phenylnitromethane, that are likewise formed by treatment with acid or base.

Tautomeric forms may be relevant to the attainment of the optimal chemical reactivity and biological activity of a compound of interest. As used herein, the term compound of the invention includes the tautomeric forms of the compounds disclosed.

The Compounds

The present invention and provides imidazolidine derivatives, and methods for identifying and designing such compounds. In particular the present invention provides a compound of the invention according to Formula Ia below:

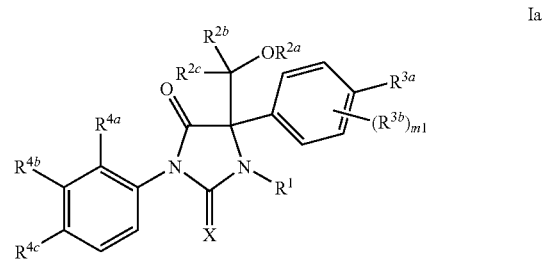

Ia wherein
X is O or S;
$R^1$ is H; or
  $R^1$ is selected from $C_1$-$C_6$ alkyl, $C_3$-$C_7$ cycloalkyl, $C_3$-$C_6$ alkenyl, $C_3$-$C_6$ alkynyl, and $C_1$-$C_6$ acyl; each of which may optionally be substituted with cyano, one or more halo, hydroxyl, or unsubstituted $C_1$-$C_6$ alkoxy;
$R^{2a}$ is selected from H, S($O_2$)OH, P(O)(OH)$_2$, and C(O)(CH$_2$)$_{n1}$C(O)OH; or
  $R^{2a}$ is selected from $C_1$-$C_6$ alkyl, $C_1$-$C_6$ acyl, and $C_3$-$C_6$ alkenyl; each of which may optionally be substituted with aryl, amino, or carboxy; n1 is 0, 1, 2, 3, or 4;
each $R^{2b}$ and $R^{2c}$ is independently selected from H, and $C_1$-$C_6$ alkyl; or
  $R^{2b}$ and $R^{2c}$ may join together to form a $C_3$-$C_7$ cycloalkyl;
$R^{3a}$ is H, halo, cyano, or nitro; or
  $R^{3a}$ is $C_1$-$C_6$ alkyl optionally substituted with halo, cyano, nitro, hydroxyl, or $C_1$-$C_4$ alkoxy; or
  $R^{3a}$ is amido optionally substituted with $C_1$-$C_6$ alkyl;

each $R^{3b}$ independently is halo, cyano, or nitro; or
  each $R^{3b}$ is independently $C_1$-$C_6$ alkyl optionally substituted with cyano, or halo; or
  each $R^{3b}$ is amido, optionally substituted with $C_1$-$C_6$ alkyl;
each $R^{4a}$, and $R^{4b}$ is independently H, halo, cyano, carboxy or nitro; or
  each $R^{4a}$, and $R^{4b}$ is selected from $C_1$-$C_6$ alkyl, and $C_1$-$C_6$ alkoxy; each of which may optionally be substituted by one or more halo, or $C_1$-$C_6$ alkoxy;
  or $R^{4a}$ and $R^{4b}$ are joined together to form a 5 or 6-membered cycloalkyl, 5 or 6-membered heterocycloalkyl, 5 or 6-membered aryl, or 5 or 6-membered heteroaryl;
$R^{4c}$ is halo, cyano, or nitro; and
m1 is 0, 1, or 2.

In particular the present invention provides a compound of the invention according to Formula Ib below:

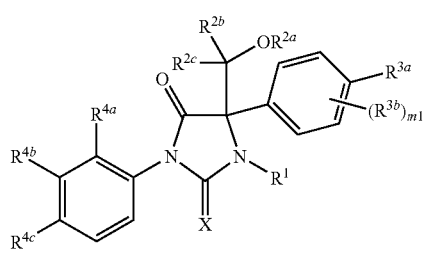

Ib wherein
X is O or S;
$R^1$ is H; or
  $R^1$ is selected from $C_1$-$C_6$ alkyl, $C_3$-$C_7$ cycloalkyl, $C_3$-$C_6$ alkenyl, $C_3$-$C_6$ alkynyl, and $C_1$-$C_6$ acyl; each of which may optionally be substituted with cyano, one or more halo, hydroxyl, or $C_1$-$C_6$ alkoxy;
$R^{2a}$ is selected from H, P(O)(OH)$_2$, and C(O)(CH$_2$)$_{n1}$C(O)OH; or
  $R^{2a}$ is selected from $C_1$-$C_6$ acyl, and $C_3$-$C_6$ alkenyl; each of which may optionally be substituted with amino, or carboxy; n1 is 0, 1, 2, 3, or 4;
each $R^{2b}$ and $R^{2c}$ is independently selected from H, and $C_1$-$C_6$ alkyl; or
$R^{2b}$ and $R^{2c}$ may join together to form a $C_3$-$C_7$ cycloalkyl;
$R^{3a}$ is H, halo, cyano, or nitro; or
  $R^{3a}$ is $C_1$-$C_6$ alkyl optionally substituted with halo, cyano, nitro, hydroxyl, or $C_1$-$C_4$ alkoxy; or
  $R^{3a}$ is amido optionally substituted with $C_1$-$C_6$ alkyl;
each $R^{3b}$ is independently halo, cyano, or nitro; or
  each $R^{3b}$ is independently $C_1$-$C_6$ alkyl optionally substituted with cyano, or halo; or
  each $R^{3b}$ is amido, optionally substituted with $C_1$-$C_6$ alkyl;
each $R^{4a}$, and $R^{4b}$ is independently H, halo, cyano, carboxy or nitro; or
  each $R^{4a}$, and $R^{4b}$ is selected from $C_1$-$C_6$ alkyl, and $C_1$-$C_6$ alkoxy; each of which may optionally be substituted by one or more halo, or $C_1$-$C_6$ alkoxy;
  or $R^{4a}$ and $R^{4b}$ are joined together to form a 5 or 6-membered cycloalkyl, 5 or 6-membered heterocycloalkyl, 5 or 6-membered aryl, or 5 or 6-membered heteroaryl;
$R^{4c}$ is halo, cyano, or nitro; and
m1 is 0, 1, or 2.

In one embodiment, with respect to a compound of the invention according to Formula Ia or Ib, X is O.

In one embodiment, with respect to a compound of the invention according to Formula Ia or Ib, $R^{2b}$ is H.

In a further embodiment, with respect to a compound of the invention according to Formula Ia or Ib, $R^{2b}$ is Me or Et.

In another embodiment, with respect to a compound of the invention according to Formula Ia or Ib, $R^{2c}$ is $C_1$-$C_6$ alkyl.

In a further embodiment, with respect to a compound of the invention according to Formula Ia or Ib, $R^{2c}$ is H, Me or Et.

In one embodiment, with respect to a compound of the invention according to Formula Ia or Ib, $R^{2b}$ and $R^{2c}$ are joined together to form a cyclopropyl, or cyclobutyl ring.

In one embodiment, with respect to a compound of the invention according to Formula Ia or Ib, each $R^{2b}$ and $R^{2c}$ is H.

In another embodiment, with respect to a compound of the invention according to Formula Ia, $R^{2a}$ is H, S(O$_2$)OH, or P(O)(OH)$_2$, $C_1$-$C_6$ alkyl (which $C_1$-$C_6$ alkyl may optionally be substituted with aryl), or $C_1$-$C_6$ acyl (which $C_1$-$C_6$ acyl may optionally be substituted with amino, carboxy).

In another embodiment, with respect to a compound of the invention according to Formula Ib, $R^{2a}$ is H, or P(O)(OH)$_2$, or $C_1$-$C_6$ acyl (which $C_1$-$C_6$ acyl may optionally be substituted with amino, carboxy).

In another embodiment, with respect to a compound of the invention according to Formula Ia, $R^{2a}$ is $C_1$-$C_6$ alkyl optionally substituted with aryl.

In another embodiment, with respect to a compound of the invention according to Formula Ia or Ib, $R^{2a}$ is $C_1$-$C_6$ acyl optionally substituted with amino, or carboxy.

In another embodiment, with respect to a compound of the invention according to Formula Ia or Ib, $R^{2a}$ is H.

In another embodiment, with respect to a compound of the invention according to Formula Ia or Ib, $R^{2a}$ is $C_3$-$C_6$ alkenyl.

In a further embodiment, with respect to a compound of the invention according to Formula Ia or Ib, $R^{2a}$ is CH$_2$—CH=CH$_2$.

In a further embodiment, with respect to a compound of the invention according to Formula Ia, $R^{2a}$ is benzyl.

In another embodiment, with respect to a compound of the invention according to Formula Ia, $R^{2a}$ is S(O$_2$)OH, or P(O)(OH)$_2$.

In another embodiment, with respect to a compound of the invention according to Formula Ia, $R^{2a}$ is a pharmaceutically acceptable salt of S(O$_2$)OH.

In another embodiment, with respect to a compound of the invention according to Formula Ia, $R^{2a}$ is S(O$_2$)ONa.

In another embodiment, with respect to a compound of the invention according to Formula Ib, $R^{2a}$ is P(O)(OH)$_2$.

In another embodiment, with respect to a compound of the invention according to Formula Ia or Ib, $R^{2a}$ is a mono or bis pharmaceutically acceptable salt of P(O)(OH)$_2$.

In another embodiment, with respect to a compound of the invention according to Formula Ia or Ib, $R^{2a}$ is P(O)(ONa)$_2$.

In another embodiment, with respect to a compound of the invention according to Formula Ia or Ib, $R^{2a}$ is C(O)(CH$_2$)$_{n1}$C(O)OH; and n1 is 0, 1, 2, or 3.

In another embodiment, with respect to a compound of the invention according to Formula Ia or Ib, $R^{2a}$ is C(O)—CH$_2$CH$_2$—C(O)OH.

In another embodiment, with respect to a compound of the invention according to Formula Ia or Ib, $R^{2a}$ is an pharmaceutically acceptable salt of C(O)—CH$_2$CH$_2$—C(O)OH.

In another embodiment, with respect to a compound of the invention according to Formula Ia or Ib, $R^{2a}$ is C(O)—CH$_2$CH$_2$—C(O)ONa.

In another embodiment, with respect to a compound of the invention according to Formula Ia or Ib, $R^{2a}$ is C(O)—CH(iPr)NH$_2$.

In another embodiment, with respect to a compound of the invention according to Formula Ia or Ib, $R^{2a}$ is C(O)—CH(iPr)NH$_3$Cl.

In one embodiment, with respect to a compound of the invention according to Formula Ia or Ib, $R^1$ is H.

In another embodiment, with respect to a compound of the invention according to Formula Ia or Ib, $R^1$ is $C_1$-$C_6$ alkyl substituted with halo, cyano or hydroxyl.

In another further embodiment, with respect to a compound of the invention according to Formula Ia or Ib, $R^1$ is $C_1$-$C_6$ alkyl substituted with cyano.

In one embodiment, with respect to a compound of the invention according to Formula Ia or Ib, $R^1$ is $C_3$-$C_6$ alkynyl.

In a further embodiment, with respect to a compound of the invention according to Formula Ia or Ib, $R^1$ is —CH$_2$—C≡CH.

In one embodiment, with respect to a compound of the invention according to Formula Ia or Ib, $R^1$ is $C_1$-$C_6$ alkyl.

In one embodiment, with respect to a compound of the invention according to Formula Ia or Ib, $R^1$ is Me, Et, i-Pr, or n-Pr.

In a further embodiment, with respect to a compound of the invention according to Formula Ia or Ib, $R^1$ is Me.

In one embodiment, with respect to a compound of the invention according to Formula Ia or Ib, $R^{3a}$ is H, halo, cyano, or nitro.

In another embodiment, with respect to a compound of the invention according to Formula Ia or Ib, $R^{3a}$ is $C_1$-$C_6$ alkyl.

In another embodiment, with respect to a compound of the invention according to Formula Ia or Ib, $R^{3a}$ is $C_1$-$C_6$ alkyl substituted with halo, cyano, nitro, hydroxyl, or $C_1$-$C_4$ alkoxy.

In another embodiment, with respect to a compound of the invention according to Formula Ia or Ib, $R^{3a}$ is amido.

In another embodiment, with respect to a compound of the invention according to Formula Ia or Ib, $R^{3a}$ is amido substituted with $C_1$-$C_6$ alkyl.

In one embodiment, with respect to a compound of the invention according to Formula Ia or Ib, $R^{3b}$ is halo, cyano, or nitro.

In one embodiment, with respect to a compound of the invention according to Formula Ia or Ib, m1 is 0.

In another embodiment, with respect to a compound of the invention according to Formula Ia or Ib, $R^{3b}$ is $C_1$-$C_6$ alkyl.

In another embodiment, with respect to a compound of the invention according to Formula Ia or Ib, $R^{3b}$ is $C_1$-$C_6$ alkyl substituted with halo, cyano.

In another embodiment, with respect to a compound of the invention according to Formula Ia or Ib, $R^{3b}$ is amido.

In another embodiment, with respect to a compound of the invention according to Formula Ia or Ib, $R^{3b}$ is amido substituted with $C_1$-$C_6$ alkyl.

In one embodiment, with respect to a compound of the invention according to Formula Ia or Ib, the compound of the invention is according to Formula II:

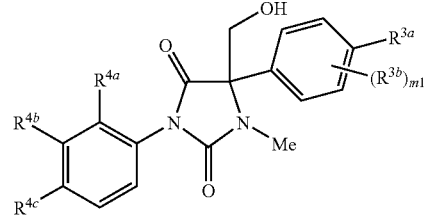

wherein $R^{3a}$, $R^{3b}$, $R^{4a}$, $R_{4b}$, $R^{4c}$, and m1 are as described in any one of the preceding paragraphs.

In one embodiment, with respect to a compound of the invention according to Formula II, $R^{4c}$ is cyano, halo or nitro.

In one embodiment, with respect to a compound of the invention according to Formula II, $R^{4c}$ is cyano.

In another embodiment, with respect to a compound of the invention according to Formula II, $R^{4b}$ is H, halo, cyano, $C_1$-$C_6$ alkyl, or $C_1$-$C_6$ haloalkyl.

In another, embodiment with respect to a compound of the invention according to Formula II, $R^{4b}$ is Cl, F, CN or CF$_3$.

In a further embodiment, with respect to a compound of the invention according to Formula II, $R^{4b}$ is CF$_3$.

In one embodiment, with respect to a compound of the invention according to Formula II, $R^{4a}$ is H, halo, cyano, $C_1$-$C_6$ alkyl, or $C_1$-$C_6$ haloalkyl.

In a further embodiment, with respect to a compound of the invention according to Formula II, $R^{4a}$ is Cl or F.

In another further embodiment, with respect to a compound of the invention according to Formula II, $R^{4a}$ is H.

In one embodiment, with respect to a compound of the invention according to Formula II, the compound of the invention is according to Formulae IIIa or IIIb:

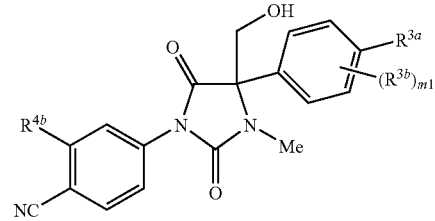

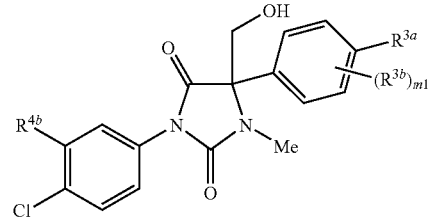

wherein $R^{3a}$, $R^{3b}$, $R^{4b}$, and m1 are as described in any one of the preceding paragraphs.

In one embodiment with respect to a compound of the invention of Formulae IIIa or IIIb, $R^{4b}$ is H, halo, cyano, $C_1$-$C_6$ alkyl, or $C_1$-$C_6$ haloalkyl.

In a preferred embodiment with respect to a compound of the invention of Formulae IIIa or IIIb, $R^{4b}$ is Cl, F, CN or CF$_3$.

In a more preferred embodiment with respect to a compound of the invention of Formula IIIa, $R^{4b}$ is CF$_3$.

In another more preferred embodiment with respect to a compound of the invention of Formula IIIb, $R^{4b}$ is Cl.

In one embodiment, with respect to a compound of the invention according to Formula II, the compound of the invention is according to Formulae IVa or IVb:

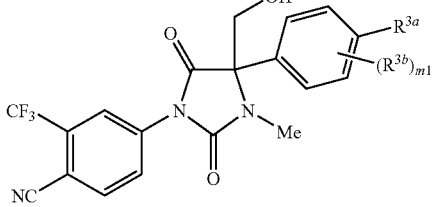
IVa

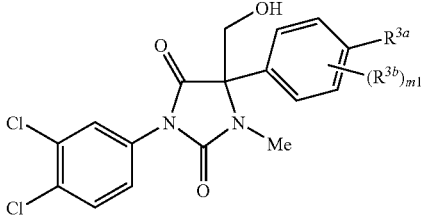
IVb wherein $R^{3a}$, $R^{3b}$, and m1 are as described in any one of the preceding paragraphs.

In one embodiment with respect to a compound of the invention of Formulae IVa or IVb, $R^{3a}$ is H, halo, cyano, $C_1$-$C_6$ alkyl, or $C_1$-$C_6$ haloalkyl.

In a preferred embodiment, with respect to a compound of the invention of Formulae IVa or IVb, $R^{3a}$ is H, Me, Cl, F, CN or $CF_3$.

In another embodiment, with respect to a compound of the invention of Formulae IVa or IVb, m1 is 1 or 2.

In another embodiment, with respect to a compound of the invention of Formulae IVa or IVb, $R^{3b}$ is halo, cyano, $C_1$-$C_6$ alkyl, or $C_1$-$C_6$ haloalkyl.

In a preferred embodiment, with respect to a compound of the invention of Formulae IVa or IVb, $R^{3b}$ is Me, Cl, F, CN or $CF_3$.

In another embodiment, with respect to a compound of the invention of Formulae IVa or IVb, m1 is 0.

In one embodiment, with respect to a compound of the invention of Formula I, the compound of the invention is according to Formulae Va, Vb, Vc or Vd:

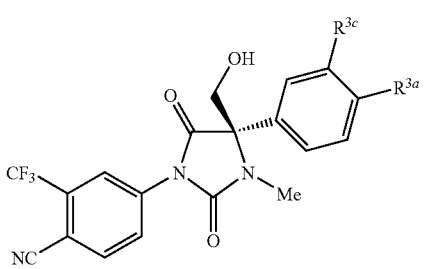
Va

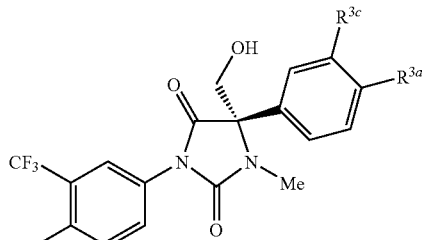
Vb

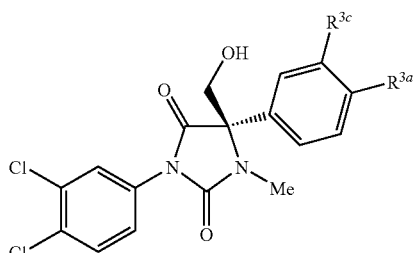
Vc

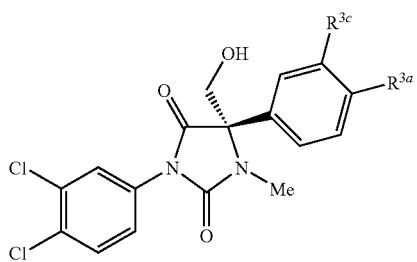
Vd wherein $R^{3a}$ is as described in any one of the preceding paragraphs;
$R^{3c}$ is H, halo, cyano, or nitro; or
$R^{3c}$ is $C_1$-$C_6$ alkyl optionally substituted with cyano, or halo; or
$R^{3c}$ is amido optionally substituted with $C_1$-$C_6$ alkyl.

In one embodiment, with respect to a compound of the invention of Formula I, the compound of the invention is according to Formula Va.

In one embodiment, with respect to a compound of the invention of Formula I, the compound of the invention is according to Formula Vb.

In one embodiment, with respect to a compound of the invention of Formula I, the compound of the invention is according to Formula Vc.

In one embodiment, with respect to a compound of the invention of Formula I, the compound of the invention is according to Formula Vd.

In one embodiment, with respect to a compound of the invention of Formulae Va, Vb, Vc or Vd, $R^{3a}$ is H, halo, or cyano; and $R^{3c}$ is H.

In one embodiment, with respect to a compound of the invention of Formulae Va, Vb, Vc or Vd, $R^{3a}$ is H, CN, Cl, or F and $R^{3c}$ is H.

In one embodiment, with respect to a compound of the invention of Formulae Va, Vb, Vc or Vd, $R^{3a}$ is H; and $R^{3c}$ is H, halo, $C_1$-$C_6$ alkyl, $C_1$-$C_6$ haloalkyl, or cyano.

In another embodiment, with respect to a compound of the invention of Formulae Va, Vb, Vc or Vd, $R^{3a}$ is H; and $R^{3c}$ is CN, Cl, F, Me or $CF_3$.

In a further embodiment, with respect to a compound of the invention of Formulae Va, Vb, Vc or Vd, each $R^{3a}$ and $R^{3c}$ is H.

In a preferred embodiment, the compound of the invention is according to Formula Vb wherein $R^{3a}$ and $R^{3c}$ are H.

In another preferred embodiment, the compound of the invention is according to Formula Vd, wherein $R^{3a}$ and $R^{3c}$ are H.

In one embodiment, the compound of the invention is selected from the compounds of the invention listed in Table 1.

In a further embodiment, the compounds of the invention are those of Formula (VI):

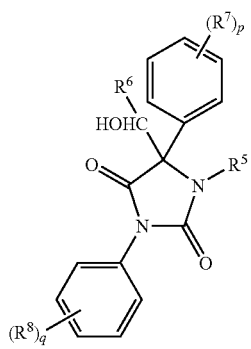

(VI)

wherein:
$R^5$ is H, $C_{1-6}$ alkyl, $C_{2-6}$ alkenyl, $C_{2-6}$ alkynyl, or
$R^5$ is $C_{1-4}$ alkyl substituted with a cyano group or one or more halo groups;
$R^6$ is H or $C_{1-4}$ alkyl;
$R^7$ is halo, cyano, $C_{1-4}$ alkyl, or $C_{1-4}$ perfluoroalkyl;
$R^8$ is halo, cyano, nitro, $C_{1-4}$ alkyl, or $C_{1-4}$ perfluoroalkyl;
p is 0, 1, or 2;
q is 1, 2, or 3;
when p is 2 then each $R^7$ is the same or different;
when q is 2 or 3 then each $R^8$ is the same or different; and
pharmaceutically acceptable esters thereof.

In one embodiment, it is preferred that $R^6$ is H.
In another aspect, it is preferred that $R^5$ is methyl or ethyl.
It is further preferred that $R^5$ is propynyl.
In one aspect, it is preferred that p is 1. In this aspect, it is preferred that $R^7$ is Cl or F.
When p is 1, it is preferred that $R^7$ is in the para position.
In another aspect, it is preferred that p is 0.
It is generally preferred that any perfluoroalkyl group is a trifluoromethyl group.
In another aspect, it is preferred that q is 2. In this embodiment, it is preferred that each $R^8$ is selected from F, Cl, cyano, trifluoromethyl, and methyl.
When q is 2, it is preferred that one $R^8$ substituent is in the para position and the other is at the meta position.
When q is 2, in one embodiment, it is preferred that each $R^8$ is Cl. In another embodiment, it is preferred that each $R^8$ is selected from cyano and trifluoromethyl, and it is particularly preferred that a first $R^8$ is p-cyano and the second $R^8$ is m-trifluoromethyl.
A particularly preferred pharmaceutically acceptable ester is the phosphate ester.
A particularly preferred pharmaceutically acceptable ester is the hemi-succinate ester.
A particularly preferred pharmaceutically acceptable ester is the valinate ester.

In a another further aspect the present invention provides a compound of the invention of Formula (VII):

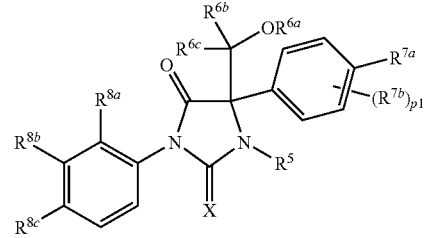

(VII)

wherein
X is O;
$R^5$ is H, $C_1$-$C_6$ alkyl, $C_3$-$C_6$ alkenyl, or $C_3$-$C_6$ alkynyl, each of which may be unsubstituted or substituted with cyano, one or more halo;
$R^{6a}$ is H, or a phosphoric ester or derivative thereof, or a carboxylic ester, and preferably $P(O)(OH)_2$, $C(=O)$—$(CH_2)_2$—$CO_2H$, or —$C(=O)CH(NH_3Cl)iPr$;
$R^{6b}$ is H;
$R^{6c}$ is independently selected from H, and $C_1$-$C_6$ alkyl;
$R^{7a}$ is H, halo, cyano, $C_1$-$C_4$ alkyl, which may be unsubstituted or substituted with one or more halo;
$R^{7b}$ is halo, cyano, or $C_1$-$C_4$ alkyl, which may be unsubstituted or substituted with halo; each $R^{8a}$, and $R^{8b}$ is independently H, halo, cyano, $C_1$-$C_4$ alkyl, each of which may be unsubstituted or substituted by one or more halo;
$R^{8c}$ is halo, cyano or nitro; and
$p_1$ is 0, 1, or 2.

In a particular aspect $R^{6c}$ is selected from H and $C_1$-$C_4$ alkyl.
In a particular aspect $R^{7a}$ is selected from H, halo, and cyano.
In a particular aspect $R^{7a}$ is $C_1$-$C_4$ alkyl.
In a particular aspect $R^{7a}$ is $C_1$-$C_4$ alkyl, substituted by one or more halo.
In a particular aspect $R^{7a}$ is $CF_3$.
In a particular aspect $R^{7b}$ is selected from halo, cyano, or $C_1$-$C_4$ alkyl, which may be unsubstituted or substituted by one or more halo.
In a particular aspect each $R^{8a}$, and $R^{8b}$ is independently H, halo, cyano or $C_1$-$C_4$ alkyl, which may be unsubstituted or substituted by one or more halo.
In a particular aspect $R^{6c}$ is H.
In a particular aspect $R^{6a}$ is H.
In a particular aspect $R^{6a}$ is $P(O)(OH)_2$.
In a particular aspect $R^5$ is methyl or ethyl.
In a further particular aspect $R^5$ is propynyl.
In a particular aspect $p_1$ is 0.
In a particular aspect $R^{7a}$ is Cl or F.
In a particular aspect $R^{7a}$ is H.
In further particular aspects where an alkyl group is substituted by halogen, the halogen is F. In a further particular aspect the substituted alkyl group is a trifluoromethyl group.
In a particular aspect each $R^{8a}$, $R^{8b}$ is selected from F, Cl, cyano, nitro, trifluoromethyl, and methyl, and $R^{8c}$ is selected from F, Cl, cyano and nitro
In a particular aspect $R^{8a}$ is H.
In a particular aspect $R^{8b}$ and $R^{8c}$ are Cl. In another embodiment, $R^{8b}$ and $R^{8c}$ are selected from cyano and trifluoromethyl, and in a particular embodiment, $R^{8c}$ is cyano and the $R^{8b}$ is trifluoromethyl.

Preferred compounds of the invention are selected from:
4-[2,5-Dioxo-4-(hydroxymethyl)-3-methyl-4-phenylimidazolidin-1-yl]-2-trifluoromethylbenzonitrile;

4-[2,5-Dioxo-4-(1-hydroxypropyl)-3-methyl-4-phenylimidazolidin-1-yl]-2-trifluoromethylbenzonitrile;

4-[2,5-Dioxo-4-(1-hydroxyethyl)-3-methyl-4-phenylimidazolidin-1-yl]-2-trifluoromethylbenzonitrile;

4-[2,5-Dioxo-4-(4-fluorophenyl)-4-(hydroxymethyl)-3-methylimidazolidin-1-yl]-2-trifluoromethylbenzonitrile;

4-[4-(4-Chlorophenyl)-2,5-dioxo-4-hydroxymethyl-3-methylimidazolidin-1-yl]-2-trifluoromethylbenzonitrile;

4-[2,5-Dioxo-4-(4-fluorophenyl)-4-hydroxymethyl-3-(2-propynyl)imidazolidin-1-yl]-2-trifluoromethylbenzonitrile;

4-[4-(3-Chlorophenyl)-2,5-dioxo-4-hydroxymethyl-3-methylimidazolidin-1-yl]-2-trifluoromethylbenzonitrile;

(S)-4-[2,5-Dioxo-4-(hydroxymethyl)-3-methyl-4-phenylimidazolidin-1-yl]-2-trifluoromethylbenzonitrile;

(R)-4-[2,5-Dioxo-4-(hydroxymethyl)-3-methyl-4-phenylimidazolidin-1-yl]-2-trifluoromethylbenzonitrile;

4-[2,5-Dioxo-3-ethyl-4-(hydroxymethyl)-4-phenylimidazolidin-1-yl]-2-trifluoromethylbenzonitrile;

4-[4-(4-Cyanophenyl)-2,5-dioxo-4-hydroxymethyl-3-methylimidazolidin-1-yl]-2-trifluoromethylbenzonitrile;

4-[4-(3-Cyanophenyl)-2,5-dioxo-4-hydroxymethyl-3-methylimidazolidin-1-yl]-2-trifluoromethylbenzonitrile;

4-[2,5-Dioxo-4-hydroxymethyl-3-methyl-4-(3-trifluoromethylphenyl)imidazolidin-1-yl]-2-trifluoromethylbenzonitrile;

1-(3,4-Dichlorophenyl)-4-hydroxymethyl-3-methyl-4-phenylimidazolidine-2,5-dione;

4-[2,5-Dioxo-4-(hydroxymethyl)-3-(1-methylethyl)-4-phenylimidazolidin-1-yl]-2-trifluoromethylbenzonitrile;

4-[3-Cyanomethyl-2,5-dioxo-4-(hydroxymethyl)-4-phenylimidazolidin-1-yl]-2-trifluoromethylbenzonitrile;

4-[2,5-Dioxo-4-(hydroxymethyl)-4-phenyl-3-(1-propynyl)imidazolidin-1-yl]-2-trifluoromethylbenzonitrile;

4-[2,5-Dioxo-4-hydroxymethyl-4-phenylimidazolidin-1-yl]-2-trifluoromethylbenzonitrile;

4-[2,5-Dioxo-4-hydroxymethyl-3-methyl-4-(3-methylphenyl)imidazolidin-1-yl]-2-trifluoromethylbenzonitrile;

4-[4-(2-Chlorophenyl)-2,5-dioxo-4-hydroxymethyl-3-methylimidazolidin-1-yl]-2-trifluoromethylbenzonitrile;

[1-(4-Cyano-3-trifluoromethylphenyl)-2,5-dioxo-3-methyl-4-phenylimidazolidin-4-yl]methyl dihydrogen phosphate;

4-[1-(4-Cyano-3-trifluoromethylphenyl)-2,5-dioxo-3-methyl-4-phenylimidazolidin-4-yl]methoxy-4-oxobutanoic acid; and (2S)-1-[1-(4-Cyano-3-trifluoromethylphenyl)-2,5-dioxo-3-methyl-4-phenylimidazolidin-4-yl]methoxy-3-methyl-1-oxobutan-2-aminium chloride.

4-[1-(4-Cyano-3-trifluoromethylphenyl)-2,5-dioxo-3-methyl-4-phenylimidazolidin-4-yl]methoxy-4-oxobutanoic acid;

(S)-(1-(4-cyano-3-(trifluoromethyl)phenyl)-3-methyl-2,5-dioxo-4-phenylimidazolidin-4-yl)methyl dihydrogen phosphate;

(S)-4-((1-(4-cyano-3-(trifluoromethyl)phenyl)-3-methyl-2,5-dioxo-4-phenylimidazolidin-4-yl)methoxy)-4-oxobutanoic acid.

In one embodiment the compound of the invention according to any one of the embodiments herein is not an isotopic variant.

In one embodiment, with respect to Formula I, the compound is selected from the compounds listed in Table 1.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate.

In one aspect a compound of the invention according to any one of the embodiments herein described is a solvate of a pharmaceutically acceptable salt.

While specified groups for each embodiment have generally been listed above separately, a compound of the invention includes one in which several or each embodiment in the above formula, as well as other formulae presented herein, is selected from one or more of particular members or groups designated respectively, for each variable. Therefore, this invention is intended to include all combinations of such embodiments within its scope.

The present invention provides the use of a compound of the invention as defined above in the prophylaxis or treatment of cachexia.

Pharmaceutical Compositions

When employed as pharmaceuticals, a compound of the invention is typically administered in the form of a pharmaceutical composition. Such compositions can be prepared in a manner well known in the pharmaceutical art and comprise at least one active compound. Generally, a compound of the invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms.

The pharmaceutical compositions of this invention can be administered by a variety of routes including oral, rectal, transdermal, subcutaneous, intra-articular, intravenous, intramuscular, and intranasal. Depending on the intended route of delivery, the compounds of the invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the active compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate may be added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture may be filled into 250 mg capsules (125 mg of active compound per capsule).

Formulation 3—Liquid

A compound of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added with stirring. Sufficient water is then added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The present invention relates to novel imidazolidine compounds which modulate the activity of the androgen receptors. These compounds may be of use in the treatment and/or prevention of a number of disorders as will be discussed in further detail below. It will be appreciated by a person of skill in the art that the activity of a compound of the invention as an antagonist (complete or partial) or agonist (complete or partial) represents a continuous spectrum. Therefore, whilst some compounds will be clearly agonists or clearly antagonists, some compounds will exhibit both agonistic and antagonistic activity. These compounds with mixed activities will potentially be of use in the treatment of a variety of disorders. Provided in the example herein are details of how the relative activities of a compound of the invention may be identified and classified as agonists, antagonists or mixed agonists/antagonists. It is therefore clear that it is well within the ability of a person of skill in the art using their common general knowledge, combined with the information provided in the examples herein, to identify whether a particular compound of the invention is an agonist, antagonist or mixed agonist/antagonist and thus the appropriate uses of said compound.

A compound of the invention may show good absorption, good half-life, good solubility, good bioavailability, low protein binding affinity, less drug-drug interaction, and good metabolic stability. In a particular aspect, a compound of the present invention exhibits unexpected significant improvements in pharmacological properties, in particular improved bioavailability. Where a compound of the invention exhibit any one or more of these improvements, this may have an effect on its use in the conditions described herein. For example, where a compound of the invention exhibits an improved bioavailability it would be expected that a compound of the invention could be administered at a lower dose, thus reducing the occurrence of any possible undesired side effects. Similarly, improvements in the other properties listed above will also confer advantages in the potential uses of a compound of the invention.

The present compounds are useful as therapeutic agents for the treatment of conditions that are causally related or attributable to an alteration in levels of circulating androgens in mammals. Accordingly, in one aspect, the present invention provides a compound of the invention for use in medicine.

In one embodiment, the present invention provides a compound of the invention for use in the prevention and/or treatment of age-related diseases including, but not limited to sarcopenia, conditions of cachexia and muscle loss induced by diseases including, but not limited to, cancer and AIDS, or induced by thermal burns or long term immobilisation; and bone and joint diseases, such as osteoporosis, reduction in libido and sexual dysfunction, or anemia. In a particular aspect of this embodiment, a compound of the invention is an agonist or mixed agonist/antagonist of the AR.

In a further embodiment, the present invention provides a method of treatment and/or prevention of age-related diseases including, but not limited to sarcopenia, conditions of cachexia and muscle loss induced by diseases including, but not limited to, cancer and AIDS, bone and joint diseases, such as osteoporosis, reduction in libido and sexual dysfunction, or anemia, said method comprising administering to a subject in need thereof a therapeutically effective amount of a compound of the invention or pharmaceutical composition of the invention. In a particular aspect of this embodiment, the compound of the invention is agonist or mixed agonist/antagonist of the AR or the pharmaceutical composition comprises an agonist or mixed agonist/antagonist of the AR.

In one embodiment, the present invention provides a compound of the invention for use in the prevention and/or treatment of androgen-dependent tumors, such as prostate cancer or hyperplasia. In a particular aspect of this embodiment, a compound of the invention is an antagonist of the AR.

In a further embodiment, the present invention provides a method of treatment and/or prevention of androgen-dependent tumors, such as prostate cancer or hyperplasia, said method comprising administering to a subject in need thereof a therapeutically effective amount of a compound of the invention or pharmaceutical composition of the invention. In a particular aspect of this embodiment, the compound of the invention is antagonist of the AR or the pharmaceutical composition comprises an antagonist of the AR.

In one aspect the present invention provides a compound of the invention which is androgen receptor antagonist according to any one of Formulae I-VII above wherein the $K_{Schild}$ value is below 1 µM for use in the prevention or treatment of androgen-dependent tumors, such as prostate cancer or hyperplasia.

In one aspect the present invention provides a method of treatment and/or prevention of androgen-dependent tumors, such as prostate cancer or hyperplasia, said method comprising administering to a subject in need thereof a therapeutically effective amount of a compound of the invention according to any one of Formulae I-VII above, wherein said compound of the invention is an androgen receptor antagonist, wherein the $K_{Schild}$ value is below 1 µM.

In one aspect the present invention provides a compound of the invention which is androgen receptor agonist or mixed agonist/antagonist according to any one of Formulae I-VII above wherein the $EC_{50}$ and $K_{Schild}$ values are both below 1 µM for use in the prevention or treatment of age-related diseases including, but not limited to sarcopenia, conditions of cachexia and muscle loss induced by diseases including, but not limited to, cancer and AIDS, and bone and joint diseases, such as osteoporosis, reduction in libido and sexual dysfunction, or anemia.

In one aspect the present invention provides a method of treatment and/or prevention of age-related diseases including, but not limited to sarcopenia, conditions of cachexia and muscle loss induced by diseases including, but not limited to, cancer and AIDS, and bone and joint diseases, such as osteoporosis, reduction in libido and sexual dysfunction, or anemia, said method comprising administering to a subject in need thereof a therapeutically effective amount of a compound of the invention according to any one of Formulae I-VII above, wherein said compound of the invention is an androgen receptor agonist or mixed agonist/antagonist, wherein the $EC_{50}$ and $K_{Schild}$ values are both below 1 µM.

Transdermal doses are generally selected to provide similar or lower blood levels than are achieved using injection doses.

When used to prevent a sarcopenia condition, the compounds of this invention will be administered to a patient at risk for developing the condition, typically on the advice and under the supervision of a physician, at the dosage levels described above. Patients at risk for developing a particular condition generally include elderly people, whose muscle mass decline results in the loss of motility or more difficult movements.

When used to prevent an osteoporosis condition, the compounds of this invention will be administered to a patient at risk for developing the condition, typically on the advice and under the supervision of a physician, at the dosage levels described above. Patients at risk for developing a particular condition generally include elderly people, whose bone density reduction may cause increased fracture risks.

When used to prevent a cachexia condition resulting from a primary ailment, for example from, but not limited to, cancer, HIV, stable chronic obstructive pulmonary disease (COPD), congestive heart failure, or late stage renal failure, the compounds of this invention will be administered to a patient, typically on the advice and under the supervision of a physician, at the dosage levels described above. Typical patients generally include patients being treated for cancer, HIV or AIDS.

A compound of the invention can be administered as the sole active agent or it can be administered in combination with other therapeutic agents, including other compounds that demonstrate the same or a similar therapeutic activity, and that are determined to be safe and efficacious for such combined administration. In a specific embodiment, co-administration of two (or more) agents allows for treatment of a primary condition, and its associated side effects.

In one embodiment, a compound of the invention is co-administered with another therapeutic agent for the treatment and/or prevention of sarcopenia condition; particular agents include, but are not limited to testosterone, corotinoids, androgens, SARMs and insulin like growth factor 1.

In one embodiment, a compound of the invention is administered with another therapeutic regimen for the treatment and/or prevention of sarcopenia condition; particular regimens include, but are not limited to physical exercise alone or in combination with creatinine monohydrate or with dietary proteins.

In one embodiment, a compound of the invention is co-administered with another therapeutic agent for the treatment and/or prevention of osteoporosis; particular agents include, but are not limited to bisphosphonates (sodium alendronate, reisedronate, ibendronate, or zoledronic acid), teriparatide, strontium ranelate, hormone replacement, (raloxifene), calcium or vitamin D supplement.

In one embodiment, a compound of the invention is co-administered with another therapeutic agent for the treatment and/or prevention of cachexia; particular agents include but are not limited to appetite stimulants/anti emetics (for example but without limitation Megestrol acetate, tetrahydrocannabinol), ACE inhibitors, Beta blockers, anabolic agents (for example but without limitation oxandrolone, nandrolone, ghrelin).

In one embodiment, a compound of the invention is co-administered with another therapeutic agent for the treatment and/or prevention of HIV induced cachexia; particular agents include but are not limited to nucleotide analog reverse transcriptase inhibitors (NtARTIs or NtRTIs) (for example but without limitation Tenofovir®, Adefovir®), non-nucleoside reverse transcriptase inhibitors (NNRTIs) (for example but without limitation Efavirenz®, Nevirapine®, Delavirdine®, Etravirine®), protease inhibitors (for example but without limitation Saquinavir®, Ritonavir®, Indinavir®, Nelfinavir®, Amprenavir®, Lopinavir®, Atazanavir®, Fosamprenavir®, Tipranavir®, Darunavir®), entry inhibitors (for example but without limitation Maraviroc®, Enfuvirtide®) or integrase inhibitors (for example but without limitation raltegravir).

In one embodiment, a compound of the invention is co-administered with another therapeutic agent for the treatment and/or prevention of congestive heart failure induced cachexia; particular agents include but are not limited to oral loop diuretics (furosemide, torsemide or bumetamide), beta-blockers (bisoprolol, carvedilol, and sustained-release metoprolol), ACE inhibitors (Captopril, Zofenopril, Enalapril, Ramipril, Quinapril, Perindopril, Lisinopril, Benazepril, or Fosinopril), angiotensin II receptor antagonists (Candesartan), or vasodilatators.

In one embodiment, a compound of the invention is co-administered with another therapeutic agent for the treatment and/or prevention of late stage renal failure induced cachexia; particular agents include but are not limited to ACE inhibitors (Captopril, Zofenopril, Enalapril, Ramipril, Quinapril, Perindopril, Lisinopril, Benazepril, or Fosinopril), angiotensin II receptor antagonists (Candesartan), vitamin D3, or calcium associated to phosphate binders.

By co-administration is included any means of delivering two or more therapeutic-agents to the patient as part of the same treatment regime, as will be apparent to the skilled person. Whilst the two or more agents may be administered simultaneously in a single formulation this is not essential. The agents may be administered in different formulations and at different times.

General Synthetic Procedures

General

The compounds of the invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Second Edition, Wiley, New York, 1991, and references cited therein.

The following methods are presented with details as to the preparation of representative compounds that have been listed hereinabove. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 μm). Thin layer chromatography is carried out using pre-coated silica gel F-254 plates (thickness 0.25 mm) $^1$H NMR spectra are recorded on a Bruker DPX 400 NMR spectrometer (400 MHz). Chemical shifts ($\delta$) for $^1$H NMR spectra are reported in parts per million (ppm) relative to tetramethylsilane ($\delta 0.00$) or the appropriate residual solvent peak, i.e. CHCl$_3$ ($\delta 7.27$), as internal reference. Multiplicities are given as singlet (s), doublet (d), triplet (t), quartet (q), multiplet (m) and broad (br). Coupling constants (J) are given in Hz. Electrospray mass spectra (MS) are obtained on a Micromass platform LCMS spectrometer. Column used for all LCMS analysis: Chromolith Performance RP-18 100 mm×3 mm (Merck AG). All the methods are using the following gradient:

Solvent A: MeCN; solvent B: H$_2$O, both solvents contain 0.1% formic acid.

Gradient: 100% B to 0% B from 0 to 3.5 min; 0% B from 3.5 to 4.5 min; 0% to 100% B from 4.5 to 4.6 min; 100% B from 4.6 to 5 min. Flow rate: 2.5 mL/min.

List of abbreviations used in the experimental section:

| | |
|---|---|
| DCM: | Dichloromethane |
| DiPEA: | N,N-diisopropylethylamine |
| MeCN | Acetonitrile |
| BOC | tert-Butyloxycarbonyl |
| DMF | N,N-dimethylformamide |
| TFA | Trifluoroacetic acid |
| NMR | Nuclear Magnetic Resonnance |
| DMSO | Dimethylsulfoxide |
| DPPA | Diphenylphosphorylazide |
| LCMS | Liquid Chromatography coupled to Mass Spectrometry |
| ppm | part-per-million |
| Fr | frontal ratio |
| Rt | retention time |
| s | singlet |
| br s | broad singlet |
| m | multiplet |
| d | doublet |
| Mp | Melting point |
| rt | Room temperature |
| Rt | Retention time |
| TEA | Triethylamine |

GENERAL PROCEDURES

General scheme:

Compounds of the invention may be prepared according to the following procedures:

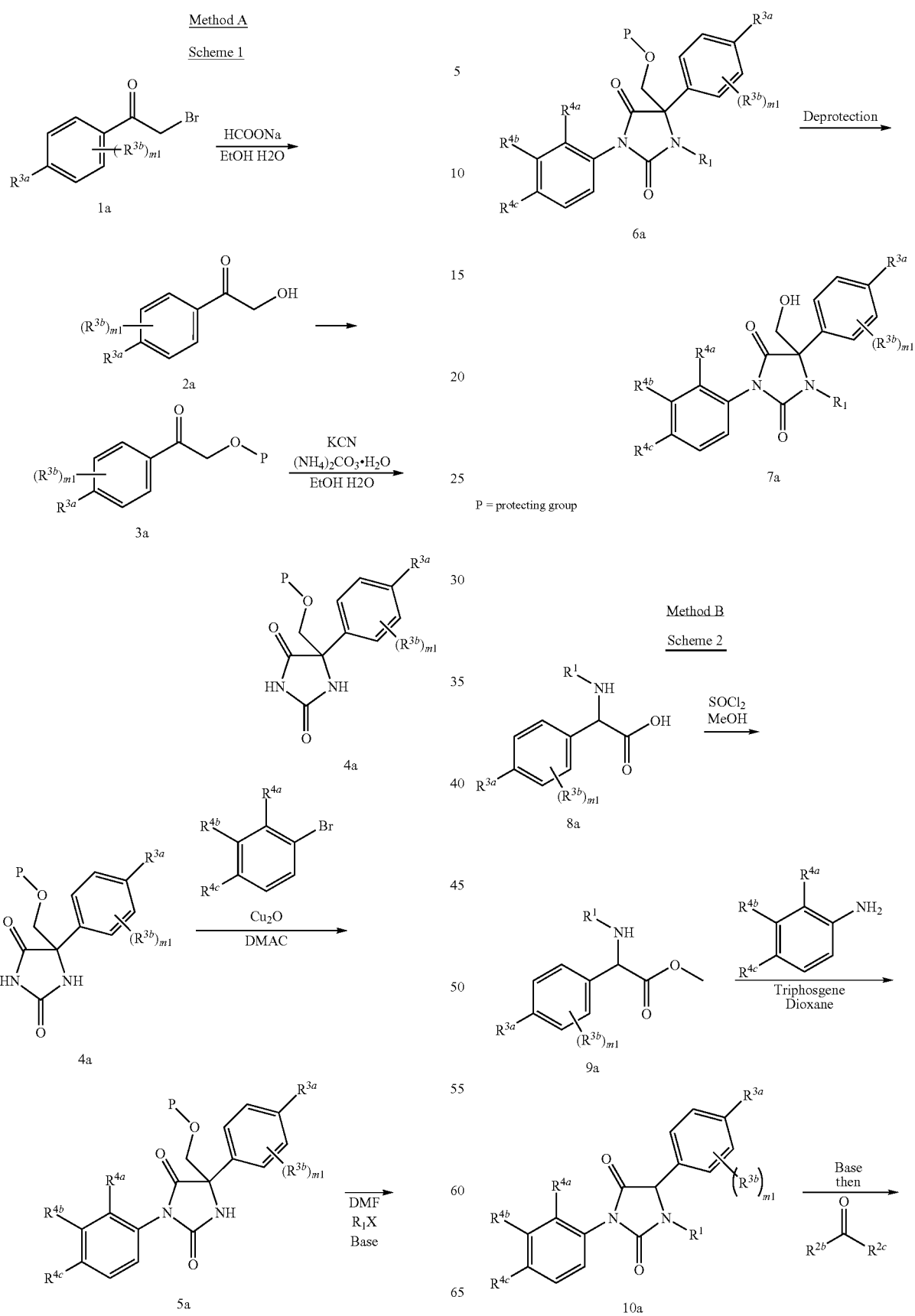

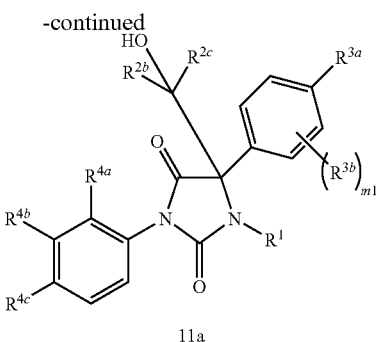

11a

Example 1

4-[2,5-Dioxo-4-hydroxymethyl-3-methyl-4-phenylimidazolidin-1-yl]-2-trifluoromethylbenzonitrile (Method A)

Step 1: 1-Phenyl-2-(2-propenyloxy)ethanone

This compound is prepared from 2-hydroxy-1-phenylethanone, according to the procedure used by G. A. Molander and J. A. McKie on 1-hydroxy-2-butanone, J. Org. Chem. (1995), 60, 872-882.
Protection step (optional):
1-hydroxy-2-butanone can be protected by a variety of well known groups according to routine procedures well known by the man of skill in the art. For example, 2-(tert-Butyl-dimethyl-silanyloxy)-1-phenyl-ethanone is obtained quantitatively by mixing 1-hydroxy-2-butanone, tBDMSCl, and imidazole in DMF (see ref 10). This intermediate is then used as described in the following steps.

Step 2: 4-Phenyl-2-(propenyloxy)imidazolidine-2,5-dione 0.775 g of 1-phenyl-2-(2-propenyloxy)ethanone, 0.575 g of potassium cyanide and 1.6 g of ammonium carbonate are heated to 55° C. for 3 hours in 23 mL of a 50/50 ethanol/water mixture. The reaction mixture is diluted with water and extracted with ethyl acetate. The organic solution is washed with a saturated aqueous sodium chloride solution, then dried over sodium sulfate and evaporated to yield the desired product (whitish yellow solid).
TLC: Fr=0.42 (heptane/ethyl acetate 50/50)
δ $^1$H NMR (CD$_3$OD): 3.68 (d, 1H); 4.13 (m, 3H); 4.22 (d, 1H); 4.92 (s, 2H); 5.22 (dd, 1H); 5.34 (dd, 1H); 5.95 (ddt, 1H); 7.45 (m, 3H); 7.64 (d, 2H)
LCMS: (Rt=5.79 min): 288+ (MH, MeCN$^+$)

Step 3: 4-[2,5-Dioxo-4-phenyl-4-[(2-propenyloxy)methyl]imidazolidin-1-yl]-2-trifluoromethylbenzonitrile To a solution of 0.47 g of 4-phenyl-2-(propenyloxy)imidazolidine-2,5-dione in 30 mL dimethylacetamide is added 0.28 g of copper (I) oxide and 0.81 g of 4-bromo-2-trifluoromethylbenzonitrile. The mixture is heated at 160° C. for 3 hours. At rt, the mixture is diluted with a 50% aqueous solution of ammonia and extracted with ethyl acetate. The organic layer is dried over sodium sulfate, filtered and evaporated. The crude product is purified by chromatography over silica gel while eluting with 70/30 heptane/ethyl acetate to provide the desired product.

TLC: Fr=0.30 (heptane/ethyl acetate 70/30)
δ $^1$H NMR (CDCl$_3$): 3.86 (d, 1H); 4.14 (sl, 2H); 4.27 (d, 1H); 5.28 (d, 1H); 5.32 (d, 1H); 5.89 (ddt, 1H); 7.52 (m, 3H); 7.70 (m, 2H); 7.98 (m, 2H); 8.14 (m, 1H)
LCMS: (Rt=6.91 min): 414−(M−H−)

Step 4: 4-[2,5-Dioxo-3-methyl-4-phenyl-4-[(2-propenyloxy)methyl]imidazolidin-1-yl]-2-trifluoromethylbenzonitrile To a solution of 0.86 g of 4-[2,5-dioxo-4-phenyl-4-[(2-propenyloxy)methyl]imidazolidin-1-yl]-2-trifluoromethylbenzonitrile and 0.26 mL of iodomethane in 30 mL of DMF is added 430 mg of potassium carbonate. The mixture is stirred at rt for 5 hours, evaporated to dryness, diluted with water and extracted with ethyl acetate. The organic layer is dried over magnesium sulfate, filtered and evaporated. The crude product is purified by chromatography over silica gel while eluting with 70/30 heptane/ethyl acetate mixture to provide the desired product.
TLC: Fr=0.37 (heptane/ethyl acetate 70/30)
δ $^1$H NMR (CDCl$_3$): 3.07 (s, 3H); 3.98 (d, 1H); 4.14 (br s, 2H); 4.44 (d, 1H); 5.28 (d, 1H); 5.32 (d, 1H); 5.87 (ddt, 1H); 7.39 (m, 2H); 7.49 (m, 3H); 7.92 (d, 1H); 8.00 (d, 1H); 8.13 (m, 1H)
LCMS: (Rt=7.11 min) 471+ (MH, MeCN+)

Step 5: 4-[2,5-Dioxo-4-hydroxymethyl-3-methyl-4-phenylimidazolidin-1-yl]-2-trifluoromethyl-benzonitrile To a solution of 0.52 g of 4-[2,5-dioxo-3-methyl-4-phenyl-4-[(2-propenyloxy)methyl]imidazolidin-1-yl]-2-trifluoromethylbenzonitrile in 40 mL of dichloromethane is added 2 mL of trifluoroborane-dimethylsulfide complex in 10 mL of dichloromethane. The mixture is stirred at rt for 3 hours and poured into a saturated aqueous sodium bicarbonate solution and extracted with ethyl acetate. The organic layer is dried over magnesium sulfate, filtered and evaporated. The crude product is purified by chromatography over silica gel while eluting with 70/30 heptane/ethyl acetate mixture to provide the desired product.
Mp=160° C.
TLC: Fr=0.33 (heptane/ethyl acetate 50/50)
δ $^1$H NMR (CDCl$_3$): 3.09 (s, 3H); 4.18 (d, 2H); 4.73 (d, 1H); 7.38 (m, 2H); 7.50 (m, 3H); 7.93 (d, 1H); 8.02 (d, 1H); 8.17 (m, 1H)
LCMS: (Rt=6.53 min): 358−(M−CH$_2$OH−)

Examples 2 & 3

4-[2,5-Dioxo-4-(1-hydroxypropyl)-3-methyl-4-phenylimidazolidin-1-yl]-2-trifluoromethyl-benzonitrile (Method B)

Step 1: Methyl 2-methylamino-2-phenylacetate 6.63 mL of thionyl chloride are slowly added to a solution of 1.5 g of 2-methylamino-2-phenylacetic acid in 100 mL of methanol. The mixture is heterogenous and becomes limpid after two hours stirring. The mixture is stirred for 48 h at rt then the solvent is evaporated to dryness. The crude product is diluted with an aqueous sodium bicarbonate solution and extracted with ethyl acetate. The organic phases are washed with water then brine, and dried over magnesium sulfate, filtered and evaporated to provide the desired product, which is used as such for the next step.

TLC: Fr=0.56 (dichloromethane/methanol 90/10)

δ $^1$H NMR (CDCl$_3$): 1.96-1.99 (br s, 1H); 2.43 (s, 3H); 3.73 (s, 3H); 4.30 (s, 1H); 7.31-7.42 (m, 5H)

Step 2: 4-[2,5-Dioxo-3-methyl-4-phenylimidazolidin-1-yl]-2-trifluoromethyl-benzonitrile To a solution of 1.26 g of triphosgene in 20 mL of anhydrous toluene is added slowly a solution of 1.18 g of 4-amino-2-trifluoromethylbenzonitrile in 16 mL of anhydrous dioxan. The mixture is refluxed for 1.5 hour. After cooling at rt the mixture is evaporated to dryness. To this crude product diluted with 50 mL of anhydrous THF is added 1.13 g of methyl 2-methylamino-2-phenylacetate in 10 mL of THF. The mixture is stirred at rt for 30 min. 1.96 mL of TEA is added, the mixture is refluxed for 1.5 hour and stirred at rt for 16 h then evaporated to dryness. The crude product is diluted with an aqueous solution of sodium bicarbonate and extracted with ethyl acetate. The organic phases are washed with water then brine, and dried over magnesium sulfate, filtered and evaporated. The crude product is crystallised in ethyl acetate, filtered and rinsed with ethyl ether to provide the desired product.

TLC: Fr=0.67 (dichloromethane/ethyl ether 90/10)

δ $^1$H NMR (CDCl$_3$): 3.06 (s, 3H); 5.06 (s, 1H); 7.35-7.39 (m, 2H); 7.48-7.56 (m, 3H); 7.96 (d, 1H); 8.03 (dd, 1H); 8.18 (d, 1H)

LCMS: (rt=2.91 min, apolar method): not ionizable

Step 3: 4-[2,5-Dioxo-4-(1-hydroxypropyl)-3-methyl-4-phenylimidazolidin-1-yl]-2-trifluoromethylbenzonitrile To a solution of 200 mg of 4-[2,5-dioxo-3-methyl-4-phenylimidazolidin-1-yl]-2-trifluoromethylbenzonitrile in 4 mL of anhydrous THF cooled to –78° C. is added slowly 0.64 mL of lithium bis(trimethylsilyl)amide 20% in hexane. The solution becomes dark brown. The mixture is stirred at –78° C. for 10 min. Then 121 μL of propanaldehyde are slowly added, the solution becomes dark red. The addition of another 121 μL of propanaldehyde leads to the total discoloration of the mixture. The mixture is stirred at –78° C. for 30 min and the reaction is quenched at –78° C. with an aqueous solution of ammonium chloride. The mixture is warmed at rt and the aqueous phase is extracted with ethyl acetate. The organic phases are washed with water then brine, and dried over magnesium sulfate, filtered and evaporated. The crude product is purified by chromatography on silica gel while eluting with 1/1 to 0/1 heptane/dichloromethane mixture then 99/1 to 95/5 dichloromethane/ethyl ether mixtures, to afford two diastereomers: isomer A and isomer B.

Analytical data for isomer A:

TLC: Fr=0.45 (dichloromethane/ethyl ether 9/1)

δ $^1$H NMR (CDCl$_3$): 1.19 (t, 3H); 1.48-1.63 (m, 1H); 1.65-1.78 (m, 1H); 3.26 (s, 3H); 4.70-4.77 (m, 1H); 7.46-7.62 (m, 5H); 7.93 (d, 1H); 7.99 (d, 1H); 8.13 (s, 1H)

LCMS: (Rt=3.47 min): 358–(M–CH$_3$CH$_2$CHOH)–

Analytical data for isomer B:

TLC: Fr=0.36 (dichloromethane/ethyl ether 9/1)

δ $^1$H NMR (CDCl$_3$): 1.18 (t, 3H); 1.42-1.55 (m, 1H); 1.72-1.84 (m, 1H); 3.08 (s, 3H); 4.63-4.70 (m, 1H); 7.39-7.55 (m, 5H); 7.95 (d, 1H); 8.02 (d, 1H); 8.15 (s, 1H)

LCMS: (Rt=3.46 min): 358–(M–CH$_3$CH$_2$CHOH)–

Examples 4 & 5

4-[2,5-Dioxo-4-(1-hydroxyethyl)-3-methyl-4-phenylimidazolidin-1-yl]-2-trifluoromethyl-benzonitrile 4-[2,5-Dioxo-4-(1-hydroxyethyl)-3-methyl-4-phenylimidazolidin-1-yl]-2-trifluoromethylbenzonitrile is obtained by using the same protocol as used for examples 2 & 4 starting from 4-[2,5-dioxo-3-methyl-4-phenylimidazolidin-1-yl]-2-trifluoromethylbenzonitrile by using acetaldehyde instead of propionaldehyde. The crude product is purified by chromatography on silica gel while eluting with 1/1 to 0/1 heptane/dichloromethane mixture then 99/1 to 95/5 dichloromethane/ethyl ether mixture, to afford two diastereomers: isomer C And isomer D.

Analytical data for isomer C:

TLC: Fr=0.32 (dichloromethane/ethyl ether/NH4OH 90/10/0.1)

δ $^1$H-NMR (CDCl$_3$): 1.42 (d, 3H); 3.26 (s, 3H); 5.03-5.61 (m, 1H); 7.47-7.60 (m, 5H); 7.93 (d, 1H); 7.99 (d, 1H); 8.12 (s, 1H)

LCMS: (Rt=3.35 min): 358–(M–CH$_3$CHOH)–

Analytical data for isomer D:

TLC: Fr=0.26 (dichloromethane/ethyl ether/NH4OH 90/10/0.1)

δ $^1$H-NMR (CDCl$_3$): 1.44 (d, 3H); 3.10 (s, 3H); 4.98-5.06 (m, 1H); 7.42-7.56 (m, 5H); 7.95 (d, 1H); 8.02 (d, 1H); 8.16 (s, 1H)

LCMS: (Rt=3.34 min): 358–(M–CH$_3$CHOH)–

Example 6

4-[4-(4-(2,5-Dioxo-4-fluorophenyl)-4-hydroxymethyl-3-methylimidazolidin-1-yl]-2-trifluoromethyl-benzonitrile (Method A)

Step 1: 1-(4-Fluorophenyl)-2-hydroxyethanone 2 g of 2-bromo-1-(4-fluorophenyl)ethanone, and 6 eq of sodium formate in 15 mL of Ethanol/Water are irradiated under microwave for 5 min at 150° C., 11 bars. After filtration and evaporation of ethanol, water is added. The expected product is isolated by filtration δ $^1$H NMR (DMSO D$_6$): 4.78 (s, 2H); 5.12 (m, 1H); 7.35 (m, 2H); 8.00 (m, 2H).

LCMS: (Rt=2.51 min): No ionization

Step 2: 1-(4-Fluorophenyl)-2-(2-propenyloxy)ethanone 2.4 g of 1-(4-fluorophenyl)-2-hydroxyethanone obtained in Step 1, 10 mL of allyl bromide and 9.4 g of CaSO$_4$ are mixed together under argon atmosphere. 6.2 g of Ag$_2$O are added by portions for 1.5 h. This mixture is stirred 3 h at rt, diluted with ethyl ether, filtered and the solvent is evaporated. The crude product is purified by chromatography over silica gel while eluting with 90/10 heptane/ethyl acetate δ $^1$H NMR (DMSO D$_6$): 4.05 (m, 2H); 4.82 (s, 2H); 5.17 (dd, 1H); 5.28 (dd, 1H); 5.92 (ddt, 1H); 7.37 (m, 2H); 8.00 (m, 2H)

LCMS: (Rt=2.69 min): No ionization

Step 3: 4-(4-Fluorophenyl)-4-[(2-propenyloxy)methyl]imidazolidine-2,5-dione 1.8 g of 1-(4-fluorophenyl)-2-(2-propenyloxy)ethanone obtained in Step 2, 1.21 g of potassium cyanide and 4.69 g of ammonium carbonate are heated to 55° C. for 2 hours in 50 mL of a 50/50 ethanol/water mixture. While heating the mixture at 55° C. 4.69 g of ammonium carbonate is added 3 times after 1 hour, 4 and 15 hours respectively. The reaction mixture is then diluted with water and extracted with ethyl acetate. The organic solution is dried over sodium sulfate and evaporated to provide the desired product.

δ $^1$H NMR (DMSO D$_6$): 3.50 (d, 1H); 3.95 (d, 1H); 4.03 (d, 2H); 5.15 (dd, 1H); 5.25 (dd, 1H, (dd, 1H); 5.85 (ddt, 1H); 7.25 (m, 2H); 7.58 (m, 2H); 8.65 (s, 1H); 10.80 (s, 1H).

LCMS: (Rt=2.43 min): No ionisation.

Step 4: 4-[2,5-Dioxo-4-(4-fluorophenyl)-4-[(2-propenyloxy)methyl]imidazolidin-1-yl]-2-trifluoromethylbenzonitrile 0.33 g of copper (I) oxide and 0.95 g of 4-bromo-2-trifluoromethylbenzonitrile are added to a solution of 1 g 4-(4-fluorophenyl)-4-[(2-propenyloxy)methyl]imidazolidine-2,5-dione obtained in step 3 in 3 mL of DMAC. The mixture is heated at 160° C. for 3 hours. After cooling, the mixture is diluted with a 50% aqueous ammonia solution and extracted with ethyl acetate. The organic layer is dried over sodium sulfate, filtered and evaporated. The crude product is purified by chromatography over silica gel while eluting with 2/1 heptane/ethyl acetate.

δ $^1$H NMR (DMSO D$_6$): 3.62 (d, 1H); 4.07 (m, 2H); 4.15 (d, 1H); 5.15 (d, 1H); 5.22 (d, 1H); 5.85 (ddt, 1H); 7.30 (m, 2H); 7.70 (m, 2H); 8.00 (d, 1H); 8.10 (s, 1H), 8.33 (d, 1H).

LCMS: (Rt=3.30 min): 432-(M-H-)

Step 5: 4-[2,5-Dioxo-4-(4-fluorophenyl)-3-methyl-4-[(2-propenyloxy)methyl]imidazolidin-1-yl]-2-trifluoromethylbenzonitrile 325 mg of potassium carbonate and 0.25 mL of iodomethane are added to a solution of 0.85 g of 4-[2,5-dioxo-4-(4-fluorophenyl)-4-[(2-prop enyloxy)methyl]imidazolidin-1-yl]-2-trifluoromethylbenzonitrile obtained in step 4, dissolved in 3 mL of DMF. The mixture is stirred at rt for 4 hours under argon atmosphere, evaporated to dryness, diluted with water and brine and extracted with ethyl acetate. The organic layer is dried over sodium sulfate, filtered and evaporated to provide the desired product.

δ $^1$H NMR (DMSO D$_6$): 2.85 (s, 3H); 4.17 (m, 2H); 4.20 (d, 1H); 4.40 (d, 1H); 5.15 (d, 1H); 5.21 (d, 1H); 5.87 (ddt, 1H); 7.30 (m, 2H); 7.55 (m, 2H); 8.00 (d, 1H); 8.12 (s, 1H), 8.33 (d, 1H).

LCMS: (Rt=3.43 min): No ionization

Step 6: 4-[2,5-Dioxo-4-(4-fluorophenyl)-4-hydroxymethyl-3-methylimidazolidin-1-yl]-2-trifluoromethylbenzonitrile The crude mixture of 4-[2,5-dioxo-4-(4-fluorophenyl)-3-methyl-4-[(2-propenyloxy)methyl]imidazolidin-1-yl]-2-trifluoromethylbenzonitrile obtained in step 5 is solubilised in 5 mL of DCM under argon atmosphere. 0.9 mL of trifluoroborane-dimethylsulfide complex is added. The mixture is stirred at rt for 7 hours. A saturated aqueous sodium bicarbonate solution is added slowly, the product is extracted with DCM and the organic layer is dried over sodium sulfate, filtered and evaporated. The crude product is purified by chromatography over silica gel while eluting with 4/1 DCM/ethyl acetate.

δ $^1$H NMR (DMSO D$_6$): 2.87 (s, 3H); 4.08 (m, 1H); 4.40 (m, 1H); 5.80 (m, 1H); 7.30 (m, 2H); 7.52 (m, 2H); 8.05 (d, 1H); 8.19 (s, 1H), 8.32 (d, 1H).

LCMS: (Rt=2.97 min): 376-(M-CH$_2$OH-)

Example 7

4-[4-(4-(4-Chlorophenyl)-2,5-dioxo-4-hydroxymethyl-3-methylimidazolidin-1-yl]-2-trifluoromethylbenzonitrile (Method A)

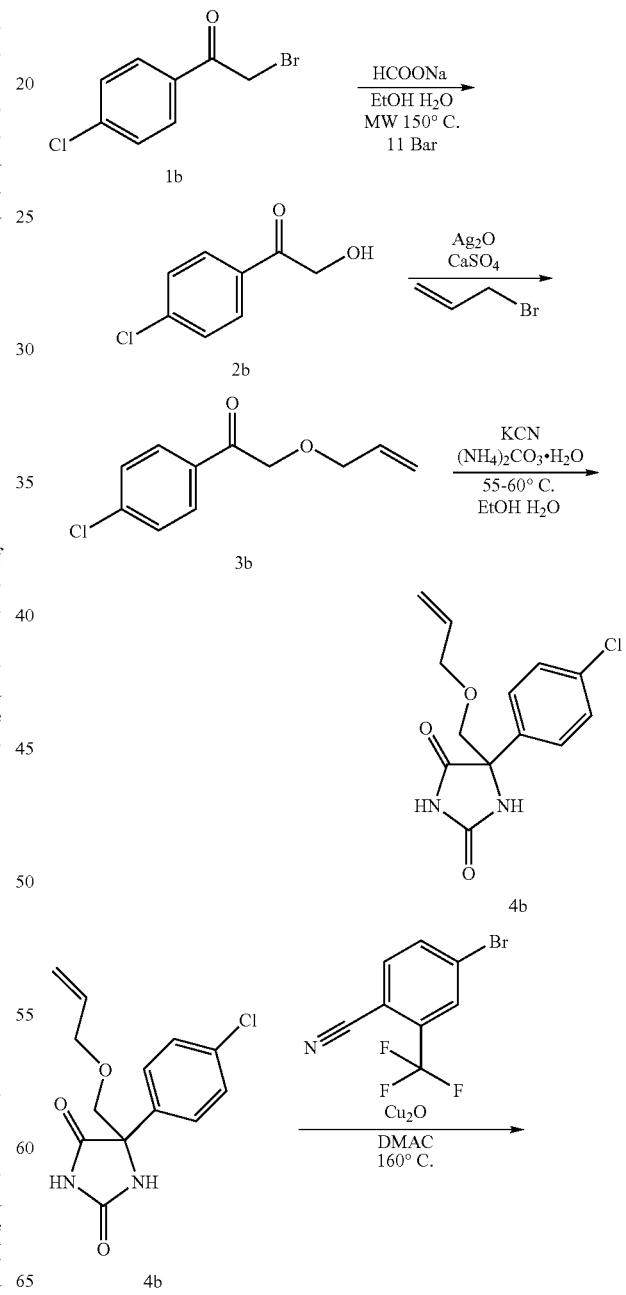

Scheme 3

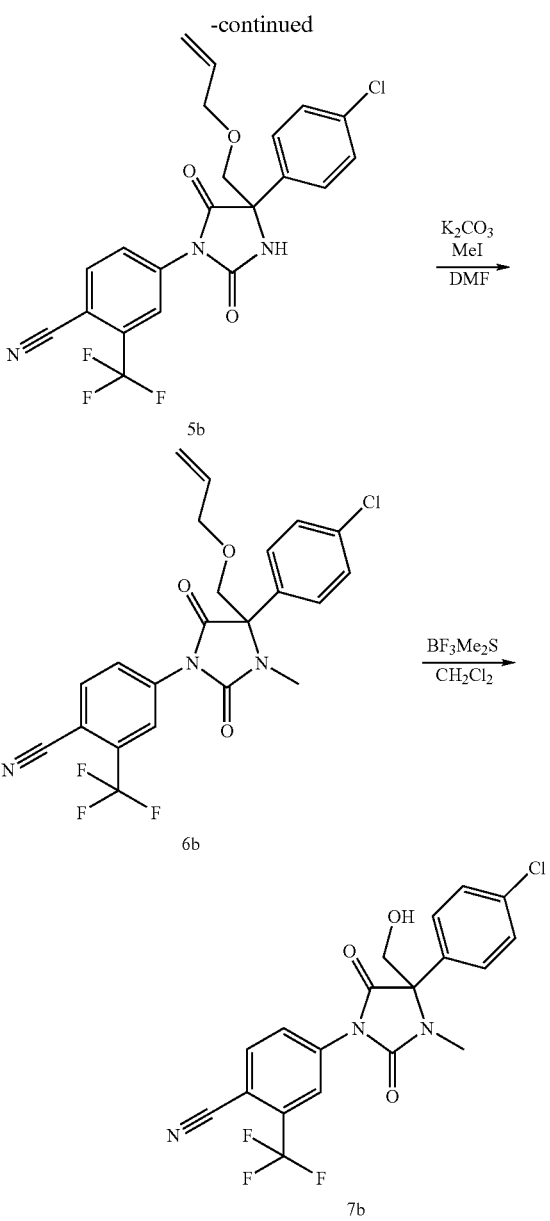

Step 3: 4-(4-Chlorophenyl)-4-(2-propenyloxy)imidazolidine-2,5-dione

Using the protocol of Example 6, step 3, reacting 2.5 g of 1-(4-chlorophenyl)-2-(2-propenyloxy)ethanone yields the desired product.

δ $^1$H NMR (DMSO D$_6$): 3.50 (d, 1H); 3.93 (d, 1H); 4.03 (d, 2H); 5.15 (dd, 1H); 5.25 (dd, 1H, (dd, 1H); 5.84 (ddt, 1H); 7.47 (m, 2H); 7.55 (m, 2H); 8.67 (s, 1H); 10.82 (s, 1H).
LCMS: (Rt=3.06 min): No ionisation.

Step 4: 4-[4-(4-Chlorophenyl)-2,5-dioxo-4-[(2-propenyloxy)methyl]imidazolidin-1-yl]-2-trifluoromethylbenzonitrile Using the protocol of Example 6, step 4, reacting 1.4 g of 4-(4-chlorophenyl)-4-(2-propenyloxy)imidazolidine-2,5-dione yields the desired product.

δ $^1$H NMR (DMSO D$_6$): 3.71 (d, 1H); 4.05 (m, 2H); 4.15 (d, 1H); 5.13 (d, 1H); 5.21 (d, 1H); 5.85 (ddt, 1H); 7.53 (d, 2H); 7.68 (d, 2H); 7.98 (d, 1H); 8.10 (s, 1H); 8.31 (d, 1H).
LCMS: (Rt=3.41 min): (448/450)−(M−H−)

Step 5: 4-[4-(4-Chlorophenyl)-2,5-dioxo-3-methyl-4-[(2-propenyloxy)methyl]imidazolidin-1-yl]-2-trifluoromethylbenzonitrile Using the protocol of Example 6, step 5, reacting 0.50 g of 4-[4-(4-chlorophenyl)-2,5-dioxo-4-[(2-propenyloxy)methyl]imidazolidin-1-yl]-2-trifluoromethylbenzonitrile yields the desired product.

δ $^1$H NMR (DMSO D$_6$): 2.87 (s, 3H); 4.10 (m, 2H); 4.18 (d, 1H); 4.40 (d, 1H); 5.15 (d, 1H); 5.21 (d, $^1$H); 5.88 (ddt, 1H); 7.54 (m, 4H); 8.00 (d, 1H); 8.12 (s, 1H); 8.33 (d, 1H).
LCMS: (Rt=3.57 min): No ionization

Step 6: 4-[4-(4-Chlorophenyl)-2,5-dioxo-4-hydroxymethyl-3-methylimidazolidin-1-yl]-2-trifluoromethylbenzonitrile Using the protocol of Example 6, step 6, reacting 0.6 g of 4-[4-(4-(4-chlorophenyl)-2,5-dioxo-3-methyl-4-[(2-propenyloxy)methyl]imidazolidin-1-yl]-2-trifluoromethylbenzonitrile yields the desired product.

δ $^1$H NMR (DMSO D$_6$): 2.87 (s, 3H); 4.07 (m, 1H); 4.40 (m, 1H); 5.82 (m, 1H); 7.51 (m, 4H); 8.03 (d, 1H); 8.19 (s, 1H); 8.32 (d, 1H).
LCMS: (Rt=3.13 min): (392/394)−(M−CH$_2$OH−)

Example 8

4-[4-(4-(4-Fluorophenyl)-2,5-dioxo-4-hydroxymethyl-3-(2-propynyl)imidazolidin-1-yl]-2-trifluoromethylbenzonitrile

Step 1: 4-[2,5-Dioxo-4-(4-fluorophenyl)-4-[(2-propenyloxy)methyl]-3-(2-propynyl)imidazolidin-1-yl]-2-trifluoromethylbenzonitrile To a solution of 0.42 g of 4-[2,5-dioxo-4-(4-fluorophenyl)-4-[(2-propenyloxy)methyl]imidazolidin-1-yl]-2-trifluoromethylbenzonitrile in 3 mL of DMF, 160 mg of potassium carbonate and 0.2 mL of propargylbromide (80% solution in toluene) are added. The mixture is stirred at room temperature for 4 hours under argon atmosphere. Then 0.04 mL of propargylbromide (80% solution in toluene) is added and the mixture is stirred 1 hour at room temperature, evaporated to

Step 1: 1-(4-Chlorophenyl)-2-hydroxyethanone

Using the protocol of Example 6, step 1, reacting 2 g of 2-bromo-1-(4-chlorophenyl)ethanone yields the desired product.

δ $^1$H NMR (DMSO D$_6$): 4.78 (s, 2H); 5.15 (m, 1H); 7.60 (d, 2H); 7.94 (d, 2H).
LCMS: (Rt=2.55 min): No ionisation

Step 2: 1-(4-Chlorophenyl)-2-(2-propenyloxy)ethanone

Using the protocol of Example 6, step 2, reacting 2.64 g of 2-bromo-1-(4-chlorophenyl)ethanone yields the desired product.

δ $^1$H NMR (DMSO D$_6$): 4.08 (m, 2H); 4.84 (s, 2H); 5.18 (dd, 1H); 5.29 (dd, 1H); 5.92 (ddt, 1H); 7.61 (d, 2H); 7.92 (d, 2H)

dryness, diluted with water and brine and extracted with ethyl acetate. The organic layer is dried over sodium sulfate filtered and evaporated.

The crude product is purified by chromatography over silica gel while eluting with 4/1 heptane/ethyl acetate.

δ $^1$H NMR (DMSO D$_6$): 3.17 (s, 1H); 4.05-4.12 (m, 2H); 4.25-4.40 (m, 4H); 5.12 (d, 1H); 5.22 (d, 1H); 5.88 (ddt, 1H); 7.30 (m, 2H); 7.60 (m, 2H); 8.00 (d, 1H); 8.12 (s, 1H); 8.33 (d, 1H).

LCMS: (Rt=3.46 min): No ionization

Step 2: 4-[4-(4-Fluorophenyl)-2,5-dioxo-4-hydroxymethyl-3-(2-propynyl)imidazolidin-1-yl]-2-trifluoromethylbenzonitrile 0.45 g of 4-[2,5-dioxo-4-(4-fluorophenyl)-4-[(2-propenyloxy)methyl]-3-(2-propynyl)imidazolidin-1-yl]-2-trifluoromethylbenzonitrile obtained in step 1 is dissolved in 5 mL of DCM under argon atmosphere. 0.2 mL of trifluoroborane-dimethylsulfide complex is added. The mixture is stirred at room temperature for 18 hours. A saturated aqueous sodium bicarbonate solution is slowly added. The product is extracted with DCM and the organic layer is dried over sodium sulfate, filtered and evaporated. The crude product is purified by chromatography over silica gel while eluting with 6/1 DCM/ethyl acetate.

δ $^1$H NMR (DMSO D$_6$): 3.10 (m, 3H); 4.10-4.40 (m, 4H); 5.80 (m, 1H); 7.28 (m, 2H); 7.60 (m, 2H); 8.05 (d, 1H); 8.20 (s, 1H); 8.35 (d, 1H).

LCMS: (Rt=3.07 min): 400–(M–CH$_2$OH–)

Example 9

4-[4-(4-(3-Chlorophenyl)-2,5-dioxo-4-hydroxymethyl-3-methylimidazolidin-1-yl]-2-trifluoromethylbenzonitrile (Method A)

Step 1: 1-(3-Chlorophenyl)-2-hydroxyethanone

Using the protocol of Example 6, step 1, reacting 2 g of 2-bromo-1-(3-chlorophenyl)ethanone yields the desired product.

δ $^1$H NMR (DMSO D$_6$): 4.80 (s, 2H); 5.20 (m, 1H); 7.58 (t, 1H); 7.72 (d, 1H); 7.88 (d, 1H); 7.95 (s, 1H).

LCMS: (Rt=2.30 min): No ionization

Step 2: 1-(3-Chlorophenyl)-2-(2-propenyloxy)ethanone

Using the protocol of Example 6, step 2, reacting 2.5 g of 1-(3-chlorophenyl)-2-hydroxyethanone yields the desired product.

δ $^1$H NMR (DMSO D$_6$): 4.07 (m, 2H); 4.88 (s, 2H); 5.18 (dd, 1H); 5.30 (dd, 1H); 5.92 (ddt, 1H); 7.58 (t, 1H); 7.72 (d, 1H); 7.88 (d, 1H); 7.92 (s, 1H).

Step 3: 4-(3-Chlorophenyl)-4-(2-propenyloxy)imidazolidine-2,5-dione

Using the protocol of Example 6, step 3, reacting 1.5 g of 1-(3-chlorophenyl)-2-(2-propenyloxy)ethanone yields the desired product.

δ $^1$H NMR (DMSO D$_6$): 3.52 (d, 1H); 3.95 (d, 1H); 4.02 (d, 2H); 5.16 (dd, 1H); 5.25 (dd, 1H); 5.85 (ddt, 1H); 7.44 (m, 2H); 7.52 (m, 1H); 7.59 (s, 1H); 8.70 (s, 1H); 10.83 (s, 1H).

LCMS: (Rt=2.57 min): No ionization

Step 4: 4-[4-(3-Chlorophenyl)-2,5-dioxo-4-[(2-propenyloxy)methyl]imidazolidin-1-yl]-2-trifluoromethylbenzonitrile Using the protocol of Example 6, step 4, reacting 1.0 g of 4-(3-chlorophenyl)-4-(2-propenyloxy)imidazolidine-2,5-dione yields the desired product.

δ $^1$H NMR (DMSO D$_6$): 3.72 (d, 1H); 4.05 (m, 2H); 4.18 (d, 1H); 5.13 (d, 1H); 5.21 (d, 1H); 5.85 (ddt, 1H); 7.50 (m, 2H); 7.62 (m, 1H); 7.70 (s, 1H); 7.98 (d, 1H); 8.10 (s, 1H); 8.32 (d, 1H); 9.12 (s, 1H).

LCMS: (Rt=3.41 min): (448/450)–(M–H–)

Step 5: 4-[4-(3-Chlorophenyl)-2,5-dioxo-3-methyl-4-[(2-propenyloxy)methyl]imidazolidin-1-yl]-2-trifluoromethylbenzonitrile Using the protocol of Example 6, step 5, reacting 0.66 g of 4-[4-(4-(3-chlorophenyl)-2,5-dioxo-4-[(2-propenyloxy)methyl]imidazolidin-1-yl]-2-trifluoromethylbenzonitrile yields the desired product.

δ $^1$H NMR (DMSO D$_6$): 2.88 (s, 3H); 4.10 (m, 2H); 4.20 (d, 1H); 4.42 (d, 1H); 5.16 (d, 1H); 5.22 (d, 1H); 5.89 (ddt, 1H); 7.50 (m, 1H); 7.52 (m, 2H); 7.60 (s, 1H); 8.00 (d, 1H); 8.15 (s, 1H); 8.33 (d, 1H).

LCMS: (rt=3.57 min, apolar method): No ionisation

Step 6: 4-[4-(3-Chlorophenyl)-2,5-dioxo-4-hydroxymethyl-3-methylimidazolidin-1-yl]-2-trifluoromethylbenzonitrile Using the protocol of Example 6, step 6, reacting 0.60 g of 4-[4-(4-(3-chlorophenyl)-2,5-dioxo-3-methyl-4-[(2-propenyloxy)methyl]imidazolidin-1-yl]-2-trifluoromethylbenzonitrile yields the desired product.

δ $^1$H NMR (MeOD): 3.08 (s, 3H); δ 4.20 (m, 1H); 4.61 (m, 1H); 7.45 (m, 1H); 7.52 (m, 2H); 8.14 (m, 2H); 8.25 (s, 1H).

LCMS: (Rt=3.10 min): (392/394)–(M–CH$_2$OH–)

Examples 10 & 11

(S)-4-[2,5-Dioxo-4-hydroxymethyl-3-methyl-4-phenylimidazolidin-1-yl]-2-trifluoromethylbenzonitrile & (R)-4-[2,5-Dioxo-4-hydroxymethyl-3-methyl-4-phenylimidazolidin-1-yl]-2-trifluoromethylbenzonitrile The two enantiomers of 4-[2,5-dioxo-4-hydroxymethyl-3-methyl-4-phenylimidazolidin-1-yl]-2-trifluoromethylbenzonitrile are separated by chromatography of a 1.5 g sample of the racemic mixture obtained in Example 1 on Chiralcel OD (LC50 Prochrom column) while eluting with a 75/25 heptane/isopropanol mixture.

The (S) enantiomer is eluted first. By evaporating the solvent, the desired compound is obtained.

[α]$_D$=–40.8° (c=1%, EtOH).

HPLC: Chiralcel OD, column 250×4.6 mm, heptane/isopropanol 75/25, flow rate 1 mL/min, Rt: 9.01 min.

The (R) enantiomer is eluted second. A further purification in the same conditions followed by evaporating the solvent provides the desired compound.

[α]$_D$=+ 41.1° (c=1%, EtOH).
HPLC: Chiralcel OD, column 250×4.6 mm, heptane/isopropanol 75/25, flow rate 1 mL/min, Rt: 13.24 min.
Alternative route:

trile is treated with 0.2 mL of trifluoroborane-dimethylsulfide complex as described in Example 3, Step 2, to provide the desired compound.
TLC: Fr=0.35 (heptane/ethyl acetate 20/10)

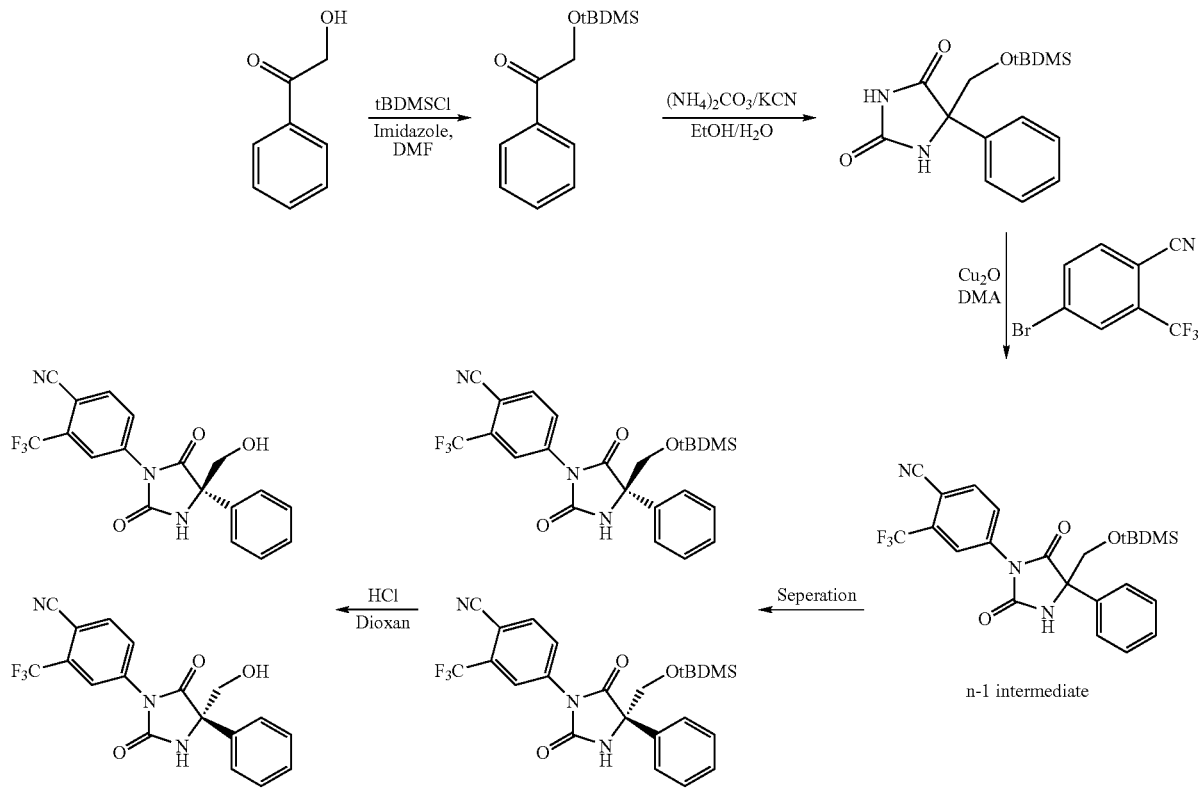

Following the same route as described for Example 1 depicted in Scheme 3, purification can be carried out on the "n−1 intermediate", to obtain the compounds from Example 10 and 11 after deprotection using a ChiralpakAD® column (250×4.6 mm), using a mixture of supercritical CO$_2$/MeCN/iPrOH (90/5/5) at 40° C., under 100 bars, followed by removal of the protecting group according to known procedures (see ref 10).

Example 12

4-[2,5-Dioxo-3-ethyl-4-hydroxymethyl-4-phenylimidazolidin-1-yl]-2-trifluoromethylbenzonitrile (Method A)

Step 1: 4-[2,5-Dioxo-3-ethyl-4-phenyl-4-[(2-propenyloxy)methyl]imidazolidin-1-yl]-2-trifluoromethylbenzonitrile The procedure of Example 1, Step 1 applied to 0.23 g of 4-[2,5-dioxo-4-phenyl-4-[(2-propenyloxy)methyl]imidazolidin-1-yl]-2-trifluoromethylbenzonitrile with 0.18 mL of iodoethane provides the desired compound.
LCMS: (Rt=3.20 min): 444+ (MH+)

Step 2: 4-[2,5-Dioxo-3-ethyl-4-hydroxymethyl-4-phenylimidazolidin-1-yl]-2-trifluoromethylbenzonitrile 0.2 g of 4-[2,5-dioxo-3-ethyl-4-phenyl-4-[(2-propenyloxy)methyl]imidazolidin-1-yl]-2-trifluoromethylbenzonitrile δ $^1$H NMR (DMSO D$_6$): 1.05 (t, 3H); 3.32 (q, 2H); 4.22 and 4.40 (2m, 2H); 5.62 (t, 1H); 7.4-7.5 (m, 5H); 8.08 (d, 1H); 8.20 (s, 1H); 8.33 (d, 1H).
LCMS: (Rt=3.81 min): 372−(M−CH$_2$OH−)

Example 13

4-[4-(4-(4-Cyanophenyl)-2,5-dioxo-4-hydroxymethyl-3-methylimidazolidin-1-yl]-2-trifluoromethylbenzonitrile (Method A)

Step 1: 4-(2-Hydroxyacetyl)benzonitrile

A solution of 1 g of 4-(2-bromoacetyl)benzonitrile in acetonitrile (5 mL) and water (10 mL) is treated under microwave irradiation (125° C., 50 min) The same experiment is conducted five times. All the vials are collected, extracted with ethyl ether, dried over magnesium sulfate and concentrated under vacuum to give the desired compound.
TLC: Fr=0.15 (ethyl acetate/cyclohexane 30/70)
δ $^1$H NMR (CDCl$_3$): 4.94 (s, 2H); 7.85-7.87 (dd, 2H); 8.05-8.07 (dd, 2H)
LCMS: (Rt=2.40 min): Not ionisable Step 2: 4-[2-(2-Propenyloxy)acetyl]benzonitrile To a solution of 2.7 g of 4-(2-hydroxyacetyl)benzonitrile in allyl bromide (15 mL) is added 10.2 g calcium sulfate and 6.7 g of silver oxide. The mixture is stirred under argon and in the dark for 2 hours. The mixture is diluted with AcOEt, filtered on celite, concentrated and purified on silica gel (ethyl acetate/cyclohexane: 0/100 to 50/50) to give the desired compound.

TLC: Fr=0.38 (ethyl acetate/cyclohexane 40/60)

δ $^1$H NMR (CDCl$_3$): 4.01 (d, 2H); 4.57 (s, 2H); 5.13 (d, 1H); 5.22 (s, 1H); 5.73-5.86 (m, 1H); 7.64 (d, 2H); 7.91 (d, 2H)

LCMS: (Rt=3.05 min): Not ionisable

Step 3: 4-[2,5-Dioxo-4-[(2-propenyloxy)methyl]imidazolidin-4-yl]benzonitrile To a solution of 500 mg of 4-[2-(2-propenyloxy)acetyl]benzonitrile (in EtOH (5 mL) and water (5 mL) is added 324 mg potassium cyanide and 1.67 g of ammonium carbonate. The mixture is refluxed overnight at 55° C. The mixture is extracted with ethyl acetate, dried over magnesium sulfate and concentrated under vacuum to give the desired compound.

TLC: Fr=0.16 (ethyl acetate/cyclohexane 30/70)

δ $^1$H NMR (CD$_3$OD): 3.45 (d, 1H); 3.86 (m, 3H); 4.95 (d, 1H); 5.06 (dd, 1H); 5.60-5.73 (m, 1H); 7.58 (s, 4H)

LCMS: (Rt=2.77 min): 270–(M–H)–

Step 4: 4-[4-(4-Cyanophenyl)-2,5-dioxo-4-[(2-propenyloxy)methyl]imidazolidin-1-yl]-2-trifluoromethylbenzonitrile To a solution of 675 mg of 4-[2,5-dioxo-4-[(2-propenyloxy)methyl]imidazolidin-4-yl]benzonitrile and 622 mg of 4-bromo-2-trifluoromethylbenzonitrile in DMAC (2.5 mL) 214 mg of copper (I) oxide is added. The mixture is refluxed overnight at 130° C. The mixture is concentrated, taken in DCM, washed with a 10% aqueous ammonia solution and brine. The organic phase is dried over magnesium sulfate, concentrated under vacuum and purified on silica gel (ethyl acetate/cyclohexane: 0/100 to 50/50) to give the desired compound.

TLC: Fr=0.48 (ethyl acetate/cyclohexane 50/50)

δ $^1$H NMR (CDCl$_3$): 3.85 (d, 1H); 4.09-4.19 (m, 3H); 5.25-5.31 (m, 2H); 5.80-5.87 (m, 1H); 6.07 (s, 1H); 7.79-7.84 (s, 4H); 7.95 (s, 2H); 8.07 (s, 1H)

LCMS: (Rt=3.29 min): 439–(M–H)–

Step 5: 4-[4-(4-Cyanophenyl)-2,5-dioxo-3-methyl-4-[(2-propenyloxy)methyl]imidazolidin-1-yl]-2-trifluoromethylbenzonitrile To a solution of 459 mg of 4-[4-(4-cyanophenyl)-2,5-dioxo-4-[(2-propenyloxy)methyl]imidazolidin-1-yl]-2-trifluoromethylbenzonitrile obtained in Step 4 in DMF (1.5 mL), 173 mg of potassium carbonate and 130 μL of methyliodide are added. The mixture is stirred 3 hours at rt, evaporated, washed with brine, extracted with ethyl acetate, dried over magnesium sulfate and concentrated to give the desired compound.

TLC: Fr=0.54 (ethyl acetate/cyclohexane 50/50)

δ $^1$H NMR (CDCl$_3$): 3.09 (s, 3H); 3.95 (d, 1H); 4.14 (m, 2H); 4.39 (d, 1H); 5.28-5.34 (m, 2H); 5.84-5.91 (m, 1H); 7.57 (d, 2H); 7.80 (d, 2H), 7.95 (s, 2H); 8.10 (s, 1H)

LCMS: (Rt=3.81 min): Not ionisable

Step 6: 4-[4-(4-Cyanophenyl)-2,5-dioxo-4-hydroxymethyl-3-methylimidazolidin-1-yl]-2-trifluoromethylbenzonitrile To a solution of 433 mg of 4-[4-(4-cyanophenyl)-2,5-dioxo-3-methyl-4-[(2-propenyloxy)methyl]imidazolidin-1-yl]-2-trifluoromethylbenzonitrile obtained in Step 5 in DCM (5 mL), 600 μL of boron trifluoride-dimethyl sulfide complex is added. The mixture is stirred 8 hours at rt, diluted with DCM, washed with an aqueous solution of sodium bicarbonate, dried over magnesium sulfate, concentrated and purified on silica gel (ethyl acetate/cyclohexane: 0/100 to 50/50) to give the desired compound.

TLC: Fr=0.10 (ethyl acetate/cyclohexane 30/70)

δ $^1$H NMR (CDCl$_3$): 3.14 (s, 3H); 4.16 (d, 1H); 4.73 (d, 1H); 7.57 (d, 2H); 7.82 (d, 2H), 7.93-8.00 (m, 2H), 8.13 (s, 1H)

LCMS: (Rt=3.05 min): 383–(M–CH$_2$OH)–

Example 14

4-[4-(4-(3-Cyanophenyl)-2,5-dioxo-4-hydroxymethyl-3-methylimidazolidin-1-yl]-2-trifluoromethylbenzonitrile (Method A)

Step 1: 3-(2-Hydroxyacetyl)benzonitrile

A solution of 776 mg of 3-(2-bromoacetyl)benzonitrile in acetonitrile (5 mL) and water (10 mL) is treated under microwave irradiation (125° C., 50 min) The same experiment is realized a second time with 976 mg. All the vials are collected, extracted with ethyl ether, dried over magnesium sulfate and concentrated under vacuum to give the desired compound.

TLC: Fr=0.38 (ethyl acetate/cyclohexane 30/70)

δ $^1$H NMR (CDCl$_3$): 4.94 (s, 2H); 7.71 (t, 1H); 7.95 (d, 1H); 8.18 (d, 1H); 8.25 (s, 1H)

Step 2: 3-[(2-(2-Propenyloxy)acetyl]benzonitrile

To a solution of 1.08 g of 3-(2-hydroxyacetyl)benzonitrile in allyl bromide (8 mL) 4 g of calcium sulfate and 2.6 g of silver oxide are added. The mixture is stirred under argon and dark overnight. The mixture is diluted with ethyl acetate, filtrated on celite, concentrated and purified on silica gel (ethyl acetate/cyclohexane 0/100 to 30/70) to give the desired compound.

TLC: Fr=0.64 (ethyl acetate/cyclohexane 30/70)

δ $^1$H NMR (CDCl$_3$): 4.18 (d, 2H); 4.73 (s, 2H); 5.31 (d, 1H); 5.37 (d, 1H); 5.92-6.02 (m, 1H); 7.66 (t, 1H); 7.90 (d, 1H); 8.22 (d, 1H); 8.29 (s, 1H)

LCMS: (Rt=3.04 min: Not ionisable

Step 3: 3-[2,5-Dioxo-4-[(2-propenyloxy)methyl]imidazolidin-4-yl]benzonitrile To a solution of 450 mg of 3-[(2-(2-propenyloxy)acetyl]benzonitrile (in EtOH (5 mL) and water (5 mL) 291 mg of potassium cyanide and ammonium carbonate are added. The mixture is refluxed one night at 55° C. The mixture is extracted with ethyl acetate, dried over magnesium sulfate and concentrated under vacuum to give the desired compound.

TLC: Fr=0.1 (ethyl acetate/cyclohexane 30/70)

δ $^1$H NMR (CD$_3$OD): 3.70 (d, 1H); 4.10-4.14 (m, 3H); 5.23 (d, 1H); 5.33 (d, 1H); 5.89-5.98 (m, 1H); 7.67 (t, 1H); 7.80 (d, 2H); 7.98-8.02 (m, 1H)

Step 4: 4-[4-(3-Cyanophenyl)-2,5-dioxo-4-[(2-propenyloxy)methyl]imidazolidin-1-yl]-2-trifluoromethylbenzonitrile To a solution of 579 mg of 3-[2,5-dioxo-4-[(2-propenyloxy)methyl]imidazolidin-4-yl]benzonitrile and 534 mg of 4-bromo-2-(trifluoromethyl)benzonitrile in DMAC (2.5 mL), 183 mg of copper oxide are added. The mixture is refluxed overnight at 130° C. The mixture is concentrated, taken in DCM, washed with a solution of 10% aqueous ammonia solution and brine. The organic phase is dried over magnesium sulfate, concentrated under vacuum and purified on silica gel (ethyl acetate/cyclohexane 0/100 to 50/50) to give the desired compound.

TLC: Fr=0.3 (ethyl acetate/cyclohexane 50/50)

δ $^1$H NMR (CDCl$_3$): 3.85 (d, 1H); 4.07-4.21 (m, 3H); 5.26-5.38 (m, 2H); 5.80-5.89 (m, 1H); 6.24 (s, 1H); 7.59-7.70 (m, 1H); 7.80 (d, 1H); 7.94-8.19 (m, 5H)

LCMS: (Rt=3.26 min): 439−(M−H)−

Step 5: 4-[4-(3-Cyanophenyl)-2,5-dioxo-3-methyl-4-[(2-propenyloxy)methyl]imidazolidin-1-yl]-2-trifluoromethylbenzonitrile To a solution of 358 mg of 4-[4-(3-cyanophenyl)-2,5-dioxo-4-[(2-propenyloxy)methyl]imidazolidin-1-yl]-2-trifluoromethylbenzonitrile in DMF (1.5 mL) 135 mg of potassium carbonate and 101 µL of methyl iodide are added. The mixture is stirred during the night at room temperature, evaporated, washed with brine, extracted with ethyl acetate, dried over magnesium sulfate and concentrated to give the desired compound.

TLC: Fr=0.58 (ethyl acetate/cyclohexane 50/50)

δ $^1$H NMR (CDCl$_3$): 3.09 (s, 3H); 3.95 (d, 1H); 4.14 (m, 2H); 4.38 (d, 1H); 5.29-5.34 (m, 2H); 5.84-5.91 (m, 1H); 7.63-7.79 (m, 4H); 7.96 (s, 2H); 8.11 (s, 1H)

LCMS: (Rt=3.81 min): Not ionisable

Step 6: 4-[4-(3-Cyanophenyl)-2,5-dioxo-4-hydroxymethyl-3-methylimidazolidin-1-yl]-2-trifluoromethyl-benzonitrile 328 µL of trifluoroborane-dimethylsulfide complex are added to a solution of 354 mg of 4-[4-(3-cyanophenyl)-2,5-dioxo-3-methyl-4-[(2-propenyloxy)methyl]imidazolidin-1-yl]-2-trifluoromethylbenzonitrile (in DCM (5 mL. The mixture is stirred 6 hours at room temperature, diluted with DCM, washed with an aqueous solution of sodium bicarbonate, dried over magnesium sulfate, concentrated and purified on silica gel (ethyl acetate/cyclohexane 0/100 to 50/50) to give the desired compound.

TLC: Fr=0.30 (ethyl acetate/cyclohexane 50/50)

δ $^1$H NMR (CDCl$_3$): 3.14 (s, 3H); 4.17 (m, 1H); 4.71 (d, 1H); 7.65-7.79 (m, 4H); 7.94-8.02 (m, 2H); 8.14 (s, 1H)

LCMS: (Rt=3.04 min): 383−(M−CH$_2$OH)−

Example 15

4-[2,5-Dioxo-4-hydroxymethyl-3-methyl-4-(3-trifluoromethylphenyl)imidazolidin-1-yl]-2-trifluoromethyl-benzonitrile (Method A)

Step 1: 1(3-Trifluoromethylphenyl)-2-hydroxyethanone

A solution of 2-bromo-1-[3-(trifluoromethyl)phenyl]ethanone (1 g) in acetonitrile (2.5 mL) and water (10 mL) is treated under microwave irradiation (125° C., 50 min) The same experiment is repeated five times. All the vials are collected, extracted with DCM, dried over magnesium sulfate and concentrated under vacuum to give the desired compound.

δ $^1$H NMR (CDCl$_3$): 4.96 (s, 2H); 7.70 (m, 1H); 7.93 (d, 1H); 8.14 (d, 1H), 8.22 (s, 1H)

Step 2: 2-[(2-Propenyloxy)methyl]-1(3-trifluoromethylphenyl)ethanone

To a solution of 1-(3-trifluoromethylphenyl)-2-hydroxyethanone (3.66 g) in allyl bromide (20 mL) is added calcium sulfate (10.9 g) and silver oxide (7.1 g). The mixture is stirred under argon and dark during 2 hours. The mixture is diluted with ethyl acetate, filtered on celite, concentrated and purified on silica gel (ethyl acetate/cyclohexane 0/100 to 15/85) to give the desired compound.

TLC: Fr=0.79 (ethyl acetate/cyclohexane 50/50)

δ $^1$H NMR (CDCl$_3$): 4.20 (m, 2H); 4.78 (s, 2H); 5.30 (d, 1H); 5.38 (d, 1H); 5.94-6.02 (m, 1H); 7.66 (t, 1H); 7.88 (d, 1H); 8.18 (d, 1H), 8.25 (s, 1H)

LCMS: (Rt=3.53 min): Not ionisable

Step 3: 4-[(2-Propenyloxy)methyl]-4-(3-(trifluoromethylphenyl)imidazolidin-2,5-dione To a solution of 2-[(2-propenyloxy)methyl]-1-(3-trifluoromethylphenyl)ethanone (1.17 g) in EtOH (5 mL) and water (5 mL) is added potassium cyanide (624 mg) and ammonium carbonate (3.2 g). The mixture is refluxed overnight at 55° C. The mixture is extracted with ethyl acetate, dried over magnesium sulfate and concentrated under vacuum to give the desired compound.

TLC: Fr=0.45 (ethyl acetate/cyclohexane 50/50)

δ $^1$H NMR (CDCl$_3$): 3.80 (d, 1H); 4.00-4.10 (m, 3H); 5.20-5.27 (m, 2H); 5.77-5.87 (m, 1H); 6.77 (s, 1H); 7.57 (t, 1H); 7.67 (d, 1H); 7.77-7.88 (m, 2H), 8.59 (s, 1H)

LCMS: (Rt=3.19 min): 313−(M−H)−

Step 4: 4-[2,5-Dioxo-4-[(2-propenyloxy)methyl]-4-(3-trifluoromethylphenyl)-imidazolidin-1-yl]-2-trifluoromethylbenzonitrile To a solution of 4-[(2-propenyloxy)methyl]-4-(3-trifluoromethylphenyl)imidazolidin-2,5-dione (1.45 g) and 4-bromo-2-(trifluoromethyl)benzonitrile (1.15 g) in DMAC (7 mL) is added copper oxide (528 mg). The mixture is refluxed overnight at 130° C. The mixture is concentrated, taken in ethyl acetate, washed with a 10% aqueous ammonia solution and brine. The organic phase is dried over magnesium sulfate, concentrated under vacuum and purified on silica gel (ethyl acetate/cyclohexane 0/100 to 50/50) to give the desired compound.

TLC: Fr=0.69 (ethyl acetate/cyclohexane 50/50)

δ $^1$H NMR (CDCl$_3$): 3.84 (d, 1H); 4.10 (m, 2H); 4.20 (d, 1H); 5.25-5.30 (m, 2H); 5.80-5.89 (m, 1H); 6.57 (s, 1H); 7.62-7.66 (t, 1H); 7.74 (d, 1H); 7.91-7.96 (m, 4H); 8.09 (s, 1H)

LCMS: (Rt=3.55 min): 482−(M−H)−

Step 5: 4-[2,5-Dioxo-3-methyl-4-[(2-propenyloxy)methyl]-4-(3-trifluoromethylphenyl)imidazolidin-1-yl]-2-trifluoromethylbenzonitrile To a solution of 814 mg of 4-[2,5-dioxo-4-[(2-propenyloxy)methyl]-4-(3-trifluoromethylphenyl)imidazolidin-1-yl]-2-trifluoromethylbenzonitrile in DMF (1.5 mL) is added potassium carbonate (279 mg) and methyliodide (420 µL). The mixture is stirred 5 hours at room temperature, evaporated, washed with brine, extracted with ethyl acetate, dried over magnesium sulfate and concentrated to give the desired compound.

TLC: Fr=0.39 (ethyl acetate/cyclohexane 30/70)

δ $^1$H NMR (CDCl$_3$): 3.09 (s, 3H); 3.98 (d, 1H); 4.14-4.19 (m, 2H); 4.42 (d, 1H); 5.28-5.34 (m, 2H); 5.85-5.92 (m, 1H); 7.64-7.68 (m, 3H); 7.75 (d, 1H); 7.93-8.00 (m, 2H), 8.12 (s, 1H)

LCMS: (Rt=4.05 min): Not ionisable

Step 6: 4-[2,5-Dioxo-4-hydroxymethyl-3-methyl-4-(3-trifluoromethylphenyl)imidazolidin-1-yl]-2-trifluoromethyl-benzonitrile To a solution of 782 mg of 4-[4-(3-Trifluoromethylphenyl)-2,5-dioxo-3-methyl-4-[(2-propenyloxy)methyl]imidazolidin-1-yl]-2-trifluoromethylbenzonitrile in DCM (5 mL), 662 μL of trifluoroborane-dimethylsulfide complex are added. The mixture is stirred 6 hours at room temperature, diluted with DCM, washed with an aqueous solution of sodium bicarbonate, dried over magnesium sulfate, concentrated and purified on silica gel (ethyl acetate/cyclohexane 0/100 to 50/50) to give the desired compound.

TLC: Fr=0.45 (ethyl acetate/cyclohexane 50/50)

δ $^1$H NMR (CDCl$_3$): 3.14 (s, 3H); 4.18 (d, 1H); 4.75 (dd, 1H); 7.62-7.69 (m, 3H); 7.76 (d, 1H); 7.95 (d, 1H); 8.02 (d, 1H); 8.16 (s, 1H)

LCMS: (Rt=3.10 min): 426–(M–CH2OH)–

Example 16

1-(3,4-Dichlorophenyl)-4-hydroxymethyl-3-methyl-4-phenylimidazolidine-2,5-dione (Method A)

Step 1: 1-Phenyl-2-(2-propenyloxy)ethanone

This compound is prepared from 2-hydroxy-1-phenylethanone, according to the procedure used by G. A. Molander and J. A. McKie on 1-hydroxy-butan-2-one, J. Org. Chem. (1995), 60, 872-882.

Step 2: 4-Phenyl-4-[(2-propenyloxy)methyl]imidazolidine-2,5-dione 0.775 g of 1-phenyl-2-(2-propenyloxy)ethanone, 0.575 g of potassium cyanide and 1.6 g of ammonium carbonate are heated to 55° C. for 3 hours in 23 mL of a 50/50 ethanol/water mixture. The reaction mixture is diluted with water and extracted with ethyl acetate. The organic solution is washed with a saturated aqueous sodium chloride solution, then dried over sodium sulphate and evaporated to yield the desired compound.

TLC: Rf=0.42 (silicagel, eluant: heptane-ethyl acetate 50-50)

δ $^1$H-NMR (CD$_3$OD): 3.68 (d, 1H); 4.13 (m, 3H); 4.22 (d, 1H); 4.92 (s, 2H); 5.22 (dd, 1H); 5.34 (dd, 1H); 5.95 (ddt, 1H); 7.45 (m, 3H); 7.64 (d, 2H)

LCMS: (rt=5.79 min): 288+ (MH, MeCN+)

Step 3: 1-(3,4-Dichlorophenyl)-4-phenyl-4-[(2-propenyloxy)methyl]imidazolidine-2,5-dione 0.7 g of 4-phenyl-2-(propenyloxy)imidazolidine-2,5-dioneare dissolved in 2 mL DMAC and 780 mg of 1,2-dichloro-4-iodo-benzene are added, followed by 234 mg of copper (I) oxide. The mixture is warmed at 160° C. for 3 hours. At rt the mixture is diluted with a 20% aqueous solution of ammonia and extracted with ethyl acetate. The organic layer is dried over sodium sulfate, filtered and evaporated. The crude product is purified by chromatography over silica gel while eluting with the 2/1 heptane/ethyl acetate mixture.

δ $^1$H NMR (DMSO): 3.70 (d, 1H); 4.08 (m, 2H); 4.15 (d, 1H); 5.17 (d, 1H); 5.25 (d, 1H); 5.88 (ddt, 1H); 7.38-7.50 (m, 4H); 7.62 (d, 2H); 7.67 (m, 1H); 7.78 (d, 1H), 9.40 (s, 1H).

LCMS: (Rt=3.44 min): no ionization

Step 4: 1-(3,4-Dichlorophenyl)-4-hydroxymethyl-3-methyl-4-phenylimidazolidine-2,5-dione To a solution of 0.45 g of 5-1-(3,4-dichlorophenyl)-4-phenyl-4-[(2-propenyloxy)methyl]imidazolidine-2,5-dione in 3 mL of DMF, 238 mg of potassium carbonate and 0.143 mL of iodomethane. The mixture is stirred at rt for 5 hours, evaporated to dryness, diluted with brine and extracted with ethyl acetate. The organic layer is dried over sodium sulfate, filtered and evaporated to afford 0.47 g of yellow oil, which is then dissolved in 5 mL of DCM under argon atmosphere. 0.4 mL of trifluoroborane-dimethylsulfide complex is then added. The mixture is stirred at rt for 5 hours. A saturated aqueous sodium bicarbonate solution is added slowly. The mixture is extracted with DCM and the organic layer is dried over sodium sulfate, filtered and evaporated. The crude product is purified by crystallization from DCM/ethyl ether.

δ $^1$H NMR (MeOD): 3.02 (s, 3H); 4.20 (d, 1H); 4.62 (d, 1H); 7.43-7.57 (m, 5H); 7.68 (d, 1H); 7.92 (d, 1H); 7.75 (m, 1H).

LCMS: (Rt=3.13 min): No ionization

General procedure for Examples 17 to 19, (Method A)

Step 1

0.415 g of 4-[2,5-dioxo-4-phenyl-4-[(2-propenyloxy)methyl]imidazolidin-1-yl]-2-trifluoromethylbenzonitrile are dissolved in 40 mL of DMF with the appropriate alkyl halide and 163 mg of potassium carbonate. The mixture is stirred at rt for 5 h, evaporated to dryness, diluted with water and extracted with ethyl acetate. The organic layer is dried over magnesium sulfate, filtered and the solvent is evaporated. The crude product is purified by chromatography over silica gel while eluting with 70/30 heptane/ethyl acetate mixture.

Step 2

0.3 mL of trifluoroborane-dimethylsulfide complex in 10 mL of dichloromethane is added to a solution of the compounds obtained in Step 1, dissolved in 15 mL of dichloromethane (respectively 0.32 g of N-isopropyl, 0.4 g of N-cyanomethyl and 0.4 g of N-propargyl). The mixture is stirred at rt for 6 h and poured into a saturated aqueous sodium bicarbonate solution and extracted with ethyl acetate. The organic layer is dried over magnesium sulfate, filtered and evaporated. The crude product is purified by chromatography over silica gel while eluting with 70/30 heptane/ethyl acetate mixture.

Example 17

4-[2,5-Dioxo-4-hydroxymethyl-3-(1-methylethyl)-4-phenylimidazolidin-1-yl]-2-trifluoromethylbenzonitrile

Step 1: 4-[2,5-Dioxo-3-(1-methylethyl)-4-phenyl-4-[(2-propenyloxy)methyl]imidazolidin-1-yl]-2-trifluoromethylbenzonitrile TLC: Fr=0.65 (heptane/ethyl acetate 50/50)

δ $^1$H NMR (CDCl$_3$): 1.41 (d, 3H); 1.50 (d, 3H); 3.37 (dt, 1H); 4.12 (d, 1H); 4.13 (sl, 2H); 4.42 (d, 1H); 5.25 (d, 1H);

5.32 (d, 1H); 5.87 (ddt, 1H); 7.35 (m, 2H); 7.48 (m, 3H); 7.93 (d, 1H); 8.01 (d, 1H); 8.15 (m, 1H)
LCMS: (Rt=3.71 min): 457+ (M+)

Step 2: 4-[2,5-Dioxo-4-hydroxymethyl-3-(1-methylethyl)-4-phenylimidazolidin-1-yl]-2-trifluoromethylbenzonitrile TLC: Fr=0.45 (heptane/ethyl acetate 50/50)
δ $^1$H NMR (CDCl$_3$): 1.41 (d, 3H); 1.53 (d, 3H); 3.40 (dt, 1H); 4.30 (d, 1H); 4.72 (d, 1H); 7.37 (m, 2H); 7.48 (m, 3H); 7.93 (d, 1H); 8.06 (d, 1H); 8.20 (br s, 1H)
LCMS: (Rt=3.37 min): 386−(M−CH$_2$OH−)

Example 18

4-[2,5-Dioxo-3-cyanomethyl-4-hydroxymethyl-4-phenylimidazolidin-1-yl]-2-trifluoromethylbenzonitrile Step 1: 4-[3-Cyanomethyl-2,5-dioxo-4-phenyl-4-[(2-propenyloxy)methyl]imidazolidin-1-yl]-2-trifluoromethylbenzonitrile TLC: Fr=0.25 (heptane/ethyl acetate 50/50)
δ $^1$H NMR (CDCl$_3$): 4.09 (d, 1H); 4.20 (m, 3H); 4.47 (d, 1H); 4.60 (d, 1H); 5.29 (d, 1H); 5.33 (d, 1H); 5.92 (ddt, 1H); 7.38 (m, 2H); 7.53 (m, 3H); 7.98 (br s, 2H); 8.11 (br s, 1H)
LCMS: (Rt=3.39 min): not ionisable Step 2: 4-[2,5-Dioxo-3-cyanomethyl-4-hydroxymethyl-4-phenylimidazolidin-1-yl]-2-trifluoromethylbenzonitrile TLC: Fr=0.35 (heptane/ethyl acetate 50/50)
δ $^1$H NMR (CDCl$_3$): 4.10 (d, 1H); 4.46 (d, 1H); 4.69 (d, 1H); 4.77 (d, 1H); 7.36 (m, 2H); 7.53 (m, 3H); 7.98 (d, 1H); 8.01 (d, 1H); 8.12 (br s, 1H)
LCMS: (Rt=3.12 min): 383−(M−CH$_2$OH−)

Example 19

4-[2,5-Dioxo-4-hydroxymethyl-4-phenyl-3-(2-propynyl)imidazolidin-1-yl]-2-trifluoromethylbenzonitrile Step 1: 4-[2,5-Dioxo-4-phenyl-4-[(2-propenyloxy)methyl]-3-(2-propynyl)imidazolidin-1-yl]-2-trifluoromethylbenzonitrile TLC: Fr=0.65 (heptane/ethyl acetate 50/50)
δ $^1$H NMR (CDCl$_3$): 2.27 (m, 1H); 4.06 (dd, 1H); 4.14 (m, 2H); 4.22 (d, 1H); 4.40 (dd, 1H); 4.46 (d, 1H); 5.26 (d, 1H); 5.31 (d, 1H); 5.91 (ddt, 1H); 7.41 (m, 2H); 7.49 (m, 3H); 7.94 (d, 1H); 8.01 (dd, 1H); 8.14 (br s, 1H)
LCMS: (Rt=3.45 min): not ionisable Step 2: 4-[2,5-Dioxo-4-hydroxymethyl-4-phenyl-3-(2-propynyl)imidazolidin-1-yl]-2-trifluoromethylbenzonitrile TLC: Fr=0.40 (heptane/ethyl acetate 50/50)
δ $^1$H NMR (CDCl$_3$): 2.48 (m, 1H); 3.83 (dd, 1H); 4.48 (d, 1H); 4.73 (d, 1H); 4.81 (dd, 1H); 7.46 (m, 2H); 7.51 (m, 3H); 7.95 (d, 1H); 8.03 (d, 1H); 8.18 (br s, 1H)
LCMS: (Rt=3.16 min): 382−(M−CH$_2$OH−)

Example 20

4-[2,5-Dioxo-4-hydroxymethyl-4-phenylimidazolidin-1-yl]-2-trifluoromethylbenzonitrile (Method A)

Step 1: 4-[2,5-Dioxo-4-phenyl-4-[(2-propenyloxy)methyl]imidazolidin-1-yl]-2-trifluoromethylbenzonitrile To a solution of 0.47 g of 4-phenyl-4-[(2-propenyloxy)methyl]imidazolidine-2,5-dione in 30 mL of DMF is added 0.28 g of copper (I) oxide and 0.81 g of 4-bromo-2-trifluoromethylbenzonitrile. The mixture is warmed at 135° C. for 20 hours then it is evaporated to dryness. The crude product is diluted with a 20% aqueous solution of ammonia and extracted with ethyl acetate. The organic layer is dried over magnesium sulfate, filtered and evaporated. The crude product is purified by chromatography over silica gel while eluting with 70/30 heptane/ethyl acetate.
TLC: Fr=0.30 (heptane/ethyl acetate 7/−30)
δ $^1$H NMR (CDCl$_3$): 3.86 (d, 1H); 4.14 (br s, 2H); 4.27 (d, 1H); 5.28 (d, 1H); 5.32 (d, 1H); 5.89 (ddt, 1H); 7.52 (m, 3H); 7.70 (m, 2H); 7.98 (m, 2H); 8.14 (m. 1H)
LCMS: (Rt=6.91 min): 414−(M−H−)

Step 2: 4-[2,5-Dioxo-4-hydroxymethyl-4-phenylimidazolidin-1-yl]-2-trifluoromethylbenzonitrile To a solution of 0.18 g 4-[2,5-dioxo-4-phenyl-4-[(2-propenyloxy)methyl]imidazolidin-1-yl]-2-trifluoromethylbenzonitrile in 15 mL of DCM is added 0.2 mL of trifluoroborane-dimethylsulfide complex in 10 mL of dichloromethane. The mixture is stirred at rt for 6 hours and poured into a saturated aqueous sodium bicarbonate solution and extracted with ethyl acetate. The organic layer is dried over magnesium sulfate, filtered and evaporated. The crude product is purified by chromatography over silica gel while eluting with 70/30 heptane/ethyl acetate mixture.
TLC: Fr 0.25 (heptane/ethyl acetate 50/50)
δ $^1$H NMR (CDCl$_3$): 3.99 (d, 1H); 4.42 (d, 1H); 7.11 (br s, 1H); 7.49 (m, 3H); 7.64 (m, 2H); 7.94 (m, 2H); 8.10 (br s, 1H)
LCMS: (Rt=3.02 min): 344−(M−CH$_2$OH−)

Example 21

4-[2,5-Dioxo-4-hydroxymethyl-3-methyl-4-(3-methylphenyl)imidazolidin-1-yl]-2-trifluoromethyl-benzonitrile (Method A)

Step 1: 2-bromo-1-(3-methylphenyl)ethanone

To a solution of 1-(3-methylphenyl)ethanone (2 g) in ethyl ether (20 mL) is added bromine (726 μL) at 0° C. The mixture is treated with an aqueous solution of sodium bicarbonate, extracted with ethyl ether, dried over magnesium sulfate, concentrated and purified on silica gel (ethyl acetate/cyclohexane 0/100) to give the desired compound.
TLC: Fr=0.42 (ethyl acetate/cyclohexane 10/90).
δ $^1$H NMR (CDCl$_3$): 2.47 (s, 3H); 4.49 (s, 2H); 7.40-7.47 (m, 2H); 7.81-7.91 (m, 2H).
LCMS: (Rt=3.42 min): not ionisable.

Step 2: 2-hydroxy-1-(3-methylphenyl)ethanone

A solution of 2-bromo-1-(3-methylphenyl)ethanone (1 g) in acetonitrile (2.5 mL) and water (13 mL) is treated under microwave irradiation (125° C., 50 min) The same experiment is repeated three times. All the vials are collected, extracted with DCM, dried over magnesium sulfate and concentrated under vacuum to give the desired compound.

TLC: Fr=0.15 (ethyl acetate/cyclohexane: 10/90).

δ $^1$H NMR (CDCl$_3$): 2.47 (s, 3H); 4.90 (s, 2H); 7.41-7.49 (m, 2H); 7.74-7.78 (m, 2H).

Step 3 2-[(2-propenyloxy)methyl]-1-(3-methylphenyl)ethanone

To a solution of 2-hydroxy-1-(3-methylphenyl)ethanone (1.95 g) in allyl bromide (10 mL) is added calcium sulfate (7.9 g) and silver oxide (5.1 g). The mixture is stirred under argon and dark during 2 hours. The mixture is diluted with ethyl acetate, filtered on celite, concentrated and purified on silica gel (ethyl actetate/cyclohexane 0/100 to 15/85) to give the desired compound.

TLC: Fr=0.54 (ethyl acetate/cyclohexane: 30/70)

δ $^1$H NMR (CDCl$_3$): 2.45 (s, 3H); 4.20 (d, 2H); 4.79 (s, 2H); 5.29 (d, 1H); 5.37 (d, 1H); 5.96-6.04 (m, 1H); 7.37-7.45 (m, 2H); 7.75-7.79 (m, 2H).

LCMS: (Rt=3.30 min): not ionisable.

Step 4: 4-[(2-propenyloxy)methyl]-4-(3-methylphenyl)imidazolidine-2,5-dione

To a solution of 2-[(propenyloxy)methyl]-1-(3-methylphenyl)ethanone (690 mg) in ethanol (5 mL) and water (5 mL) is added potassium cyanide (472 mg) and ammonium carbonate (2.44 g). The mixture is refluxed overnight at 55° C. The mixture is extracted with ethyl acetate, dried over magnesium sulfate and concentrated under vacuum to give the desired compound.

δ $^1$H NMR (CDCl$_3$): 2.41 (s, 3H); 3.78 (d, 1H); 4.06-4.09 (m, 3H); 5.22-5.30 (m, 2H); 5.81-5.90 (m, 1H); 5.94 (s, 1H); 7.21-7.39 (m, 4H); 7.61 (s, 1H).

LCMS: (Rt=2.97 min): not ionisable.

Step 5: 4-[2,5-dioxo-4-(3-methylphenyl)-4-[(2-propenyloxy)methyl]imidazolidin-1-yl]-2-trifluoromethylbenzonitrile To a solution of 4-[(2-propenyloxy)methyl]-4-(3-methylphenyl)imidazolidine-2,5-dione (899 mg) and 4-bromo-2-(trifluoromethyl)benzonitrile (863 mg) in DMAC (5 mL) is added copper (I) oxide (395 mg). The mixture is refluxed overnight at 130° C. The mixture is concentrated, taken in ethyl acetate, washed with a 10% aqueous ammonia solution and brine. The organic phase is dried over magnesium sulfate, concentrated under vacuum and purified on silica gel (ethyl acetate/cyclohexane 0/100 to 50/50) to give the desired compound.

TLC: Fr=0.30 (ethyl acetate/cyclohexane 30/70).

δ $^1$H NMR (CDCl$_3$): 2.44 (s, 3H); 3.80 (d, 1H); 4.10 (m, 2H); 4.22 (d, 1H); 5.23-5.30 (m, 2H); 5.83-5.90 (m, 1H); 6.37 (s, 1H); 7.26-7.45 (m, 4H); 7.93-7.98 (s, 2H); 8.11 (s, 1H).

LCMS: (Rt=3.43 min): 428−(M−H)$^-$.

Step 6: 4-[2,5-Dioxo-3-methyl-4-(3-methylphenyl)-4-[(2-propenyloxy)methyl]imidazolidin-1-yl]-2-trifluoromethylbenzonitrile To a solution of 4-[2,5-dioxo-4-(3-methylphenyl)-4-[(2-propenyloxy)methyl]imidazolidin-1-yl]-2-trifluoromethylbenzonitrile (829 mg) in DMF (1.5 mL) is added potassium carbonate (320 mg) and methyliodide (480 μL). The mixture is stirred 3 hours at rt, evaporated, washed with brine, extracted with ethyl acetate, dried over MgSO$_4$ and concentrated to give the desired compound.

TLC: Fr=0.43 (ethyl acetate/cyclohexane 30/70).

δ $^1$H NMR (CDCl$_3$): 2.43 (s, 3H); 3.04 (s, 3H); 3.97 (d, 1H); 4.14 (m, 2H); 4.42 (d, 1H); 5.25-5.34 (m, 2H); 5.85-5.91 (m, 1H); 7.17 (m, 2H); 7.26-7.28 (m, 1H); 7.93 (d, 2H); 8.01 (d, 1H); 8.15 (s, 1H).

LCMS: (Rt=4.01 min): not ionisable.

Step 7: 4-[2,5-Dioxo-4-hydroxymethyl-3-methyl-4-(3-methylphenyl)imidazolidin-1-yl]-2-trifluoromethylbenzonitrile To a solution of 856 mg of 4-[2,5-dioxo-3-methyl-4-(3-methylphenyl)-4-[(2-propenyloxy)methyl]imidazolidin-1-yl]-2-trifluoromethylbenzonitrile in DCM (5 mL) is added trifluoroborane-dimethylsulfide complex (812 μL). The mixture is stirred 4 hours at rt, diluted with DCM, washed with an aqueous solution of sodium bicarbonate, dried over magnesium sulfate, concentrated and purified on silica gel (ethyl acetate/cyclohexane 0/100 to 50/50) to give the desired compound.

TLC: Fr=0.76 (ethyl acetate/cyclohexane: 50/50).

δ $^1$H NMR (CDCl$_3$): 2.44 (s, 3H); 3.09 (s, 3H); 4.17 (d, 1H); 4.72 (d, 1H); 7.17 (m, 2H); 7.28 (m, 1H); 7.39 (m, 1H); 7.93 (d, 1H); 8.03 (d, 1H); 8.18 (s, 1H).

LCMS: (Rt=3.19 min): 372−(M−CH$_2$OH)−.

Example 22

4-[4-(4-(2-Chlorophenyl)-2,5-dioxo-4-hydroxymethyl-3-methylimidazolidin-1-yl]-2-trifluoromethylbenzonitrile Using the protocol described in Example 6, step 6, reacting 0.80 g of 4-[4-(2-chlorophenyl)-2,5-dioxo-3-methyl-4-[(2-prop enyloxy)methyl]imidazolidin-1-yl]-2-trifluoromethylbenzonitrile yields the desired compound.

δ $^1$H NMR (DMSO D$_6$): 2.69 (s, 3H); δ 4.25 (m, 1H); 4.46 (m, 1H); 5.90 (t, 1H); 7.50 (m, 3H); 7.58 (m, 2H); 8.05 (m, 2H), 8.35 (d, 1H).

LCMS: (Rt=3.47 min): (392/394)−(M−CH$_2$OH−).

Example 23

[1-(4-cyano-3-trifluoromethylphenyl)-2,5-dioxo-3-methyl-4-phenylimidazolidin-4-yl]methyl hydrogen sulfate A solution of 0.39 g of 4-[3-methyl-4-hydroxymethyl-2,5-dioxo-4-phenylimidazolidin-1-yl]-2-trifluoromethylbenzonitrile and 0.48 g of sulphur trioxide-pyridine complex in 20 mL of pyridine is refluxed for 18 hours then evaporated to dryness. The crude product is purified by chromatography over silica gel while eluting with 90/10/1/1 DCM/methanol/acetic acid/water mixture.

TLC: Fr=0.25 (DCM/methanol/acetic acid/water 90/10/1/1).

δ $^1$H NMR (CD$_3$OD): 3.09 (NCH$_3$); 4.69 (d, 1H); 5.03 (d, 1H); 7.54 (m, 5H); 8.13 (m, 2H); 8.25 (sl, 1H)

LCMS: (Rt=3.52 min): 468−(M−H−). .

Example 24

[1-(4-Cyano-3-trifluoromethylphenyl)-2,5-dioxo-3-methyl-4-phenylimidazolidin-4-yl]methyl dihydrogen phosphate

Step 1: [1-(4-Cyano-3-trifluoromethylphenyl)-2,5-dioxo-3-methyl-4-phenylimidazolidin-4-yl]methyl diethyl phosphate A solution of 0.4 g of 4-[3-methyl-4-hydroxymethyl-2,5-dioxo-4-phenylimidazolidin-1-yl]-2-trifluoromethylbenzonitrile in 2 mL of pyridine and 0.2 mL of diethyl phosphate is stirred for 3 hours at rt under argon atmosphere. The mixture is quenched with 2M aqueous hydrochloric acid and extracted with diethyl ether and ethyl acetate. The crude product is purified by chromatography over silica gel while eluting with 4/1 DCM/ethyl acetate mixture.

TLC: Fr=0.7 (4/1 DCM/ethyl acetate).

$\delta$ $^1$H NMR (CD$_3$OD): 1.31 (q, 6H); 3.03 (s, 3H); 4.15 (m, 4H); 4.83 and 5.07 (2m, 2H); 7.45-7.55 (m, 5H); 8.06 (m, 1H); 8.15 (m, 2H).

LCMS: (Rt=3.76 min): 526+ (MH+).

Step 2: [1-(4-Cyano-3-trifluoromethylphenyl)-2,5-dioxo-3-methyl-4-phenylimidazolidin-4-yl]methyl dihydrogen phosphate Under argon atmosphere, 1 mL of bromotrimethylsilane is added to a solution of 0.39 g of 1-(4-cyano-3-trifluoromethylphenyl)-2,5-dioxo-3-methyl-4-phenylimidazolidin-4-yl]methyl diethyl phosphate in 10 mL of DCM cooled at 0° C. The reaction is stirred for 1 hour at 0° C. then 18 hours at rt. The solvent is evaporated then the residue is dissolved in a mixture of water and ethanol. Solvents are evaporated and this process repeated twice. The crude product is purified by chromatography over silica gel while eluting with 85/15/1/1 DCM/methanol/acetic acid/water mixture to provide 0.25 g of white solid. After washing with a diethyl ether/pentane mixture, the desired compound is obtained.

$\delta$ $^1$H NMR (DMSO D$_6$): 2.90 (s, 3H); 4.58 and 4.70 (m, 2H); 7.49 (m, 5H); 8.04 (d, 1H); 8.20 (s, 1H); 8.35 (d, 1H).

LCMS: (Rt=2.46 min): 468−(M−H−).

Example 25

[1-(4-Cyano-3-trifluoromethylphenyl)-2,5-dioxo-3-methyl-4-phenylimidazolidin-4-yl]methoxy-3-methyl-1-oxobutan-2-aminium chloride

Step 1: (2S)-2-[(1,1-Dimethylethoxy)carbonylamino]-3-methylbutanoic acid [1-(4-cyano-3-trifluoromethylphenyl)-2,5-dioxo-3-methyl-4-phenylimidazolidin-4-yl]methyl ester A solution of 0.3 g of 4-[2,5-dioxo-4-(hydroxymethyl)-3-methyl-4-phenylimidazolidin-1-yl]-2-trifluoromethylbenzonitrile, 0.217 g of (2S)-2-[(1,1-dimethylethoxy)carbonylamino]-3-methylbutanoic acid, 0.122 g of 4-dimethylamino pyridine and 0.3 g of 1-(3-dimethylaminopropyl)-3-ethylcarbodiimide hydrochloride in 50 mL of dichloromethane is stirred for 18 hours then poured into water and extracted with ethyl acetate. The organic layer is dried over magnesium sulfate, filtered and evaporated. The crude product is purified by chromatography over silica gel while eluting with 70/30 heptane/ethyl acetate mixture to provide the desired compound.

TLC: Fr=0.20 (heptane/ethyl acetate 70/30).

LCMS: (Rt=4.07 min): 489+ (M−tBuOCO+H+).

Step 2: [1-(4-Cyano-3-trifluoromethylphenyl)-2,5-dioxo-3-methyl-4-phenylimidazolidin-4-yl]methoxy-3-methyl-1-oxobutan-2-aminium chloride 2 mL of trifluoroacetic acid are added to a solution of 0.43 g of (2S)-2-[(1,1-dimethylethoxy)carbonylamino]-3-methylbutanoic acid [1-(4-cyano-3-trifluoromethylphenyl)-2,5-dioxo-3-methyl-4-phenylimidazolidin-4-yl]methyl ester in 20 mL of dichloromethane. The mixture is stirred at 25° C. for 2 hours then the solvent is evaporated to dryness. The crude product is diluted with a saturated aqueous sodium bicarbonate solution and extracted with ethyl acetate. The organic layer is dried over magnesium sulfate, filtered and evaporated.

The crude product is dissolved in 100 mL of dichloromethane/ethyl ether mixture (5/95) and 0.4 mL of a 2M hydrogen chloride solution in ethyl ether is added. After filtration, the desired compound is obtained.

TLC: Fr=0.2 (dichloromethane/methanol 95/5).

$\delta$ $^1$H NMR (CD$_3$OD): 1.06 (m, 6H); 2.25 (m, 1H); 3.07 (d, 3H); 4.12 (m, 1H); 4.75 (dd, 1H); 4.88 (t, 1H); 7.58 (m, 5H); 8.19 (m, 2H); 8.26 (m, 1H).

LCMS: (Rt=2.8 min): 489+ (M+H+).

Example 26

[1-(4-Cyano-3-trifluoromethylphenyl)-2,5-dioxo-3-methyl-4-phenylimidazolidin-4-yl]methoxy-4-oxobutanoic acid To a solution of 0.20 g of 4-[3-methyl-4-hydroxymethyl-2,5-dioxo-4-phenylimidazolidin-1-yl]-2-trifluoromethylbenzonitrile in 3 mL of pyridine was added 6 mg of dimethylaminopyridine and 0.052 g of succinic anhydride. The mixture is stirred for 12 hours then evaporated to dryness. The crude product is washed with water and extracted with DCM. The organic layer is dried over magnesium sulfate, filtered and evaporated. The crude product is purified by chromatography over silica gel while eluting with 50/50 cyclohexane/ethyl acetate to give the desired compound.

TLC: Fr=0.17 (cyclohexane/ethyl acetate 50/50)

$\delta$ $^1$H NMR (CDCl$_3$): 2.67-2.72 (m, 4H); 3.02 (s, 3H); 4.92 (d, 1H); 5.03 (d, 1H); 7.39 (m, 2H); 7.53 (m, 3H); 7.96 (d, 1H); 8.04 (dd, 1H); 8.18 (d, 1H).

LCMS: (Rt=3.49 min): 358−(M−H−CH$_2$O—C$_4$H$_4$O$_3$).

Example 27

(S)-[1-(4-Cyano-3-trifluoromethylphenyl)-2,5-dioxo-3-methyl-4-phenylimidazolidin-4-yl]methyl dihydrogen phosphate

Step 1: (S)-[1-(4-Cyano-3-trifluoromethylphenyl)-2,5-dioxo-3-methyl-4-phenylimidazolidin-4-yl]methyl diethyl phosphate A solution of 1.2 g of (S)-4-[3-methyl-4-hydroxymethyl-2,5-dioxo-4-phenylimidazolidin-1-yl]-2-trifluoromethylbenzonitrile in 6 mL of pyridine and 0.6 mL of diethyl chlorophosphate is stirred for 48 hours at room temperature under argon atmosphere. The mixture is quenched with 2M aqueous hydrochloric acid and extracted with ethyl acetate. The crude product is purified by chromatography over silica gel while eluting with 1/1 heptane/ethyl acetate mixture.

TLC: Fr=0.12 (1/1 heptane/ethyl acetate).

δ $^1$H NMR (CDCl$_3$): 1.45 (m, 6H); 1.75 (sl, 1H); 3.10 (s, 3H); 4.13 (m, 4H); 4.65 (q, 1H); 5.02 (q, 1H); 7.37 (m, 2H); 7.51 (m, 3H); 7.95 (d, 1H); 8.0 (dd, 1H); 8.13 (sl, 1H).

LCMS: (Rt=4.66 min): 526+ (MH+).

[α]$_D$=−44.8° (c=1%, EtOH).

Step 2: (S)-[1-(4-Cyano-3-trifluoromethylphenyl)-2,5-dioxo-3-methyl-4-phenylimidazolidin-4-yl]methyl dihydrogen phosphate Under argon atmosphere, 2.5 mL of bromotrimethylsilane is added to a solution of 0.80 g of (S)-[1-(4-cyano-3-trifluoromethylphenyl)-2,5-dioxo-3-methyl-4-phenylimidazolidin-4-yl]methyl diethyl phosphate in 25 mL of DCM cooled at 0° C. The reaction is stirred for 1 hour at 0° C. then 18 hours at room temperature. The solvent is evaporated then the residue is dissolved in a mixture of water and methanol. Solvents are evaporated and this process repeated twice. The crude product is purified by chromatography over silica gel while eluting with 90/10/1/1 to 85/15/2/2 dichloromethane/methanol/acetic acid/water mixture to provide the desired compound.

TLC: Fr=0.12 (85/15/2/2 dichloromethane/methanol/acetic acid/water).

δ $^1$H NMR (CD$_3$OD): 2.00 (m, 2H); 3.09 (m, 2H); 3.37 (sl, 3H); 4.51 (dl, 1H); 4.91 (dl under water peak), 1H); 7.53 (m, 5H); 816 (m, 2H); 8.27 (m, 1H).

LCMS: (Rt=2.50 min): 470+ (M+H+).

[α]$_D$=−47.6° (c=1.05%, EtOH).

Example 28

(S)-[1-(4-Cyano-3-trifluoromethylphenyl)-2,5-dioxo-3-methyl-4-phenylimidazolidin-4-yl]methoxy-4-oxobutanoic acid To a solution of 0.60 g of (S)-4-[3-methyl-4-hydroxymethyl-2,5-dioxo-4-phenylimidazolidin-1-yl]-2-trifluoromethylbenzonitrile in 24 mL of pyridine was added 19 mg of dimethylaminopyridine and 1.54 g of succinic anhydride. The mixture is stirred at 110° C. for 7 hours then evaporated to dryness. The crude product is washed with water and extracted with dichloromethane. The organic layer is dried over magnesium sulfate, filtered and evaporated. The crude product is purified by chromatography over silica gel while eluting with 50/50 heptane/ethyl acetate to give the desired compound.

TLC: Fr=0.17 (cyclohexane/ethyl acetate 50/50)

δ $^1$H NMR (CDCl$_3$): 2.67-2.74 (m, 4H); 3.02 (s, 3H); 4.92 (d, 1H); 5.03 (d, 1H); 7.38 (m, 2H); 7.52 (m, 3H); 7.96 (d, 1H); 8.04 (dd, 1H); 8.18 (d, 1H).

LCMS: (Rt=3.22 min): 358−(M−H−CH$_2$O−C$_4$H$_4$O$_3$).

Example 29

(S)-((S)-1-(4-Cyano-3-(trifluoromethyl)phenyl)-3-methyl-2,5-dioxo-4-phenylimidazolidin-4-yl)methyl-3-methylbutanoate-2-ammonium chloride Step 1: (2S)-2-[(1,1-Dimethylethoxy)carbonylamino]-3-methylbutanoic acid (S)-[7-(4-cyano-3-trifluoromethylphenyl)-2,5-dioxo-3-methyl-4-phenylimidazolidin-4-yl]methyl ester A solution of 0.45 g of (S)-4-[2,5-dioxo-4-(hydroxymethyl)-3-methyl-4-phenylimidazolidin-1-yl]-2-trifluoromethylbenzonitrile, 0.33 g of (2S)-2-[(1,1-dimethylethoxy)carbonylamino]-3-methylbutanoic acid, 0.185 g of 4-dimethylamino pyridine and 0.45 g of 1-(3-dimethylaminopropyl)-3-ethylcarbodiimide hydrochloride in 70 mL of dichloromethane is stirred for 1 hour then poured into water and extracted with ethyl acetate. The organic layer is dried over magnesium sulfate, filtered and evaporated. The crude product is purified by chromatography over silica gel while eluting with 70/30 heptane/ethyl acetate mixture to provide the desired compound.

TLC: Fr=0.20 (heptane/ethyl acetate 70/30).

δ $^1$H NMR (CDCl$_3$): 0.89 and 0.97 (2d, 6H); 1.46 (s, 9H); 2.05 (m, 1H); 3.02 (s, 3H); 4.22 (m, 1H); 4.93 (m, 2H); 5.04 (m, 1H); 7.38 (m, 2H); 7.52 (m, 3H); 7.96 (d, 1H); 8.04 (dl, 1H); 8.15 (sl, 1H).

LCMS: (Rt=3.90 min): 489+ (M−tBuOCO+H+).

[α]$_D$=−54.7° (c=1.25%, EtOH).

Step 2: (S)-[7-(4-Cyano-3-trifluoromethylphenyl)-2,5-dioxo-3-methyl-4-phenylimidazolidin-4-yl]methoxy-3-methyl-1-oxobutan-2-aminium chloride 3 mL of trifluoroacetic acid are added to a solution of 0.65 g of (2S)-2-[(1,1-dimethylethoxy)carbonylamino]-3-methylbutanoic acid (S)-[1-(4-cyano-3-trifluoromethylphenyl)-2,5-dioxo-3-methyl-4-phenylimidazolidin-4-yl]methyl ester in 30 mL of dichloromethane. The mixture is stirred at room temperature for 5 hours, 20 mL of toluene are added then the solvent is evaporated to dryness. The crude product is diluted with a saturated aqueous sodium bicarbonate solution and extracted with ethyl acetate. The organic layer is dried over magnesium sulfate, filtered and evaporated. The crude product is dissolved in 120 mL of dichloromethane/ethyl ether mixture (10/90) and 0.75 mL of a 2M hydrogen chloride solution in ethyl ether is added. After filtration, the desired compound is obtained TLC: Fr=0.2 (dichloromethane/methanol 95/5).

δ $^1$H NMR (CD$_3$OD): 1.07 and 1.10 (2d, 6H); 2.26 (m, 1H); 3.07 (s, 3H); 4.11 (d, 1H); 5.22 and 5.36 (2d, 2H); 7.58 (m, 5H); 8.19 (AB, 2H); 8.25 (sl, 1H). [α]$_D$=−46.7° (c=1.08%, EtOH).

Example 30

4-[2,5-Dioxo-4-hydroxymethyl-3-methyl-4-phenylimidazolidin-1-yl]-2-methoxybenzonitrile Step 1: 4-[2,5-Dioxo-4-hydroxymethyl-4-phenylimidazolidin-1-yl]-2-methoxybenzonitrile A solution of 384 mg of 4-cyano-3-methoxyphenyl isocyanate (prepared according to WO 2007/137874) in 8 mL dioxane is added to a solution of 200 mg of 2-hydroxymethyl-2-phenylglycine (prepared according to literature procedure) in an aqueous solution of 1.8 mL 1N sodium hydroxide in 2 mL of water. The mixture is stirred at room temperature overnight, acidified by adding 3 mL 12N HCl and heated at 110° C. for 2 hours. The solution is then treated with a saturated aqueous solution of sodium bicarbonate, extracted with ethyl acetate, dried over sulfate magnesium, filtered, evaporated and purified over silica gel while eluting with 60/40 heptane/ethyl acetate mixture to give the expected product.

TLC: Fr=0.30 (heptane/ethyl acetate 50/50).

δ $^1$H NMR (CDCl$_3$): 3.98 (s, 3H); 4.06 and 4.40 (2d, 2H); 6.07 (bs, 1H); 7.23 (m, 2H); 7.51 (m, 3H); 7.66 (m, 3H)

LCMS: (Rt=5.44 min): 306−(M−CH$_2$OH)−..

Step 2: 4-[2,5-Dioxo-4-hydroxymethyl-3-methyl-4-phenylimidazolidin-1-yl]-2-methoxybenzonitrile 173 mg potassium carbonate and 86 μL methyl iodide are added to a solution of 141 mg 4-[2,5-dioxo-4-hydroxymethyl-4-phenylimidazolidin-1-yl]-2-methoxybenzonitrile in 2 mL DMF. The mixture is stirred overnight at room temperature, evaporated to dryness, The residue is taken in water and extracted with ethyl acetate. The organic layer is dried over magnesium sulfate, filtered, evaporated and chromatographed over silica gel while eluting with 70/30 heptane/ethyl acetate mixture to give the expected product.

δ $^1$H NMR (CDCl$_3$): δ 3.09 (s, 3H); 3.97 (s, 3H); 4.17 and 4.72 (2d, 2H); 7.27 (m, 2H); 7.40 (m, 2H); 7.50 (m, 3H); 7.64 (m, 1H).

LCMS: (Rt=5.67 min): not ionisable.

Example 31

(S)-1-(3,4-Dichlorophenyl)-4-hydroxymethyl-3-methyl-4-phenylimidazolidine-2,5-dione Step 1: (S)-1-(3,4-Dichlorophenyl)-4-hydroxymethyl-4-phenylimidazolidine-2,5-dione 217 mg of (S)-2-hydroxymethyl-2-phenylglycine (prepared according to A.Olma, Polish J. Chem., 70, (1996), 1442-1447) are dissolved in 5 mL of 0.5 N aqueous sodium hydroxide. 300 mg of 3,4-dichlorophenyl isocyanate dissolved in 5 mL dioxan are slowly added over 10 min then the mixture is stirred for 1 h, the pH is around 7 to 7.5. 3 mL of 0.5 N aqueous sodium hydroxide are added to make the pH alkaline then 300 mg of 3,4-dichlorophenyl isocyanate dissolved in 5 mL dioxan are slowly added again. The mixture is stirred for 1 further hour at room temperature then 12N hydrochloric acid is added to acidic pH and the mixture is heated for 1 h at reflux temperature. The dioxan is removed by evaporation under vacuum, the aqueous phase is extracted with ethyl acetate. The extracts are washed with brine, dried over magnesium sulfate and evaporated to dryness. The residue is purified over silica gel while eluting with a gradient mixture from heptane to pure ethyl acetate to provide expected product.

[α]$_D$=−13.3° (c=1.02%, MeOH).

Step 2: (S)-1-(3,4-Dichlorophenyl)-4-hydroxymethyl-3-methyl-4-phenylimidazolidine-2,5-dione 150 mg of (S)-1-(3,4-Dichlorophenyl)-4-hydroxymethyl-4-phenylimidazolidine-2,5-dione are dissolved in 5 mL of dimethylformamide then 165 mg of potassium carbonate are added followed by 137 μL of dimethylsulfate. The mixture is stirred overnight at room temperature then it is taken in a mixture of water and ethyl acetate. The aqueous phase is extracted with ethyl acetate. The extracts are washed with brine, dried over magnesium sulfate and evaporated to dryness. The residue is purified over silica gel while eluting with a gradient mixture from heptane to pure ethyl acetate to provide the expected product.

δ $^1$H NMR (CDCl$_3$): 3.04 (s, 3H); 4.11 and 4.65 (2d, 2H); 7.37 (m, 3H); 7.51 (m, 4H); 7.66 (d, 1H).

LCMS: (Rt=3.16 min): 364/366+ (MH+); 333/335−(M−CH$_2$OH)−.

[α]$_D$=−38.5° (c=0.925%, EtOH).

TABLE 1

Representative compounds of the invention

| ID | Structure | Name | Calc'd MW |
|----|-----------|------|-----------|
| 1 | 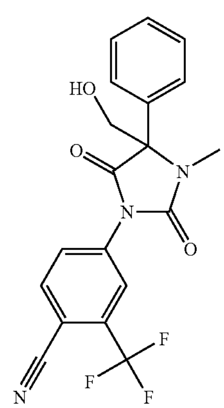 | 4-[2,5-Dioxo-4-(hydroxymethyl)-3-methyl-4-phenylimidazolidin-1-yl]-2-trifluoromethylbenzonitrile | 389.3 |

TABLE 1-continued

Representative compounds of the invention

| ID | Structure | Name | Calc'd MW |
|----|-----------|------|-----------|
| 2 | 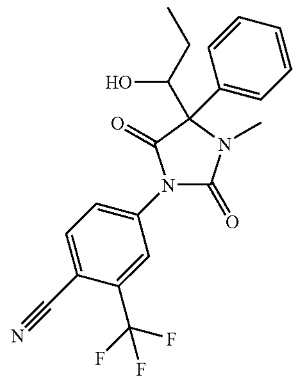 | 4-[2,5-Dioxo-4-(1-hydroxypropyl)-3-methyl-4-phenylimidazolidin-1-yl]-2-trifluoromethylbenzonitrile Isomer A | 417.4 |
| 3 | 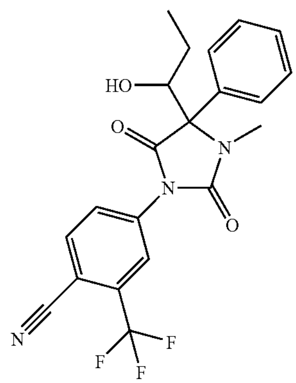 | 4-[2,5-Dioxo-4-(1-hydroxypropyl)-3-methyl-4-phenylimidazolidin-1-yl]-2-trifluoromethylbenzonitrile Isomer B | 417.4 |
| 4 | 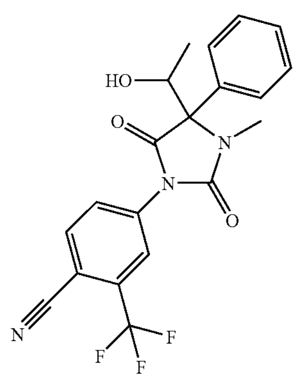 | 4-[2,5-Dioxo-4-(hydroxyethyl)-3-methyl-4-phenylimidazolidin-1-yl]-2-trifluoromethylbenzonitrile Isomer A | 403.4 |
| 5 | 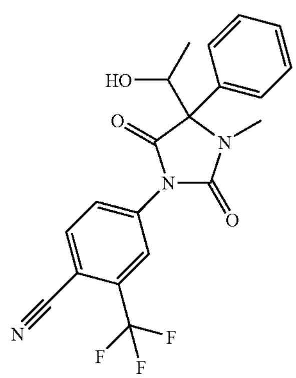 | 4-[2,5-Dioxo-4-(hydroxyethyl)-3-methyl-4-phenylimidazolidin-1-yl]-2-trifluoromethylbenzonitrile Isomer B | 403.4 |

TABLE 1-continued

Representative compounds of the invention

| ID | Structure | Name | Calc'd MW |
|----|-----------|------|-----------|
| 6 | 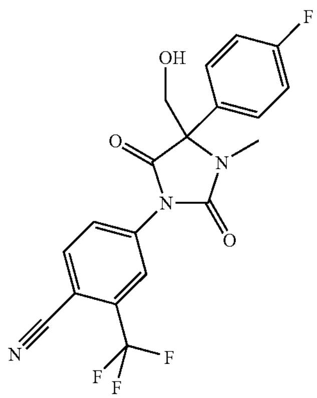 | 4-[2,5-Dioxo-4-(4-fluorophenyl)-4-(hydroxymethyl)-3-methylimidazolidin-1-yl]-2-trifluoromethylbenzonitrile | 407.3 |
| 7 | 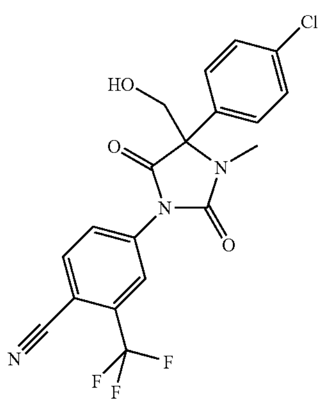 | 4-[4-(4-Chlorophenyl)-2,5-dioxo-4-hydroxymethyl-3-methyl-imidazolidin-1-yl)-2-trifluoromethylbenzonitrile | 423.8 |
| 8 | 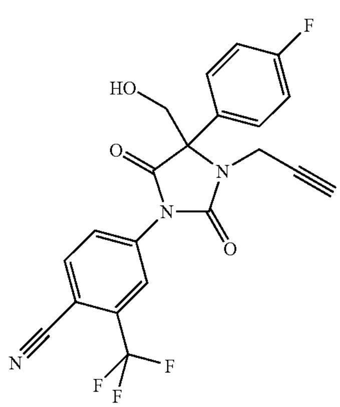 | 4-[2,5-Dioxo-4-(4-fluorophenyl)-4-hydroxymethyl-3-(2-propynyl)imidazolidin-1-yl]-2-trifluoromethylbenzonitrile | 431.3 |

TABLE 1-continued

Representative compounds of the invention

| ID | Structure | Name | Calc'd MW |
|----|-----------|------|-----------|
| 9 | 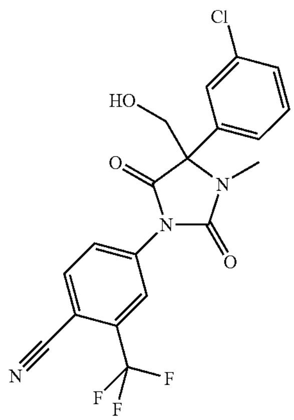 | 4-[4-(3-Chlorophenyl)-2,5-dioxo-4-hydroxymethyl-3-methyl-imidazolidin-1-yl)-2-trifluoromethylbenzonitrile | 423.8 |
| 10 | 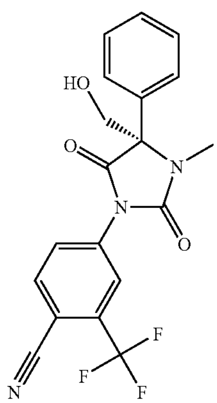 | (S)-4-[2,5-Dioxo-4-(hydroxymethyl)-3-methyl-4-phenylimidazolidin-1-yl]-2-trifluoromethylbenzonitrile | 389.3 |
| 11 | 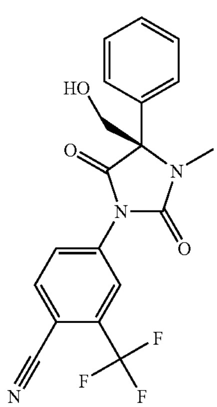 | (R)-4-[2,5-Dioxo-4-(hydroxymethyl)-3-methyl-4-phenylimidazolidin-1-yl]-2-trifluoromethylbenzonitrile | 389.3 |

TABLE 1-continued

Representative compounds of the invention

| ID | Structure | Name | Calc'd MW |
|---|---|---|---|
| 12 | 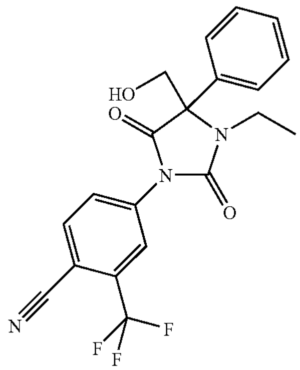 | 4-[2,5-Dioxo-3-ethyl-4-(hydroxymethyl)-4-phenylimidazolidin-1-yl]-2-trifluoromethylbenzonitrile | 403.4 |
| 13 | 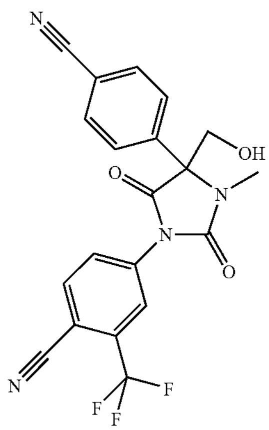 | 4-[4-(4-Cyanophenyl)-2,5-dioxo-4-hydroxymethyl-3-methylimidazolidin-1-yl)-2-trifluoromethylbenzonitrile | 414.3 |
| 14 | 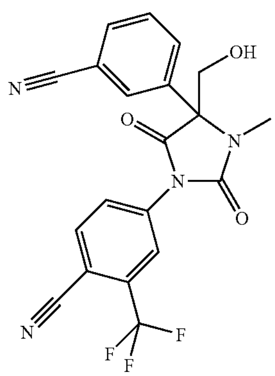 | 4-[4-(3-Cyanophenyl)-2,5-dioxo-4-hydroxymethyl-3-methylimidazolidin-1-yl)-2-trifluoromethylbenzonitrile | 414.3 |
| 15 | 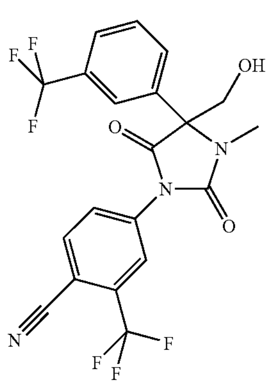 | 4-[2,5-Dioxo-4-hydroxymethyl-3-methyl-4-(3-trifluoromethylphenyl)imidazolidin-1-yl)-2-trifluoromethylbenzonitrile | 457.3 |

TABLE 1-continued

Representative compounds of the invention

| ID | Structure | Name | Calc'd MW |
|---|---|---|---|
| 16 | 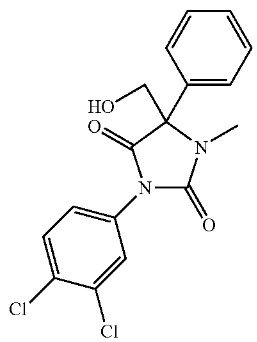 | 1-(3,4-Dichlorophenyl)-4-hydroxymethyl-3-methyl-4-phenylimidazolidine-2,5-dione | 365.2 |
| 17 | 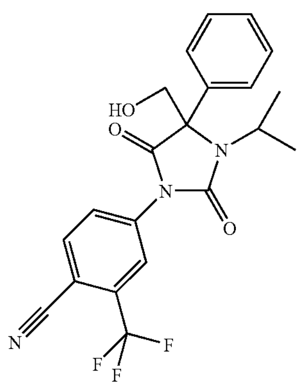 | 4-[2,5-Dioxo-4-(hydroxymethyl)-3-(1-methylethyl)-4-phenylimidazolidin-1-yl]-2-trifluoromethylbenzonitrile | 417.4 |
| 18 | 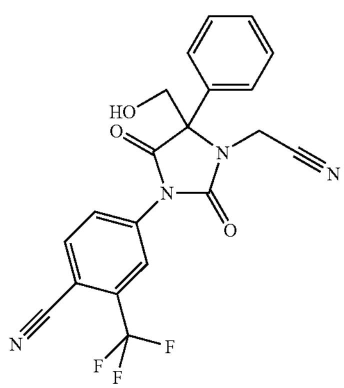 | 4-[3-Cyanomethyl-2,5-dioxo-4-(hydroxymethyl)-4-phenylimidazolidin-1-yl]-2-trifluoromethylbenzonitrile | 414.3 |
| 19 | 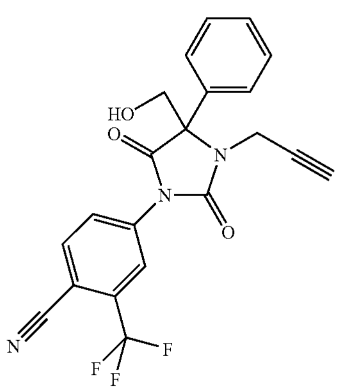 | 4-[2,5-Dioxo-4-(hydroxymethyl)-4-phenyl-3-(1-propynyl)imidazolidin-1-yl]-2-trifluoromethylbenzonitrile | 413.4 |

TABLE 1-continued

Representative compounds of the invention

| ID | Structure | Name | Calc'd MW |
|---|---|---|---|
| 20 | 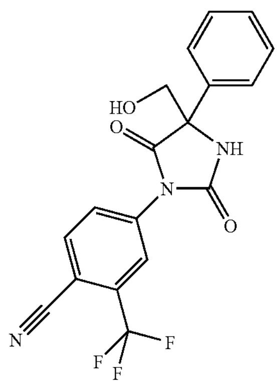 | 4-[2,5-Dioxo-4-hydroxymethyl-4-phenylimidazolidin-1-yl]-2-trifluoromethylbenzonitrile | 375.3 |
| 21 | 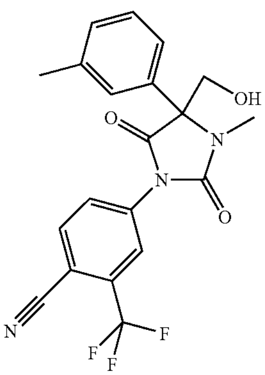 | 4-[2,5-Dioxo-4-hydroxymethyl-3-methyl-4-(3-methylphenyl)imidazolidin-1-yl]-2-trifluoromethylbenzonitrile | 403.4 |
| 22 | 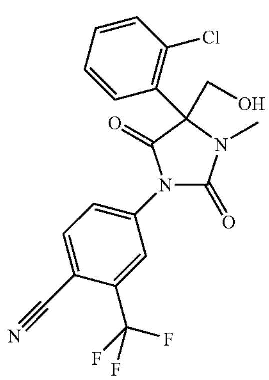 | 4-[4-(2-Chlorophenyl)-2,5-dioxo-4-hydroxymethyl-3-methyl-imidazolidin-1-yl]-2-trifluoromethylbenzonitrile | 423.8 |
| 23 | 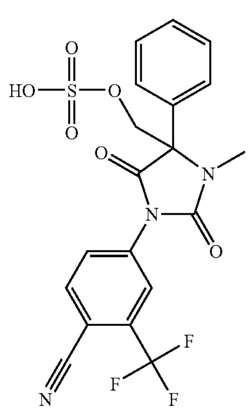 | [1-(4-cyano-3-trifluoromethylphenyl)-2,5-dioxo-3-methyl-4-phenylimidazolidin-4-yl]methyl hydrogen sulfate | 469.06 |

TABLE 1-continued

Representative compounds of the invention

| ID | Structure | Name | Calc'd MW |
|---|---|---|---|
| 24 | 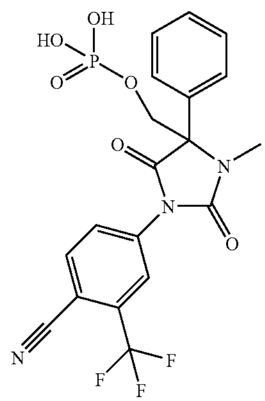 | [1-(4-Cyano-3-trifluoromethylphenyl)-2,5-dioxo-3-methyl-4-phenylimidazolidin-4-yl]methyl dihydrogen phosphate | 469.31 |
| 25 | 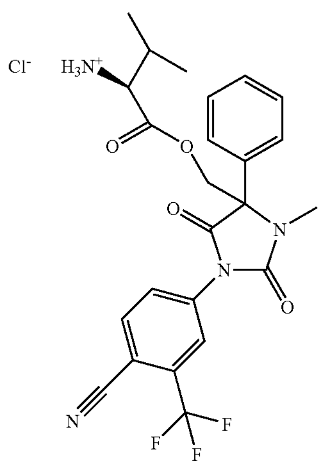 | (2S)-1-[1-(4-Cyano-3-trifluoromethylphenyl)-2,5-dioxo-3-methyl-4-phenylimidazolidin-4-yl]methoxy-3-methyl-1-oxobutan-2-aminium chloride | 488.47 |
| 26 | 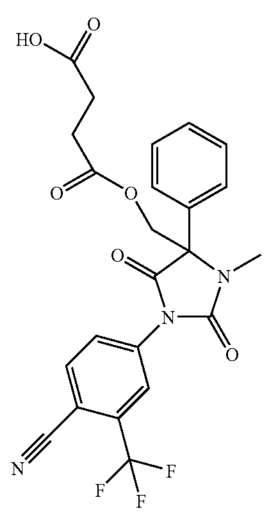 | 4-[1-(4-Cyano-3-trifluoromethylphenyl)-2,5-dioxo-3-methyl-4-phenylimidazolidin-4-yl]methoxy-4-oxobutanoic acid | 489.41 |

TABLE 1-continued

Representative compounds of the invention

| ID | Structure | Name | Calc'd MW |
|----|-----------|------|-----------|
| 27 | 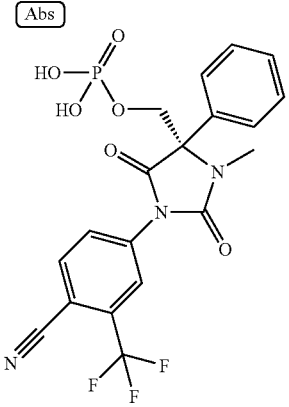 | (S)-(1-(4-cyano-3-(trifluoromethyl)phenyl)-3-methyl-2,5-dioxo-4-phenylimidazolidin-4-yl)methyl dihydrogen phosphate | 469.31 |
| 28 | 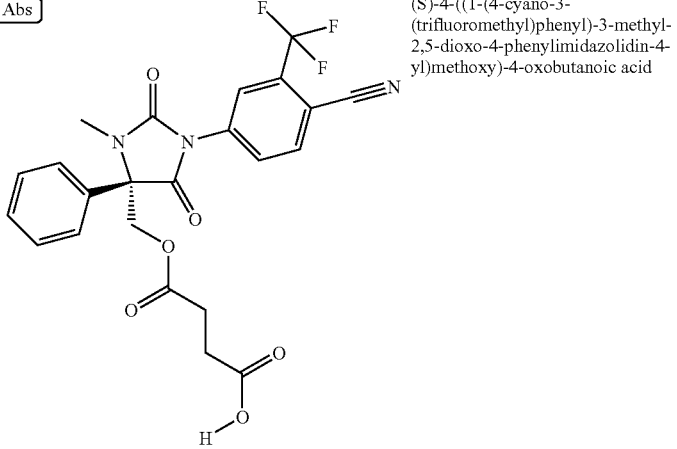 | (S)-4-((1-(4-cyano-3-(trifluoromethyl)phenyl)-3-methyl-2,5-dioxo-4-phenylimidazolidin-4-yl)methoxy)-4-oxobutanoic acid | 489.41 |
| 29 | 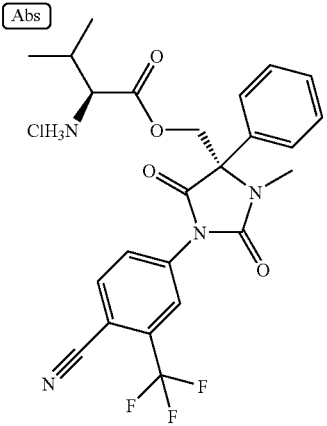 | (S)-((S)-1-(4-cyano-3-(trifluoromethyl)phenyl)-3-methyl-2,5-dioxo-4-phenylimidazolidin-4-yl)methyl-3-methylbutanoate-2-ammonium chloride | 488.47 |

TABLE 1-continued

Representative compounds of the invention

| ID | Structure | Name | Calc'd MW |
|----|-----------|------|-----------|
| 30 | 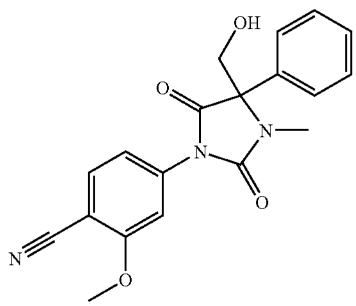 | 4-[2,5-Dioxo-4-hydroxymethyl-3-methyl-4-phenylimidazolidin-1-yl]-2-methoxybenzonitrile | 351.37 |
| 31 | Chiral | (S)-1-(3,4-Dichlorophenyl)-4-hydroxymethyl-3-methyl-4-phenylimidazolidine-2,5-dione | 365.22 |

Biological Examples

The efficacy of the compound of the invention herein described may be demonstrated in vitro in tests of transactivation after simultaneous and stable expression of the human androgen receptor (hAR) and a reporter gene placed under the transcriptional control of the androgen receptor (AR) response elements (ARE) in host cells. This test constitutes a method of identifying pure or partial agonists which mimic the effects of natural hormones, such as DHT (dihydrotestosterone) in the present case or, on the other hand, antagonists which inhibit them.

For this transactivation test, plasmids encoding a reporter gene and the human androgen receptor (hAR) are introduced together by transfection into the HeLa cell line. The reporter plasmid contains luciferase cDNA under the control of the AREs contained in the promoter sequences of the probasin gene (3×pbAREminicoll-luciferase/pGL3-puro). The expression of the reporter gene constitutes an indication of the transcriptional activity of hAR. It also encodes a protein allowing the cells expressing it to resist a treatment with puromycin. The plasmid encoding hAR contains the cDNA of hAR under the control of the Cytomegalovirus (CMV) promoter. It also encodes a protein allowing the cells expressing it to resist a treatment with neomycin. The treatment of cells with increasing amounts of potentially agonistic compounds will increase the expression of the reporter gene. To detect antagonists, on the other hand, increasing doses of test compounds are tested in the presence of increasing concentrations of DHT. The expression of the reporter gene, which is constant for each dose of DHT, decreases when the concentration of the test compounds increases.

1—Tests of Functional Efficacy
1.1 Construction of Plasmids
1.1 a):—Construction of the Puromycin Resistance Plasmid 3×pbareminicoll-Luciferase/pGL3

The first step involves introducing, into the basic pGL3 vector (Promega), the minimal promoter of the collagenase gene upstream of the gene encoding luciferase. Two oligonucleotides (coll-sense and coll-rev) are synthesised. They allow introduction of the sites of cleavage of the restriction enzymes SacI (single underscore in the sequences below) and BglII (double underscore in the sequences below) at the 5' and 3' ends respectively of the sequence between the positions −42 and +46 (bold in the sequences below) of the described promoter sequence [P Angel et al. 1987 Mol. Cell. Biol. 7:2256-2266]. After hybridisation and cloning between the SacI (position 8) and BglII- (position 37) sites of the "pGL3 basic" plasmid, the "minicoll-luciferase/pGL3" plasmid is obtained. The sequence of the oligonucleotides "coll-sense" and "coll-rev" is as follows:

```
coll-sense (SEQ ID No: 1):
5' CACTGTGTCGACGCGTGCAAGGACTCTATATATACAGAGGGAGCTTC
CTAGCTGGGATATTGGAGCAGCAAGAGGCTGGGAAGCCATCACTTACCTT
GCACTGA 3' coll-rev (SEQ ID No: 2):
3' GATCTCAGTGCAAGGTAAGTGATGGCTTCCCAGCCTCTTGCTGCTCC
AATATCCCAGCTAGGAAGCTCCCTCTGTATATATAGAGTCCTTGCACGCG
TCGACACAGTGAGCT 5'
```

The second step involved multimerising 3 times the androgen receptor response element contained on the probasin (pbARE) promoter (bold in the sequences below) (F. Claessens et al. 1996 J. Biol. Chem. 271:19013-19016) and introducing it between the sites KpnI and Ec1136II- of the "minicoll-luciferase/pGL3" plasmid. Two oligonucleotides (coll-sense and coll-rev) are synthesised. They allow introduction of the sites of cleavage of the restriction enzymes KpnI (single underscore in the sequences below) and a blunt end (double underscore in the sequences below) at the 5' and 3' ends respectively. After hybridisation, a DNA fragment is obtained which could be cloned between the sites KpnI (position 1) and Ec1136II (position 8) of the "minicoll-luciferase/pGL3" plasmid, thus generating the "3×pbAREminicoll-luciferase/pGL3" plasmid. The "coll-sense" and "3×pbARE-rev" oligonucleotide sequences are as follows:

```
3xpbARE-sense (SEQ ID No: 3):
5' CAAAGAGCTCTAGCTTAATAGGTTCTTGGAGTACTTTACGTGCTTAA
TAGGTTCTTGGAGTACTTTACGTGCTTAATAGGTTCTTGGAGTACTT
T 3'

3xpbARE-rev (SEQ ID No: 4):
3' AAAGTACTCCAAGAACCTATTAAGCACGTAAAGTACTCCAAGAACCT
ATTAAGCACGTAAAGTACTCCAAGAACCTATTAAGCTAGAGCTCTTTGGT
AC 5'
```

The third step involved introducing the puromycin-resistance gene into the "3×pbAREminicoll-luciferase/pGL3" plasmid. The assembly [promoter puromycin-resistance gene-of polyadenylation sequence of SV40] (fragment 1-1396, Gene library U07648) is subcloned using PCR amplification, starting from the plasmid "pPUR" (Clontech), and using two oligonucleotides (pPUR-sense and pPUR-rev) allowing the cleavage site BamHI to be introduced. The 1,550 base pairs fragment obtained after PCR (30 cycles, 30 seconds at 94° C., 30 seconds at 55° C., 1.5 minutes at 72° C.) is digested by BamHI then cloned at the single BamHI site of the plasmid 3×pbAREminicoll-luciferase/pGL3 thus yielding the puromycin resistance plasmid 3×pbAREminicoll-luciferase/pGL3. The "coll-sense" and "coll-rev" oligonucleotide sequence are as follows:

```
pPUR-sense (SEQ ID No: 5):
5' TAAGGATCCGCTGTGGAATGTGTGTCAGTT 3' pPUR-rev (SEQ ID No: 6):
3' GACGGATCCAGACATGATAAGATACATTGA 3'
```

1.1 b—Construction of the "pcDNA3-hAR" Plasmid

The sequence encoding the hAR cDNA is cloned between the sites EcoRI and XbaI of the pcDNA3.1(+) vector (Invitrogen) starting from the vector psg5-hAR (provided by Professor P. Chambon, IGBMC, Illkirch, France). This plasmid contains the sequence described by Tilley W D et al. [Tilley W D et al. 1989 Proc Natl Acad Sci USA. 86:327-31; Gene library J04150].

1.2 Establishment of the Stable HALP Cell Line

For this test, HeLa cells are obtained from the American Type Culture Collection (Rockville, Md.) and cultivated in DMEM medium containing 4.5 g/L of glucose, supplemented with Glutamax and with nonessential amino-acids and with 10% of foetal calf serum (SVF; Dominique Dutscher).

On the day before transfection, a million cells are seeded in DMEM medium without phenol red, supplemented with Glutamax and with desteroided SVF (5%) in Petri dishes. The cells are transfected with 4 μg of the puromycin resistance plasmids pcDNA3-hAR and 3×pbAREminicoll-luciferase/pGL3 using the reagent "Lipofectamine plus" (Invitrogen), following the supplier's recommendations. The day after transfection, the cells are seeded to different cell densities (10,000 to 100,000 cellules per Petri dish). Two days after transfection, the transfected cells are selected in DMEM medium without phenol red, supplemented with Glutamax and with desteroided SVF (5%) containing 400 μg/mL of G418 (Invitrogen) and 150 ng/mL of puromycin (Sigma). The culture medium is renewed weekly until resistant clones appeared. The resistant clones are removed and amplified before being tested for their functional response.

The functional response test is conducted as follows: The cells are seeded (80,000 cells per well, 48 wells per plate) 24 hours before the phase of stimulation in DMEM medium containing 4.5 g/L of glucose, supplemented with Glutamax and nonessential amino-acids, and with desteroided SVF (5%). On the day of stimulation, the seeding medium is replaced by DMEM medium without phenol red, supplemented with Glutamax and with desteroided SVF (5%) containing a range of concentrations of DHT (1 pM to 1 μM). The cells are placed in contact with the compounds for 18 hours at 37° C. The medium is then removed, the cells lysed and the luciferase activity measured using the reagent "Luciferase assay system" (Promega) in accordance with the manufacturer's instructions. The luminescence produced is detected on a TopCount-type counter (Perkin-Elmer). The clone (HALP2) retained for the screening test showed a transcriptional response curve similar to that obtained after transitory transfection of the same vectors in HeLa cells.

1.3 Functional Response Test

The functional response test is conducted on 96-well plates. The HALP2 cells are seeded (20,000 cells per well) in culture medium (DMEM with phenol red, 1% de Pen-Strep, 1% of non-essential amino acids, 10% of foetal bovine serum, 400 μg/mL Geneticin and 0.150 μg/mL puromycin) on day 1. After 24 hours incubating at 37° C., 5% $CO_2$, high humidity (day 2) the medium is removed and refreshed with test medium (DMEM without phenol red supplemented, 1% de Pen-Strep, 1% of non-essential amino acids and 5% of desteroidised foetal bovine serum). After another 24 hours incubating at 37° C., 5% $CO_2$, high humidity (day 3), the medium is renewed once more before the phase of stimulation.

Stimulation involved crossing a range of concentrations of DHT (0.329 μM to 640 nM) with a range of concentrations of the tested compound (6.4 nM to 4 μM). The cells are placed in contact with the compounds for 24 hours at 37° C., 5% $CO_2$, high humidity. On day 4 the medium is then removed and the luciferase activity reading reagent is placed in contact with the cells in accordance with the manufacturer's instructions (SteadyLite, Perkin-Elmer). The luminescence produced is detected on an Envision reader (Perkin-Elmer).

The agonism is characterised by the $EC_{50}$ value, in other words the concentration of tested compound which induces 50% of the maximum agonistic effect observed with the tested compound. The antagonism is characterised by the $K_{Schild}$ value, in other words the concentration of the tested compound which increases the $EC_{50}$ of the DHT (DiHydroTestosterone) by a factor of 2. This concentration is determined by a conventional Schild regression.

The determination of the relative agonism/antagonism of a compound is obtained by comparing the maximal activation obtained with said compound and the activation obtained with DHT alone (100%).

TABLE 2

Measure of agonism and antagonism of the compound of the invention: Semi quantitative scoring:

| $EC_{50}$ (nM) | | $K_{Schild}$ (nM) | | % effect relative to DHT (100%) | |
|---|---|---|---|---|---|
| 0.01-10 nM: | **** | 0.01-10 nM: | ++++ | 41-50% | §§§§ |
| 11-100 nM: | *** | 11-100 nM: | +++ | 21-40% | §§§ |
| 101-500 nM: | ** | 101-500 nM: | ++ | 6-20% | §§ |
| 501-1000 nM: | * | 501-1000 nM: | + | 0-5% | § |

| $EC_{50}$ ID (nM) | $K_{Schild}$ (nM) | % effect relative to DHT (100%) | Classification |
|---|---|---|---|

TABLE 2-continued

Measure of agonism and antagonism of the compound of the invention:
Semi quantitative scoring:

| 1 | **** | ++++ | §§§ | Mixed agonist/antagonist |
|---|------|------|-----|--------------------------|
| 2 | N/A | +++ | § | Antagonist |
| 3 | N/A | +++ | § | Antagonist |
| 4 | N/A | ++++ | § | Antagonist |
| 5 | N/A | +++ | § | Antagonist |
| 6 | *** | +++ | §§§ | Mixed agonist/antagonist |
| 7 | ** | +++ | §§§ | Mixed agonist/antagonist |
| 8 | ** | +++ | §§ | Mixed agonist/antagonist |
| 9 | **** | ++++ | §§§§ | Mixed agonist/antagonist |
| 10 | *** | +++ | §§§ | Mixed agonist/antagonist |
| 11 | N/A | + | § | Antagonist |
| 12 | **** | +++ | §§§ | Mixed agonist/antagonist |
| 13 | N/A | Not available | § | Antagonist |
| 14 | ** | +++ | §§§ | Mixed agonist/antagonist |
| 15 | ** | ++++ | §§§ | Mixed agonist/antagonist |
| 16 | ** | +++ | §§ | Mixed agonist/antagonist |
| 17 | ** | +++ | §§§§ | Mixed agonist/antagonist |
| 18 | * | N/A | §§ | Mixed agonist/antagonist |
| 19 | ** | +++ | §§ | Mixed agonist/antagonist |
| 20 | N/A | +++ | § | Antagonist |
| 21 | * | ++ | §§ | Mixed agonist/antagonist |
| 23 | not available | not available | not available | not available |
| 24 | **** | +++ | §§§ | Mixed agonist/antagonist |
| 25 | *** | ++ | §§§ | Mixed agonist/antagonist |
| 26 | *** | +++ | §§§ | Mixed agonist/antagonist |

N/A: not applicable

2—Characterisation in animal models 2.1 Adapted model of Hershberger's test The in vivo activity of the compounds of the invention may be demonstrated in an adapted model of the Hershberger test in the following manner:

The selective modulating activity of the androgen receptor is tested in a model of castrated immature young rats. This model, which is widely recognised for evaluating the anabolic effects of androgen compounds on the muscles and on the prostate, has been described by Hershberger et al. 1953 Proc. Soc. Expt. Biol. Med. 83:175.

The method is based on the measurement of the well-known effects of androgens on the growth of the muscles and the accessory male sex organs in animals, and also in men. The consequences of castration appear in the form of a rapid involution and atrophy of the prostate and the seminal vesicles and of the anus-lifting muscle (levator ani). This effect may be completely compensated by an exogenous administration of androgen, in particular of testosterone. The model is thus used to determine the capacity of the tested molecules to maintain the weight of the accessory sex and muscle organs in immature castrated rats, and therefore their androgenic efficacy.

Immature young Sprague Dawley rats (4 to 5 weeks old) weighing approximately 140-160 g (Charles River, Les Oncins, FRANCE) are distributed randomly in various groups and are kept in an environment at 22±2° C. with an alternating day/night cycle of 12 hours and ad libitum access to food and drink.

On day 0 (seven days before commencement of the first treatment) the rats are weighed individually then anaesthetised with an intraperitoneal dose of Ketamine/xylazine (85/15 mg/kg, approximately 2 ml/kg). Each animal is then placed on a sterile field and the abdomen and the scrotum are disinfected with Betadine and 70% alcohol. In the case of the orchidectomised control animals (ORX), the testicles are removed via an incision in the middle of the scrotum. A sterile suture is then made to ligature the supra-testicular portion of the tissue prior to surgical section of each testicle. The groups of animals to be treated by the tested compounds are operated on in an identical manner. In the case of the intact control animals (SHAM), the testicles are similarly extracted and reintroduced delicately to their original location. The site of surgical intervention is then sutured using sterile suture thread, and the site is disinfected again by application of Betadine. Each animal is then kept under a sterile pad until it awoke, before being returned to its cage. The animals are kept in an environment at 22 ±2° C. with an alternating day/night cycle of 12 hours and ad libitum access to food and drink. The animals are treated with the molecules to be tested from post-surgery day 7 and until day 10 preceding sacrifice (day 11).

The rats are split into groups and treated daily from day 7 to day 10 under the conditions defined below:
1. SHAM control group: Vehicle (PEG400/DMSO/water; 79/1/20) administered per os.
2. ORX control group: Vehicle (PEG400/DMSO/water; 79/1/20) administered per os.
3. Treated ORX group: The tested compounds are administered individually per os in suspension in the vehicle described above, in a dose of 10 mg/kg.

After treatment for 4 successive days, the animals are decapitated using a guillotine. The levator ani and the ventral prostate are removed and weighed individually. For comparing inter-experimental data, the weight of each organ is standardised and expressed in milligrammes per 100 g of the weight of the animal (W). For each organ, the average of the standardised weights of the ORX control group is fixed by definition at 0% and the average of the standardised weights of the SHAM control group is fixed by definition at 100%. The efficacy of each product is expressed as a percentage and calculated using the following formula:

$$(W\text{treated}-W\text{ORX})/(W\text{SHAM}-W\text{ORX})\times 100$$

A subsequent ANOVA test is used for statistical analysis to identify the differences between groups.

TABLE 3

Herschberger's test data for selected compounds of the invention.

| Example | Dose tested (mg/kg) | Anabolic activity % | Androgenic activity % (Prostate) |
|---------|---------------------|---------------------|----------------------------------|
| 6 | 30 | ** | * |
| 7 | 10 | ** | 0 |
| 9 | 10 | *** | * |
| 10 | 10 | **** | * |
| 11 | 30 | *** | * |
| 12 | 10 | **** | *** |
| 13 | 10 | * | * |
| 14 | 10 | **** | ** |
| 15 | 10 | ** | 0 |

TABLE 3-continued

Herschberger's test data for selected compounds of the invention.

| Example | Dose tested (mg/kg) | Anabolic activity % | Androgenic activity % (Prostate) |
|---|---|---|---|
| 16 | 10 | **** | * |
| 17 | 10 | **** | *** |
| 18 | 10 | **** | * |
| 19 | 10 | **** | ** |
| 21 | 10 | * | 0 |

Semi quantitative scoring
0.5-25% *
25-50% **
50-75% ***
75-100% ****

3. Determination of Absolute Bioavailability

To screen rapidly imidazolidines derivatives based on their absolute bioavailabity, restricted pharmacokinetic profile with only fours sampling time points after oral and intravenous route is investigated in Sprague Dawley rats as follows: each test compound is dosed orally (10 mg/kg) and intravenously (3 mg/kg) to groups of 3 male Sprague Dawley rats. Oral doses are administered as solution in EtOH/PEG400/$H_2O$ (1/79/20; v/v) by esophageal gavage (2 mg/mL; 5 mL/kg) and intravenous dose is given as solution in DMSO/PEG400/$H_2O$ (1/65/34; v/v) as a bolus in the tail vein (3 mg/mL; 1 mL/kg). Before oral dosing, animals are deprived of food (water ad libitum) for at least 16 hours before the start of the study and 6 hours after administration.

Blood is collected at the retro-orbital sinus into polypropylene tubes (Li-heparinate) at +4° C. at the following sampling-times: 0.083, 0.25, 1 and 3 h after intravenous injection and 0.25, 1, 3 and 6 hours after oral dosing. Three (3) animals are sampled per time-point; each animal being sampled four times. After centrifugation at 5000 rpm for 10 min at +4° C., plasma is collected into polypropylene tubes and kept frozen at −20° C. pending assays. Plasma samples are assayed by a LC-MS/MS method with a lower limit of quantification of 1 to 10 ng/mL depending on the compound (volume of plasma: 100 µL).

A LC-MS/MS method for quantification in heparinized plasma was developed for each test compound. Sample preparation consists of a precipitation of plasma proteins with methanol and filtration by centrifugation of supernatant on Captiva deep-well 96 0.2 µm filter plates. Water was added to methanol supernatant phase prior to analysis by liquid chromatography (Pursuit 5 C18 20×2,0 mm VARIAN, 2 µL loop, gradient Water/Methanol (90/10 to 0/100) over 1.7 min) with turboionspray tandem mass spectrometry (API4000) in negative mode using multiple reaction monitoring. The method includes 8 standard and 3 quality control levels with lower limit of quantification corresponding to first standard level.

Exposures are determined using a non compartmental model (WinNonLin 2.1) and the absolute bioavailability (F) is calculated as follows: [AUC(0-6 h) oral*3 mg/kg]/AUC (0-3 h) IV 10 mg/kg] and expressed in percentage.

TABLE 4

Measure of bioavailability of representative compounds of the invention:

| ID | Bioavailability |
|---|---|
| 1 | ## |
| 3 | ## |
| 4 | # |
| 5 | ### |
| 6 | ## |
| 7 | ### |
| 8 | ### |
| 10 | ### |
| 12 | ## |

Semi quantitative scoring:
>90% ###
50-90%: ##
0-49% #

4. Determination of the Absolute Bioavailability of Selected Compounds of the Invention in Rats and Dogs Absolute bioavailabity of a drug after oral dosing with the corresponding ester prodrugs is investigated in Sprague Dawley rats as follows: each prodrug is dosed orally (10 mg/kg i.e. 8 mg/kg drug equivalent dose) and the drug is dosed intravenously (3 mg/kg) to groups of 3 male Sprague Dawley rats. Oral doses are administered as solution in EtOH/PEG400/$H_2O$ (1/79/20; v/v) by esophageal gavage (2 mg/mL; 5 mL/kg) and intravenous dose is given as solution in DMSO/PEG400/$H_2O$ (1/65/34; v/v) as a bolus in the tail vein (0.6 mg/mL; 5 mL/kg). Before oral dosing, animals are deprived of food (water ad libitum) for at least 16 hours before the start of the study and 6 hours after administration.

Blood is taken via a catheter inserted in the jugular vein and collected into polypropylene tubes (Li-heparinate) at +4° C. at the following sampling-times: 0.05, 0.25, 0.5, 1, 3, 5 and 8 h after intravenous injection and 0.25, 0.5, 1, 3, 5, 8 and 24 hours after oral dosing. To prevent any ex-vivo cleavage of prodrug into drug, a volume of PMSF (5 mg/mL of phenylmethylsulfonyl fluoride in ethanolic solution) corresponding to 10% of blood volume collected is added to collection tubes. Three (3) animals are sampled per time-point. After centrifugation at 5000 rpm for 3 min at +4° C., plasma is collected into polypropylene tubes and kept frozen at −20° C. pending assays.

In dogs, the absolute bioavailability of a drug after oral dosing with the corresponding ester prodrugs is investigated as follows: each prodrug is dosed orally (10 mg/kg drug equivalent dose) and the drug is dosed intravenously (3 mg/kg) to 3 male Beagle dogs. Oral doses are administered as powder filled into gelatin capsule and intravenous dose is given as solution in DMSO/PEG400/$H_2O$ (1/65/34; v/v) as a bolus in the cepahalic vein (3 mg/mL; 1 mL/kg). Before oral dosing, animals are deprived of food (water ad libitum) for at least 12 hours before the start of the study and 4 hours after administration.

Blood is taken by direct venepuncture at jugular vein of each of the three dogs and collected into polypropylene tubes (Li-heparinate) at +4° C. at the following sampling-times: 0.083, 0.167, 0.25, 0.5, 1, 2, 4, 8, 10 and 24 h after intravenous injection and 0.25, 0.5, 1, 2, 4, 6, 8, 10 and 24 hours after oral dosing. As no cleavage of prodrug into drug, occurs ex-vivo in dog plasma, no esterase inhibitor is added to collection tubes. After centrifugation at 5000 rpm for 3 min at +4° C., plasma is collected into polypropylene tubes and kept frozen at −20° C. pending assays.

Drug level is determined in rat and dog plasma samples by a LC-MS/MS method with a lower limit of quantification of 1 ng/mL (volume of plasma: 25 µL). Sample preparation consisted of a precipitation of plasma proteins with methanol and filtration by centrifugation of supernatant on Captiva deep-well 96 0.2 µm filter plates. Water was added to methanol supernatant phase prior to analysis by liquid chromatography (Pursuit 5 C18 20×2,0 mm VARIAN, 2 µL loop, gradient Water/Methanol (90/10 to 0/100) over 1.7 min) with turboionspray tandem mass spectrometry (API4000) in negative mode using multiple reaction monitoring. The method includes 8 standard and 3 quality control levels with lower limit of quantification corresponding to first standard level.

Exposures are determined using a non compartmental model (WinNonLin 5.2) and the absolute bioavailability (F) is calculated as follows: [AUC(0–z) oral*3 mg/kg]/AUC (0–z) IV 8 or 10 mg/kg] and expressed in percentage.

TABLE 5

Measure of the absolute bioavailability of selected compounds of the invention:

| ID | Bioavailability Rat | Bioavailability Dog |
|---|---|---|
| 27 | ## | |
| 28 | ### | |

>90% ####
50-90%: ###
20-49% ##
<20% #

5. In-Vivo Experiments.
5.1 Glucocorticoid-Induced Muscle Loss (Rat).

In this model the impact of the compound of the invention on muscle loss induced by dexamethasone is investigated (Kun Ma et al, 2003). Male rats Sprague Dawley of 8 week-old are treated daily with 0.3 mg/kg of dexamethasone by subcutaneous administration during 15 days. Rats are divided into several groups: sham (no treatment, n=8), control (vehicle alone, n=8), nandrolone decanoate (3 mg/kg/day, s.c., n=8) and the tested compound (selected oral dose range, n=8). After 15 days of treatment the gastrocnemeius is collected and weighed and the muscle function is determined on the tibialis anterior (Houré et al, 2009).

5.2 TNF-Induced Cachexia (Mice)

In this model (Dario Coletti et al, 2005), the production of tumor necrosis factor-α (TNF) is induced by electroporation of DNA with TNF gene expression in the tibialis of mice. Chronic exposure to TNF triggers a muscle wasting reminiscent of cachexia. Male mice are divided into several groups: sham, control, nandrolone decanoate and G100192. At the end of the treatment the gastrocnemeius and the soleus are collected, weighed and the muscle function is determined on the soleus (Houré et al, 2009).

5.3 IMMOBILIZATION MODEL (MICE)

Skeletal unloading causes bone and muscle loss. The effects of the compound of the invention on the skeletal unloading are investigated using tail-suspension for 14 days (Roland et al, 2005). Male mice were divided into several groups unsuspended, tail-suspended, tail-suspended treated with the tested compound and tail-suspended treated with nandrolone decanoate. At the end of the experiment, the soleus and the gastrocnemeius are collected, weighed and the muscle function is determined on the soleus (Houré et al, 2009).

5.4 Orchidectomized Model (Rat)

Orchidectomy increase bone turnover and muscle fat mass. The effect of the compound of the invention, both muscle composition (ration lean to fat mass) and bone turn-over is investigated in this model (Houré et al, 2009). Male rats Sprague Dalwey of 8 week-old are divided into several groups: intact rats (sham), orchidectomized rats treated for 2 months with either vehicle, nandrolone decanoate or the tested compound. At the end of the experiment the ratio of lean to fat mass and bone turnover are studied, the gastrocnemeius is collected and weighed and the muscle function is determined on the soleus (Houré et al, 2009).

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS® /DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

REFERENCES

1. Kaufman J M and Vermeulen A. *Endocr Rev.* 2005, 26, 833-76. The decline of androgen levels in elderly men and its clinical and therapeutic implications
2. Liu P Y et al. *J. Clin. Endocrinol. Metab.* 2004, 89, 4789-96 Clinical review, 171: The rationale, efficacy and safety of androgen therapy in older men: future research and current practice recommendations.
3. Davison S L and Davis S R. *J. Steroid Biochem. Mol. Biol.* 2003, 85, 363-366 Androgens in women.
4. Mohler et al. *Expert Opin. Ther. Patents* 2005, 15(11), 1565-1585
5. EP-A-0966447
6. EP-A-0572191
7. WO 2007/137874
8. Bundgard, H. *Design of Prodrugs* 1985, Elsevier, Amsterdam
9. *Remington's Pharmaceutical Sciences, 17th edition,* 1985, Mack Publishing Company, Easton, Pa.
10. Greene, T. W. and Wuts, P. G. M. *Protecting Groups in Organic Synthesis, Second Edition* 1991, Wiley, New York,
11. Molander, G. A. and McKie, J. A. *J. Org. Chem.* 1995, 60, 872-882
12. Angel, P. et al. *Mol. Cell. Biol.* 1987, 7:2256-2266
13. Claessens, F. et al. *J. Biol. Chem.* 1996, 271:19013-19016

14. Tilley, W D et al. *Proc Natl Acad Sci USA*. 1989, 86:327-31 Gene library J04150
15. Hershberger et al. *Proc. Soc. Expt. Biol. Med.* 1953, 83:175
16. Kun Ma, Con Mallidis, Shalender Bhasin, Vahid Mahabadi, Jorge Artaza, Nestor Gonzalez-Cadavid, Jose Arias and Behrouz Salehian *Am J Physiol Endocrinol Metab.* 2003, 285: E363-E371;
  Glucocorticoid-induced skeletal muscle atrophy is associated with upregulation of myostatin gene expression.
17. C. Hourdé, C. Jagerschmidt, P. Clément-Lacroix, A. Vignaud, P. Ammann, G. S. Butler-Browne and A. Ferry *Acta Physiol.* 2009, 195: 471-482.
  Androgen replacement therapy improves function in male rat muscles independently of hypertrophy and activation of the Akt/mTOR pathway.
18. Dario Coletti, Viviana Moresi, Sergio Adamo, Mario Molinaro and David Sassoon *Genesis* 2005 43:120-128
  Tumor Necrosis Factor-α Gene Transfer Induces Cachexia and Inhibits Muscle Regeneration.
19. Roland M, Hanson A M, Cannon C M, Stodieck L S, Ferguson V L. *Biomed Sci Instrum.* 2005, 41:128-34.
  Exercise prevention of unloading-induced bone and muscle loss in adult mice.

What is claimed is:

1. A compound according to Formula Ib:

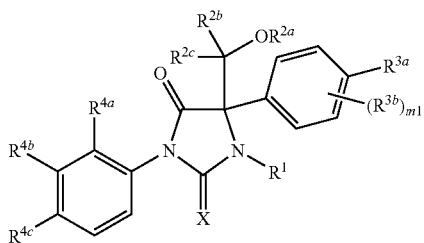

wherein

X is O or S;

$R^1$ is selected from $C_1$-$C_6$ alkyl, $C_3$-$C_7$ cycloalkyl, $C_3$-$C_6$ alkenyl, $C_3$-$C_6$ alkynyl, and $C_1$-$C_6$ acyl; each of which may optionally be substituted with cyano, one or more halo, hydroxyl, or $C_1$-$C_6$ alkoxy;

$R^{2a}$ is selected from H, P(O)(OH)$_2$, and C(O)(CH$_2$)$_{n1}$C(O)OH; or $R^{2a}$ is selected from $C_1$-$C_6$ acyl, and $C_3$-$C_6$ alkenyl; each of which may optionally be substituted with amino, or carboxy; n1 is 0, 1, 2, 3, or 4;

each $R^{2b}$ and $R^{2c}$ is independently selected from H, and $C_1$-$C_6$ alkyl; or $R^{2b}$ and $R^{2c}$ may join together to form a $C_3$-$C_7$ cycloalkyl;

$R^{3a}$ is H, halo, cyano, or nitro; or $R^{3a}$ is $C_1$-$C_6$ alkyl optionally substituted with halo, cyano, nitro, hydroxyl, or $C_1$-$C_4$ alkoxy; or $R^{3a}$ is amido optionally substituted with $C_1$-$C_6$ alkyl;

each $R^{3b}$ is independently halo, cyano, or nitro; or each $R^{3b}$ is independently $C_1$-$C_6$ alkyl optionally substituted with cyano, or halo; or each $R^{3b}$ is amido optionally substituted with $C_1$-$C_6$ alkyl;

each $R^{4a}$, and $R^{4b}$ is independently H, halo, cyano, carboxy or nitro; or each $R^{4a}$, and $R^{4b}$ is selected from $C_1$-$C_6$ alkyl, and $C_1$-$C_6$ alkoxy; each of which may optionally be substituted by one or more halo, or $C_1$-$C_6$ alkoxy; or $R^{4a}$ and $R^{4b}$ are joined together to form an 5 or 6- membered cycloalkyl, 5 or 6-membered heterocycloalkyl, 5 or 6-membered aryl, or 5 or 6-membered heteroaryl;

$R^{4c}$ is halo, cyano, or nitro; and m1 is 0, 1, or 2;

or pharmaceutically acceptable salts thereof.

2. A compound or pharmaceutically acceptable salt thereof, according to claim 1, wherein X is O.

3. A compound or pharmaceutically acceptable salt thereof, according to claim 1 wherein $R^{2b}$ is H.

4. A compound or pharmaceutically acceptable salt thereof, according to claim 1 wherein $R^{2b}$ is Me or Et.

5. A compound or pharmaceutically acceptable salt thereof, according to claim 1 wherein $R^{2c}$ is H or $C_1$-$C_6$ alkyl.

6. A compound or pharmaceutically acceptable salt thereof, according to claim 5 wherein $R^{2c}$ is H, Me or Et.

7. A compound or pharmaceutically acceptable salt thereof, according to claim 1, wherein $R^{2b}$ and $R^{2c}$ are joined together to form a cyclopropyl, or cyclobutyl ring.

8. A compound or pharmaceutically acceptable salt thereof, according to claim 1, wherein each of $R^{2b}$ and $R^{2c}$ are H.

9. A compound or pharmaceutically acceptable salt thereof, according to claim 1 wherein $R^{2a}$ is H, P(O)(OH)$_2$, or $C_1$-$C_6$ acyl.

10. A compound or pharmaceutically acceptable salt thereof, according to claim 1 wherein $R^{2a}$ is $C_3$-$C_6$ alkenyl.

11. A compound or pharmaceutically acceptable salt thereof, according to claim 10 wherein $R^{2a}$ is CH$_2$—CH=CH$_2$.

12. A compound or pharmaceutically acceptable salt thereof, according to claim 9 wherein $R^{2a}$ is H.

13. A compound or pharmaceutically acceptable salt thereof according to claim 9 wherein $R^{2a}$ is P(O)(OH)$_2$.

14. A pharmaceutically acceptable salt according to claim 1 wherein $R^{2a}$ is P(O)(OH)$_2$ and the salt is a mono or bis salt thereof.

15. A pharmaceutically acceptable salt according to claim 14, wherein $R^{2a}$ is P(O)(ONa)$_2$.

16. A compound or pharmaceutically acceptable salt thereof, according to claim 1 wherein $R^{2a}$ is C(O)(CH$_2$)$_{n1}$C(O)OH; and n1 is 0, 1, 2, or 3.

17. A compound or pharmaceutically acceptable salt thereof, according to claim 16 wherein $R^{2a}$ is C(O)—CH$_2$CH$_2$—C(O)OH.

18. A pharmaceutically acceptable salt according to claim 17 wherein $R^{2a}$ is a pharmaceutically acceptable salt of C(O)—CH$_2$CH$_2$—C(O)OH.

19. A pharmaceutically acceptable salt according to claim 18 wherein $R^{2a}$ is C(O)—CH$_2$CH$_2$—C(O)ONa.

20. A compound or pharmaceutically acceptable salt thereof, according to claim 1 wherein $R^{2a}$ is C(O)—CH(iPr)NH$_2$.

21. A pharmaceutically acceptable salt according to claim 20; wherein $R^{2a}$ is a pharmaceutically acceptable salt of C(O)—CH(iPr)NH$_2$.

22. A pharmaceutically acceptable salt according to claim 21 wherein $R^{2a}$ is C(O)—CH(iPr)NH$_3$Cl.

23. A compound or pharmaceutically acceptable salt thereof, according to claim 1 wherein $R^1$ is $C_1$-$C_6$ alkyl optionally substituted with halo, cyano or hydroxy.

24. A compound or pharmaceutically acceptable salt thereof, according to claim 23 wherein $R^1$ is $C_1$-$C_6$ alkyl optionally substituted with cyano.

25. A compound or pharmaceutically acceptable salt thereof, according to claim 1 wherein $R^1$ is $C_3$-$C_6$ alkynyl.

26. A compound or pharmaceutically acceptable salt thereof, according to claim 25 wherein $R^1$ is —CH$_2$—C≡CH.

27. A compound or pharmaceutically acceptable salt thereof, according to claim 23 wherein $R_1$ is Me, Et, i-Pr, or n-Pr.

28. A compound or a pharmaceutically acceptable salt thereof, according to claim 23 wherein $R^1$ is Me.

29. A compound or pharmaceutically acceptable salt thereof, according to claim 1, wherein the compound is according to Formula II

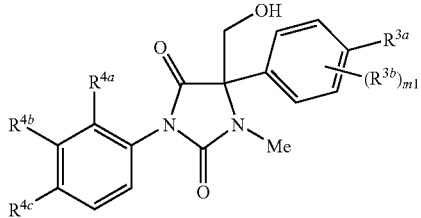

II wherein $R^{3a}$, $R^{3b}$, $R^{4a}$, $R^{4b}$, $R^{4c}$, and m1 are as in claim 1.

30. A compound or pharmaceutically acceptable salt thereof, according to claim 1, wherein $R^{4c}$ is cyano, halo or nitro.

31. A compound or pharmaceutically acceptable salt thereof, according to claim 30, wherein $R^{4c}$ is cyano.

32. A compound or pharmaceutically acceptable salt thereof, according to claim 1, wherein $R^{4b}$ is H, halo, cyano, $C_1$-$C_6$ alkyl, or $C_1$-$C_6$ haloalkyl.

33. A compound or pharmaceutically acceptable salt thereof, according to claim 32, wherein $R^{4b}$ is Cl, F, CN or CF$_3$.

34. A compound or pharmaceutically acceptable salt thereof, according to claim 33, wherein $R^{4b}$ is CF$_3$.

35. A compound or pharmaceutically acceptable salt thereof, according to claim 1, wherein $R^{4a}$ is H, halo, cyano, $C_1$-$C_6$ alkyl, or $C_1$-$C_6$ haloalkyl.

36. A compound or pharmaceutically acceptable salt thereof, according to claim 35 wherein $R^{4a}$ is Cl or F.

37. A compound or pharmaceutically acceptable salt thereof, according to claim 35, wherein $R^{4a}$ is H.

38. A compound or pharmaceutically acceptable salt thereof, according to claim 1, wherein the compound is according to Formulae IIIa or IIIb:

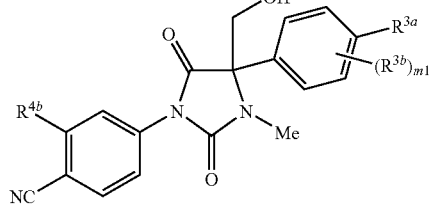

IIIa

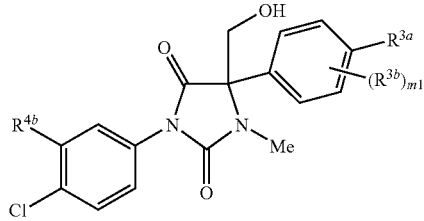

IIIb wherein $R^{3a}$, $R^{3b}$, $R^{4b}$, and m1 are as in claim 1.

39. A compound or pharmaceutically acceptable salt thereof, according to claim 38, wherein $R^{4b}$ is H, halo, cyano, $C_1$-$C_6$ alkyl, or $C_1$-$C_6$ haloalkyl.

40. A compound or pharmaceutically acceptable salt thereof, according to claim 39, wherein $R^{4b}$ is Cl, F, CN or CF$_3$.

41. A compound or pharmaceutically acceptable salt thereof, according to claim 40 wherein $R^{4b}$ is CF$_3$.

42. A compound or pharmaceutically acceptable salt thereof, according to claim 1, wherein the compound is according to Formulae IVa or IVb:

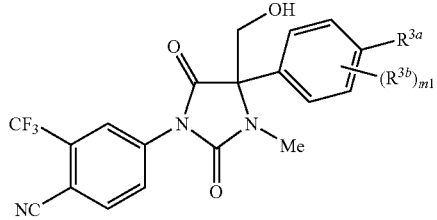

IVa

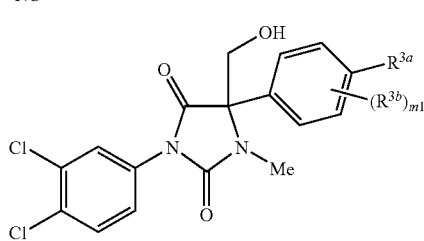

IVb wherein $R^{3a}$, $R^{3b}$, and m1 are as in claim 1.

43. A compound or pharmaceutically acceptable salt thereof, according to claim 1, wherein $R^{3a}$ is H, halo, cyano, $C_1$-$C_6$ alkyl, or $C_1$-$C_6$ haloalkyl.

44. A compound or pharmaceutically acceptable salt thereof, according to claim 43, wherein $R^{3a}$ is H, Me, Cl, F, CN or CF$_3$.

45. A compound or pharmaceutically acceptable salt thereof, according to claim 1, wherein m1 is 1 or 2.

46. A compound or pharmaceutically acceptable salt thereof, according to claim 1, wherein $R^{3b}$ is halo, cyano, $C_1$-$C_6$ alkyl, or $C_1$-$C_6$ haloalkyl.

47. A compound or pharmaceutically acceptable salt thereof, according to claim 46, wherein $R^{3b}$ is Me, Cl, F, CN or $CF_3$.

48. A compound or pharmaceutically acceptable salt thereof, according to claim 1, wherein m1 is 0.

49. A compound or pharmaceutically acceptable salt thereof, according to claim 1, wherein the compound is according to Formulae Va, Vb, Vc or Vd:

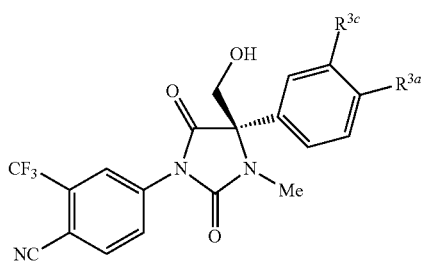

Va

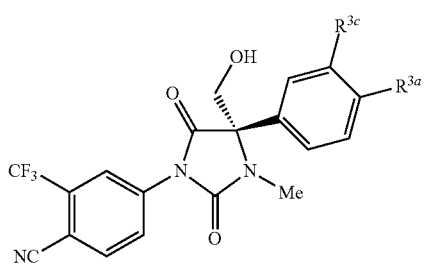

Vb

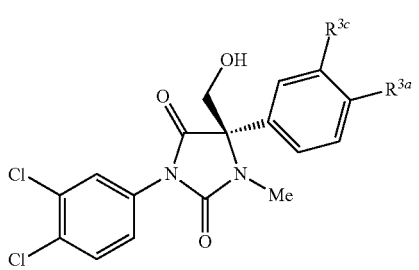

Vc

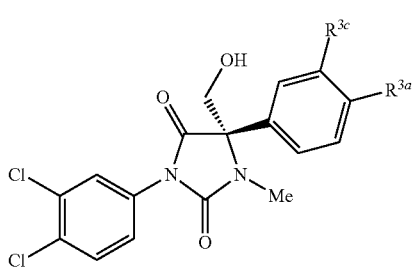

Vd and wherein
$R^{3a}$ is as in claim 1; and
$R^{3c}$ is H, halo, cyano, or nitro; or
$R^{3c}$ is $C_1$-$C_6$ alkyl optionally substituted with cyano, or halo; or
$R^{3c}$ is amido optionally substituted with $C_1$-$C_6$ alkyl.

50. A compound or pharmaceutically acceptable salt thereof, according to claim 49, wherein $R^{3a}$ is H, halo, or cyano; and $R^{3c}$ is H.

51. A compound or pharmaceutically acceptable salt thereof, according to claim 50, wherein $R^{3a}$ is H, CN, Cl, or F and $R^{3c}$ is H.

52. A compound or pharmaceutically acceptable salt thereof, according to claim 49, wherein $R^{3a}$ is H; and $R^{3c}$ is H, halo, $C_1$-$C_6$ alkyl, $C_1$-$C_6$ haloalkyl, or cyano.

53. A compound or pharmaceutically acceptable salt thereof, according to claim 52, wherein $R^{3a}$ is H; and $R^{3c}$ is CN, Cl, F, Me or $CF_3$.

54. A compound or pharmaceutically acceptable salt thereof, according to claim 49, wherein each $R^{3a}$ and $R^{3c}$ is H.

55. A compound or pharmaceutically acceptable salt thereof, according to claim 1, wherein the compound is selected from:
- 4-[2,5-Dioxo-4-(hydroxymethyl)-3-methyl-4-phenylimidazolidin-1-yl]-2-trifluoromethylbenzonitrile;
- 4-[2,5-Dioxo-4-(1-hydroxypropyl)-3-methyl-4-phenylimidazolidin-1-yl]-2-trifluoromethylbenzonitrile;
- 4-[2,5-Dioxo-4-(1-hydroxyethyl)-3-methyl-4-phenylimidazolidin-1-yl]-2-trifluoromethylbenzonitrile;
- 4-[2,5-Dioxo-4-(4-fluorophenyl)-4-(hydroxymethyl)-3-methylimidazolidin-1-yl]-2-trifluoromethylbenzonitrile;
- 4-[4-(4-Chlorophenyl)-2,5-dioxo-4-hydroxymethyl-3-methyl-imidazolidin-1-yl]-2-trifluoromethylbenzonitrile;
- 4-[2,5-Dioxo-4-(4-fluorophenyl)-4-hydroxymethyl-3-(2-propynyl)imidazolidin-1-yl]-2-trifluoromethylbenzonitrile;
- 4-[4-(3-Chlorophenyl)-2,5-dioxo-4-hydroxymethyl-3-methyl-imidazolidin-1-yl]-2-trifluoromethylbenzonitrile;
- (S)-4-[2,5-Dioxo-4-(hydroxymethyl)-3-methyl-4-phenylimidazolidin-1-yl]-2-trifluoromethylbenzonitrile;
- (R)-4-[2,5-Dioxo-4-(hydroxymethyl)-3-methyl-4-phenylimidazolidin-1-yl]-2-trifluoromethylbenzonitrile;
- 4-[2,5-Dioxo-3-ethyl-4-(hydroxymethyl)-4-phenylimidazolidin-1-yl]-2-trifluoromethylbenzonitrile;
- 4-[4-(4-Cyanophenyl)-2,5-dioxo-4-hydroxymethyl-3-methylimidazolidin-1-yl]-2-trifluoromethylbenzonitrile
- 4-[4-(3-Cyanophenyl)-2,5-dioxo-4-hydroxymethyl-3-methylimidazolidin-1-yl]-2-trifluoromethylbenzonitrile;
- 4-[2,5-Dioxo-4-hydroxymethyl-3-methyl-4-(3-trifluoromethylphenyl)imidazolidin-1-yl]-2-trifluoromethylbenzonitrile;
- 1-(3,4-Dichlorophenyl)-4-hydroxymethyl-3-methyl-4-phenylimidazolidine-2,5-dione
- 4-[2,5-Dioxo-4-(hydroxymethyl)-3-(1-methylethyl)-4-phenylimidazolidin-1-yl]-2-trifluoromethylbenzonitrile;
- 4-[3-Cyanomethyl-2,5-dioxo-4-(hydroxymethyl)-4-phenylimidazolidin-1-yl]-2-trifluoromethylbenzonitrile;
- 4-[2,5-Dioxo-4-(hydroxymethyl)-4-phenyl-3-(1-propynyl)imidazolidin-1-yl]-2-trifluoromethylbenzonitrile
- 4-[2,5-Dioxo-4-hydroxymethyl-4-phenylimidazolidin-1-yl]-2-trifluoromethylbenzonitrile;
- 4-[2,5-Dioxo-4-hydroxymethyl-3-methyl-4-(3-methylphenyl)imidazolidin-1-yl]-2-trifluoromethylbenzonitrile;
- 4-[4-(2-Chlorophenyl)-2,5-dioxo-4-hydroxymethyl-3-methyl-imidazolidin-1-yl]-2-trifluoromethylbenzonitrile;
- [1-(4-Cyano-3-trifluoromethylphenyl)-2,5-dioxo-3-methyl-4-phenylimidazolidin-4-yl]methyl dihydrogen phosphate;
- (2S)-1-[1-(4-Cyano-3-trifluoromethylphenyl)-2,5-dioxo-3-methyl-4-phenylimidazolidin -4-yl]methoxy-3-methyl-1-oxobutan-2-aminium chloride;
- 4-[1-(4-Cyano-3-trifluoromethylphenyl)-2,5-dioxo-3-methyl-4-phenylimidazolidin-4-yl]methoxy-4-oxobutanoic acid;

(S)-(1-(4-cyano-3-(trifluoromethyl)phenyl)-3-methyl-2, 5-dioxo-4-phenylimidazolidin -4-yl)methyl dihydrogen phosphate;

(S)-4-((1-(4-cyano-3-(trifluoromethyl)phenyl)-3-methyl-2,5-dioxo-4phenylimidazolidin-4-yl)methoxy)-4-oxobutanoic acid;

(S)-((S)-1-(4-cyano-3-(trifluoromethyl)phenyl)-3-methyl-2,5-dioxo-4-phenylimidazolidin-4-yl)methyl-3-methylbutanoate-2-ammonium chloride;

4- [2,5-Dioxo-4-hydroxymethyl-3-methyl-4-phenylimidazolidin-1-yl]-2-methoxybenzonitrile; and (S)-1-(3,4-Dichlorophenyl)-4-hydroxymethyl-3-methyl-4-phenylimidazolidine-2,5-dione.

56. A pharmaceutical composition comprising a pharmaceutically acceptable carrier and a pharmaceutically effective amount of a compound according to claim 1.

57. A method for the treatment of a condition selected from cachexia, osteoporosis, sarcopenia, a decline in libido and/or sexual dysfunction, comprising administering an agonist or mixed agonist/antagonist compound or pharmaceutically acceptable salt thereof, according to claim 1.

* * * * *

SEQUENCE LISTING

<160> NUMBER OF SEQ ID NOS: 6

<210> SEQ ID NO 1
<211> LENGTH: 104
<212> TYPE: DNA
<213> ORGANISM: Artificial Sequence
<220> FEATURE:
<223> OTHER INFORMATION: Plasmid

<400> SEQUENCE: 1
cactgtgtcg acgcgtgcaa ggactctata tatacagagg gagcttccta gctgggatat    60
tggagcagca agaggctggg aagccatcac ttaccttgca ctga                    104

<210> SEQ ID NO 2
<211> LENGTH: 112
<212> TYPE: DNA
<213> ORGANISM: Artificial Sequence
<220> FEATURE:
<223> OTHER INFORMATION: plasmid

<400> SEQUENCE: 2
gatctcagtg caaggtaagt gatggcttcc cagcctcttg ctgctccaat atcccagcta    60
ggaagctccc tctgtatata tagagtcctt gcacgcgtcg acacagtgag ct           112

<210> SEQ ID NO 3
<211> LENGTH: 95
<212> TYPE: DNA
<213> ORGANISM: Artificial Sequence
<220> FEATURE:
<223> OTHER INFORMATION: plasmid

<400> SEQUENCE: 3
caaagagctc tagcttaata ggttcttgga gtactttacg tgcttaatag gttcttggag    60
tactttacgt gcttaatagg ttcttggagt acttt                              95

<210> SEQ ID NO 4
<211> LENGTH: 99
<212> TYPE: DNA
<213> ORGANISM: Artificial Sequence
<220> FEATURE:
<223> OTHER INFORMATION: plasmid

<400> SEQUENCE: 4
aaagtactcc aagaacctat taagcacgta aagtactcca agaacctatt aagcacgtaa    60
agtactccaa gaacctatta agctagagct ctttggtac                          99

<210> SEQ ID NO 5
<211> LENGTH: 30

```
<212> TYPE: DNA
<213> ORGANISM: Artificial Sequence
<220> FEATURE:
<223> OTHER INFORMATION: plasmid

<400> SEQUENCE: 5
taaggatccg ctgtggaatg tgtgtcagtt                                    30

<210> SEQ ID NO 6
<211> LENGTH: 30
<212> TYPE: DNA
<213> ORGANISM: Artificial Sequence
<220> FEATURE:
<223> OTHER INFORMATION: plasmid

<400> SEQUENCE: 6
gacggatcca gacatgataa gatacattga                                    30
```